(12) United States Patent
Goldfarb et al.

(10) Patent No.: US 10,856,727 B2
(45) Date of Patent: Dec. 8, 2020

(54) ENDOSCOPIC METHODS AND DEVICES FOR TRANSNASAL PROCEDURES

(71) Applicant: Acclarent, Inc., Irvine, CA (US)

(72) Inventors: Eric Goldfarb, Belmont, CA (US); John H. Morriss, Emerald Hills, CA (US); John Y. Chang, Los Altos, CA (US)

(73) Assignee: Acclarent, Inc., Irvine, CA (US)

( * ) Notice: Subject to any disclaimer, the term of this patent is extended or adjusted under 35 U.S.C. 154(b) by 384 days.

(21) Appl. No.: 15/802,637

(22) Filed: Nov. 3, 2017

(65) Prior Publication Data

US 2018/0125336 A1 May 10, 2018

Related U.S. Application Data

(60) Continuation of application No. 14/993,444, filed on Jan. 12, 2016, now abandoned, which is a
(Continued)

(51) Int. Cl.
| | |
|---|---|
| *A61B 1/00* | (2006.01) |
| *A61B 1/005* | (2006.01) |
| *A61B 1/233* | (2006.01) |
| *A61B 1/01* | (2006.01) |
| *A61B 1/06* | (2006.01) |

(Continued)

(52) U.S. Cl.
CPC ........ *A61B 1/00154* (2013.01); *A61B 1/0014* (2013.01); *A61B 1/0051* (2013.01); *A61B 1/00135* (2013.01); *A61B 1/01* (2013.01); *A61B 1/04* (2013.01); *A61B 1/0607* (2013.01); *A61B 1/07* (2013.01); *A61B 1/233* (2013.01); *A61B 17/24* (2013.01); *A61M 29/02* (2013.01); *A61B 17/3421* (2013.01); *A61B 2017/003* (2013.01); *A61B 2017/246* (2013.01); *A61B 2017/3447* (2013.01)

(58) Field of Classification Search
CPC . A61B 1/00089; A61B 1/008; A61B 1/00082; A61B 1/00085; A61B 1/00087; A61B 1/000091; A61B 1/00094; A61B 1/00096; A61B 1/00098; A61B 1/00101
USPC ................................. 600/121–125, 180–200
See application file for complete search history.

(56) References Cited

U.S. PATENT DOCUMENTS

| | | |
|---|---|---|
| 446,173 A | 2/1891 | Hancock |
| 504,424 A | 9/1893 | De Pezzer |

(Continued)

FOREIGN PATENT DOCUMENTS

| | | |
|---|---|---|
| CA | 2013323 | 9/1990 |
| CH | 668188 | 12/1988 |

(Continued)

OTHER PUBLICATIONS

Argon Medical. Maxxim Medical. Ad for Sniper EliteTM Hydrophilie Ni-Ti Alloy Guidewire (2001).
(Continued)

*Primary Examiner* — Matthew J Kasztejna
(74) *Attorney, Agent, or Firm* — Frost Brown Todd LLC

(57) ABSTRACT

Medical devices, systems and methods that are useable to facilitate transnasal insertion and positioning of guidewires and various other devices and instruments at desired locations within the ear, nose, throat, paranasal sinuses or cranium.

19 Claims, 27 Drawing Sheets

Related U.S. Application Data continuation of application No. 11/888,284, filed on Jul. 31, 2007, now Pat. No. 9,265,407, which is a division of application No. 11/647,530, filed on Dec. 27, 2006, now abandoned, which is a continuation-in-part of application No. 11/522,497, filed on Sep. 15, 2006, now Pat. No. 7,559,925, and a continuation-in-part of application No. 11/193,020, filed on Jul. 29, 2005, now abandoned, which is a continuation-in-part of application No. 11/150,847, filed on Jun. 10, 2005, now Pat. No. 7,803,150, and a continuation-in-part of application No. 11/116,118, filed on Apr. 26, 2005, now Pat. No. 7,720,521, and a continuation-in-part of application No. 10/944,270, filed on Sep. 17, 2004, now abandoned, and a continuation-in-part of application No. 10/829,917, filed on Apr. 21, 2004, now Pat. No. 7,654,997.

(60) Provisional application No. 60/844,874, filed on Sep. 15, 2006.

(51) Int. Cl.
*A61B 1/07* (2006.01)
*A61B 17/24* (2006.01)
*A61B 1/04* (2006.01)
*A61M 29/02* (2006.01)
*A61B 17/34* (2006.01)
*A61B 17/00* (2006.01)

(56) References Cited

U.S. PATENT DOCUMENTS

| | | |
|---|---|---|
| 513,667 A | 1/1894 | Buckingham |
| 705,346 A | 7/1902 | Hamilton |
| 798,775 A | 9/1905 | Forsyte |
| 816,792 A | 4/1906 | Green |
| 1,080,934 A | 12/1913 | Shackleford |
| 1,200,267 A | 10/1916 | Sunnergren |
| 1,650,959 A | 11/1927 | Pitman |
| 1,735,519 A | 11/1929 | Vance |
| 1,828,986 A | 10/1931 | Stevens |
| 1,878,671 A | 9/1932 | Cantor |
| 2,201,749 A | 5/1940 | Vandegrift |
| 2,493,326 A | 1/1950 | Trinder |
| 2,525,183 A | 10/1950 | Robison |
| 2,847,997 A | 8/1958 | Tibone |
| 2,899,227 A | 8/1959 | Jeanrenaed |
| 2,906,179 A | 9/1959 | Bower |
| 2,995,832 A | 8/1961 | Alderson |
| 3,009,265 A | 11/1961 | Bexark |
| 3,037,286 A | 6/1962 | Bower |
| 3,173,418 A | 3/1965 | baran |
| 3,347,061 A | 10/1967 | Stuemky |
| 3,376,659 A | 4/1968 | Asin et al. |
| 3,384,970 A | 5/1968 | Avalear |
| 3,393,073 A | 7/1968 | Reutenauer et al. |
| 3,435,826 A | 4/1969 | Fogarty |
| 3,447,091 A | 5/1969 | Russell et al. |
| 3,469,578 A | 9/1969 | Bierman |
| 3,477,438 A | 11/1969 | Allen et al. |
| 3,481,043 A | 12/1969 | Esch |
| 3,486,539 A | 12/1969 | Jacuzzi |
| 3,506,005 A | 4/1970 | Gilio et al. |
| 3,509,638 A | 5/1970 | Macleod |
| 3,515,137 A | 6/1970 | Santomieri |
| 3,515,888 A | 6/1970 | Lewis |
| 3,527,220 A | 9/1970 | Summers |
| 3,531,868 A | 10/1970 | Stevenson |
| 3,552,384 A | 1/1971 | Pierie et al. |
| 3,624,661 A | 11/1971 | Shebanow |
| 3,731,963 A | 5/1973 | Pond |
| 3,766,924 A | 10/1973 | Pidgeon |
| 3,792,391 A | 2/1974 | Ewing |
| 3,802,096 A | 4/1974 | Matern |
| 3,804,081 A | 4/1974 | Kinoshita |
| 3,800,788 A | 7/1974 | White |
| 3,834,394 A | 9/1974 | Hunter et al. |
| 3,847,145 A | 11/1974 | Grossan |
| 3,850,176 A | 11/1974 | Gottschalk |
| 3,856,000 A | 12/1974 | Chikama |
| 3,859,993 A | 1/1975 | Bitner |
| 3,871,365 A | 3/1975 | Chikama |
| 3,894,538 A | 7/1975 | Richter |
| 3,903,893 A | 9/1975 | Scheer |
| 3,910,617 A | 10/1975 | Scalza et al. |
| 3,921,636 A | 11/1975 | Zaffaroni |
| 3,948,254 A | 4/1976 | Zaffaroni |
| 3,948,262 A | 4/1976 | Zaffaroni |
| 3,967,618 A | 7/1976 | Zaffaroni |
| 3,993,069 A | 11/1976 | Buckles et al. |
| 3,993,072 A | 11/1976 | Zaffaroni |
| 3,993,073 A | 11/1976 | Zaffaroni |
| 4,016,251 A | 4/1977 | Higuchi et al. |
| 4,052,505 A | 10/1977 | Higuchi et al. |
| 4,053,975 A | 10/1977 | Olbrich et al. |
| 4,069,307 A | 1/1978 | Higuchi et al. |
| 4,102,342 A | 7/1978 | Akiyama et al. |
| 4,138,151 A | 2/1979 | Nakao |
| 4,184,497 A | 1/1980 | Kolff et al. |
| 4,198,766 A | 4/1980 | Camin et al. |
| 4,207,890 A | 6/1980 | Mamajek et al. |
| 4,209,919 A | 7/1980 | Kirikae et al. |
| 4,213,095 A | 7/1980 | Falconer |
| 4,217,898 A | 8/1980 | Theeuwes |
| 4,268,115 A | 5/1981 | Slemon et al. |
| 4,299,226 A | 11/1981 | Banka |
| 4,299,227 A | 11/1981 | Lincoff |
| 4,311,146 A | 1/1982 | Wonder |
| 4,312,353 A | 1/1982 | Shahbabian |
| 4,338,941 A | 7/1982 | Payton |
| D269,204 S | 5/1983 | Trepp |
| 4,388,941 A | 6/1983 | Riedhammer |
| RE31,351 E | 8/1983 | Falconer |
| 4,435,716 A | 3/1984 | Zandbergen |
| 4,437,856 A | 3/1984 | Valli |
| 4,441,495 A | 4/1984 | Hicswa |
| 4,445,892 A | 5/1984 | Hussein et al. |
| 4,450,150 A | 5/1984 | Sidman |
| 4,459,977 A | 7/1984 | Pizon et al. |
| 4,464,175 A | 8/1984 | Altman et al. |
| 4,471,779 A | 9/1984 | Antoshkiw et al. |
| 4,499,899 A | 2/1985 | Lyons, III |
| 4,517,979 A | 5/1985 | Pecenka |
| 4,554,929 A | 11/1985 | Samson et al. |
| 4,564,364 A | 1/1986 | Zaffaroni et al. |
| 4,571,239 A | 2/1986 | Heyman |
| 4,571,240 A | 2/1986 | Samson et al. |
| 4,581,017 A | 4/1986 | Sahota |
| 4,585,000 A | 4/1986 | Hershenson |
| D283,921 S | 5/1986 | Dyak |
| 4,589,868 A | 5/1986 | Dretler |
| 4,592,357 A | 6/1986 | Ersek |
| 4,596,528 A | 6/1986 | Lewis et al. |
| D284,892 S | 7/1986 | Glassman |
| 4,603,564 A | 8/1986 | Kleinhany et al. |
| 4,606,346 A | 8/1986 | Berg et al. |
| 4,607,622 A | 8/1986 | Fritch et al. |
| 4,637,389 A | 1/1987 | Heyden |
| 4,639,244 A | 1/1987 | Rizk et al. |
| 4,641,654 A | 2/1987 | Samson et al. |
| 4,645,495 A | 2/1987 | Vaillancourt |
| 4,669,469 A | 6/1987 | Gifford, III |
| 4,672,961 A | 6/1987 | Davies |
| 4,675,613 A | 6/1987 | Naegeli et al. |
| 4,682,607 A | 7/1987 | Vaillancourt et al. |
| 4,686,965 A | 8/1987 | Bonnet et al. |
| 4,691,948 A | 9/1987 | Austin, Jr. et al. |
| 4,696,544 A | 9/1987 | Costella |
| 4,700,694 A | 10/1987 | Shishido |
| 4,708,434 A | 11/1987 | Tsuno |
| 4,708,834 A | 11/1987 | Cohen et al. |

(56) References Cited

U.S. PATENT DOCUMENTS

| | | |
|---|---|---|
| 4,726,772 A | 2/1988 | Amplatz |
| 4,736,970 A | 4/1988 | McGourty et al. |
| 4,737,141 A | 4/1988 | Spits |
| 4,748,869 A | 6/1988 | Ohtsuka |
| 4,748,969 A | 6/1988 | Wardle |
| 4,748,986 A | 6/1988 | Morrison et al. |
| 4,753,637 A | 6/1988 | Horneffer |
| 4,755,171 A | 7/1988 | Tennant |
| 4,771,776 A | 9/1988 | Powell et al. |
| 4,784,117 A | 11/1988 | Miyazaki |
| 4,793,359 A | 12/1988 | Sharrow |
| 4,795,439 A | 1/1989 | Guest |
| 4,796,629 A | 1/1989 | Grayzel |
| 4,802,461 A | 2/1989 | Cho |
| 4,803,076 A | 2/1989 | Ranade |
| 4,811,743 A | 3/1989 | Stevens |
| 4,815,478 A | 3/1989 | Buchbinder et al. |
| 4,819,619 A | 4/1989 | Augustine et al. |
| 4,834,709 A | 5/1989 | Banning et al. |
| 4,846,186 A | 7/1989 | Box et al. |
| 4,847,258 A | 7/1989 | Sturm et al. |
| 4,851,228 A | 7/1989 | Zentner et al. |
| 4,854,330 A | 8/1989 | Evans, III et al. |
| 4,862,874 A | 9/1989 | Kellner |
| 4,867,138 A | 9/1989 | Kubota et al. |
| 4,883,465 A | 11/1989 | Brennan |
| 4,897,651 A | 1/1990 | DeMonte |
| 4,898,577 A | 2/1990 | Badger et al. |
| 4,917,419 A | 4/1990 | Mora, Jr. et al. |
| 4,917,667 A | 4/1990 | Jackson |
| 4,919,112 A | 4/1990 | Siegmund |
| 4,920,967 A | 5/1990 | Cottonaro et al. |
| 4,925,445 A | 5/1990 | Sakamoto et al. |
| 4,940,062 A | 7/1990 | Hampton et al. |
| 4,943,275 A | 7/1990 | Stricker |
| 4,946,466 A | 8/1990 | Pinchuk et al. |
| 4,953,553 A | 9/1990 | Tremulis |
| 4,961,433 A | 10/1990 | Christian |
| 4,961,738 A | 10/1990 | Mackin |
| 4,966,163 A | 10/1990 | Kraus et al. |
| 4,984,581 A | 1/1991 | Stice |
| 4,986,810 A | 1/1991 | Semrad |
| 4,991,588 A | 2/1991 | Pflueger et al. |
| 4,994,033 A | 2/1991 | Shockey et al. |
| 4,998,916 A | 3/1991 | Hammerslag et al. |
| 4,998,917 A | 3/1991 | Gaiser et al. |
| 5,001,825 A | 3/1991 | Halpern |
| 5,002,322 A | 3/1991 | Fukumoto |
| 5,009,655 A | 4/1991 | Daignault, Jr. et al. |
| 5,019,075 A | 5/1991 | Spears et al. |
| 5,019,372 A | 5/1991 | Folkman et al. |
| 5,020,514 A | 6/1991 | Heckele |
| 5,021,043 A | 6/1991 | Becker et al. |
| 5,024,650 A | 6/1991 | Hagiwara et al. |
| 5,024,658 A | 6/1991 | Kozlov et al. |
| 5,026,384 A | 6/1991 | Farr et al. |
| 5,030,227 A | 7/1991 | Rosenbluth et al. |
| 5,040,548 A | 8/1991 | Yock |
| 5,041,089 A | 8/1991 | Mueller et al. |
| 5,044,678 A | 9/1991 | Detweiler |
| 5,049,132 A | 9/1991 | Shaffer et al. |
| 5,053,007 A | 10/1991 | Euteneuer |
| 5,055,051 A | 10/1991 | Duncan |
| 5,060,660 A | 10/1991 | Gambale et al. |
| 5,067,489 A | 11/1991 | Lind |
| 5,069,226 A | 12/1991 | Yamauchi et al. |
| 5,084,010 A | 1/1992 | Plaia et al. |
| 5,087,244 A | 2/1992 | Wolinsky et al. |
| 5,087,246 A | 2/1992 | Smith |
| 5,090,595 A | 2/1992 | Vandeninck |
| 5,090,910 A | 2/1992 | Narlo |
| 5,090,959 A | 2/1992 | Samson et al. |
| 5,099,845 A | 3/1992 | Besz et al. |
| 5,102,402 A | 4/1992 | Dror et al. |
| 5,112,228 A | 5/1992 | Zouras |
| 5,116,311 A | 5/1992 | Lofstedt |
| 5,127,393 A | 7/1992 | McFarlin et al. |
| 5,137,517 A | 8/1992 | Loney et al. |
| 5,139,510 A | 8/1992 | Goldsmith, III et al. |
| 5,139,832 A | 8/1992 | Hayashi et al. |
| D329,496 S | 9/1992 | Wotton |
| 5,152,747 A | 10/1992 | Oliver |
| 5,156,595 A | 10/1992 | Adams |
| 5,161,534 A | 11/1992 | Berthiaume |
| 5,163,989 A | 11/1992 | Campbell et al. |
| 5,165,420 A | 11/1992 | Strickland |
| 5,167,220 A | 12/1992 | Brown |
| 5,168,864 A | 12/1992 | Shockey |
| 5,169,386 A | 12/1992 | Becker et al. |
| 5,171,233 A | 12/1992 | Amplatz et al. |
| 5,180,368 A | 1/1993 | Garrison |
| 5,183,470 A | 2/1993 | Wettermann |
| 5,189,110 A | 2/1993 | Ikematu et al. |
| 5,195,168 A | 3/1993 | Yong |
| 5,195,971 A | 3/1993 | Sirhan |
| 5,197,457 A | 3/1993 | Adair |
| 5,201,908 A | 4/1993 | Jones |
| 5,207,695 A | 5/1993 | Trout, III |
| 5,211,952 A | 5/1993 | Spicer et al. |
| 5,213,576 A | 5/1993 | Abiuso et al. |
| 5,215,105 A | 6/1993 | Kizelshteyn et al. |
| 5,221,260 A | 6/1993 | Burns et al. |
| 5,226,302 A | 7/1993 | Anderson |
| 5,230,348 A | 7/1993 | Ishibe et al. |
| 5,236,422 A | 8/1993 | Eplett, Jr. |
| 5,238,004 A | 8/1993 | Sahatjian et al. |
| 5,243,996 A | 9/1993 | Hall |
| D340,111 S | 10/1993 | Yoshikawa |
| 5,250,059 A | 10/1993 | Andreas et al. |
| 5,251,092 A | 10/1993 | Brady et al. |
| 5,252,183 A | 10/1993 | Shaban et al. |
| 5,255,679 A | 10/1993 | Imran |
| 5,256,144 A | 10/1993 | Kraus et al. |
| 5,263,926 A | 11/1993 | Wilk |
| 5,264,260 A | 11/1993 | Saab |
| 5,267,965 A | 12/1993 | Deniega |
| 5,269,752 A | 12/1993 | Bennett |
| 5,270,086 A | 12/1993 | Hamlin |
| 5,273,052 A | 12/1993 | Kraus et al. |
| 5,275,593 A | 1/1994 | Easley et al. |
| 5,286,254 A | 2/1994 | Shapland et al. |
| 5,290,310 A | 3/1994 | Makower et al. |
| 5,292,305 A | 3/1994 | Boudewijn et al. |
| 5,295,694 A | 3/1994 | Levin |
| 5,300,085 A | 4/1994 | Yock |
| 5,304,123 A | 4/1994 | Atala et al. |
| 5,306,272 A | 4/1994 | Cohen et al. |
| 5,308,326 A | 5/1994 | Zimmon |
| 5,312,430 A | 5/1994 | Rosenbluth et al. |
| 5,313,967 A | 5/1994 | Lieber et al. |
| 5,314,408 A | 5/1994 | Salmon et al. |
| 5,314,417 A | 5/1994 | Stephens et al. |
| 5,314,443 A | 5/1994 | Rudnick |
| 5,315,618 A | 5/1994 | Yoshida |
| 5,315,985 A * | 5/1994 | Decarie ............ A61B 1/00144 600/101 |
| 5,318,528 A | 6/1994 | Heaven et al. |
| 5,324,306 A | 6/1994 | Makower et al. |
| 5,333,620 A | 8/1994 | Moutafis et al. |
| 5,334,143 A | 8/1994 | Carroll |
| 5,334,167 A | 8/1994 | Cocanower |
| 5,334,187 A | 8/1994 | Fischell et al. |
| 5,335,671 A | 8/1994 | Clement |
| 5,336,163 A | 8/1994 | DeMane et al. |
| 5,341,818 A | 8/1994 | Abrams et al. |
| 5,342,296 A | 8/1994 | Persson et al. |
| 5,343,865 A | 9/1994 | Gardineer et al. |
| 5,345,945 A | 9/1994 | Hodgson et al. |
| 5,346,075 A | 9/1994 | Nichols et al. |
| 5,346,508 A | 9/1994 | Hastings |
| 5,348,537 A | 9/1994 | Wiesner et al. |
| 5,350,396 A | 9/1994 | Eliachar |
| 5,356,418 A | 10/1994 | Shturman |
| 5,368,049 A | 11/1994 | Raman et al. |

(56) References Cited

U.S. PATENT DOCUMENTS

| | | |
|---|---|---|
| 5,368,558 A | 11/1994 | Nita |
| 5,368,566 A | 11/1994 | Crocker |
| 5,370,640 A | 12/1994 | Kolff |
| 5,372,138 A | 12/1994 | Crowley et al. |
| 5,372,584 A | 12/1994 | Zink et al. |
| D355,031 S | 1/1995 | Yoshikawa |
| 5,378,234 A | 1/1995 | Hammerslag et al. |
| 5,385,562 A | 1/1995 | Adams et al. |
| 5,386,817 A | 2/1995 | Jones |
| 5,386,828 A | 2/1995 | Owens et al. |
| 5,391,147 A | 2/1995 | Imran et al. |
| 5,391,179 A | 2/1995 | Mezzoli |
| 5,395,367 A | 3/1995 | Wilk |
| 5,402,799 A | 4/1995 | Colon et al. |
| 5,409,444 A | 4/1995 | Kensey |
| 5,411,475 A | 5/1995 | Atala et al. |
| 5,411,476 A | 5/1995 | Abrams et al. |
| 5,411,477 A | 5/1995 | Saab |
| 5,415,633 A | 5/1995 | Lazarus |
| 5,425,370 A | 6/1995 | Vilkomerson |
| 5,439,446 A | 8/1995 | Barry |
| 5,441,494 A | 8/1995 | Ortiz |
| 5,441,497 A | 8/1995 | Narciso, Jr. |
| 5,445,646 A | 8/1995 | Euteneuer et al. |
| 5,447,497 A | 9/1995 | Sogard et al. |
| 5,450,853 A | 9/1995 | Hastings et al. |
| 5,451,221 A | 9/1995 | Cho et al. |
| 5,454,817 A | 10/1995 | Katz |
| 5,458,572 A | 10/1995 | Campbell et al. |
| 5,459,700 A | 10/1995 | Jacobs |
| 5,465,717 A | 11/1995 | Imran et al. |
| 5,465,733 A | 11/1995 | Hinohara et al. |
| 5,478,309 A | 12/1995 | Sweezer et al. |
| 5,478,565 A | 12/1995 | Geria |
| 5,486,181 A | 1/1996 | Cohen et al. |
| 5,496,338 A | 3/1996 | Miyagi et al. |
| 5,497,783 A | 3/1996 | Urick et al. |
| 5,507,301 A | 4/1996 | Wasicek et al. |
| 5,507,725 A | 4/1996 | Savage et al. |
| 5,507,766 A | 4/1996 | Kugo et al. |
| 5,507,795 A | 4/1996 | Chiang et al. |
| 5,512,055 A | 4/1996 | Domb et al. |
| 5,514,128 A | 5/1996 | Hillsman et al. |
| 5,519,532 A | 5/1996 | Broome |
| 5,531,676 A | 7/1996 | Edwards et al. |
| 5,533,985 A | 7/1996 | Wang |
| 5,538,008 A | 7/1996 | Crowe |
| 5,546,964 A | 8/1996 | Stangerup |
| 5,549,542 A | 8/1996 | Kovalcheck |
| 5,558,073 A | 9/1996 | Pomeranz et al. |
| 5,558,652 A | 9/1996 | Henke |
| 5,562,619 A | 10/1996 | Mirarchi et al. |
| 5,568,809 A | 10/1996 | Ben-Haim |
| 5,571,086 A | 11/1996 | Kaplan et al. |
| 5,578,007 A | 11/1996 | Imran |
| 5,578,048 A | 11/1996 | Pasqualucci et al. |
| 5,582,575 A | 12/1996 | Heckele et al. |
| 5,584,827 A | 12/1996 | Korteweg et al. |
| 5,591,194 A | 1/1997 | Berthiaume |
| 5,599,284 A | 2/1997 | Shea |
| 5,599,304 A | 2/1997 | Shaari |
| 5,599,576 A | 2/1997 | Opolski |
| 5,601,087 A | 2/1997 | Gunderson et al. |
| 5,601,594 A | 2/1997 | Best |
| 5,607,386 A | 3/1997 | Flam |
| 5,617,870 A | 4/1997 | Hastings et al. |
| 5,626,374 A | 5/1997 | Kim |
| 5,633,000 A | 5/1997 | Grossman et al. |
| 5,634,908 A | 6/1997 | Loomas |
| 5,638,819 A | 6/1997 | Manwaring et al. |
| 5,643,251 A | 7/1997 | Hillsman et al. |
| 5,645,789 A | 7/1997 | Roucher, Jr. |
| 5,647,361 A | 7/1997 | Damadian |
| 5,653,690 A | 8/1997 | Booth et al. |
| 5,656,030 A | 8/1997 | Hunjan et al. |
| 5,662,674 A | 9/1997 | Debbas |
| 5,664,567 A | 9/1997 | Linder |
| 5,664,580 A | 9/1997 | Erickson et al. |
| 5,665,052 A | 9/1997 | Bullard |
| 5,669,388 A | 9/1997 | Vilkomerson |
| 5,673,707 A | 10/1997 | Chandrasekaran |
| 5,676,673 A | 10/1997 | Ferre et al. |
| 5,679,400 A | 10/1997 | Tuch |
| 5,682,199 A | 10/1997 | Lankford |
| 5,685,838 A | 11/1997 | Peters et al. |
| 5,685,847 A | 11/1997 | Barry |
| 5,690,373 A | 11/1997 | Luker |
| 5,693,065 A | 12/1997 | Rains, III |
| 5,694,945 A | 12/1997 | Ben-Haim |
| 5,697,159 A | 12/1997 | Linden |
| 5,700,286 A | 12/1997 | Tartaglia et al. |
| 5,707,376 A | 1/1998 | Kavteladze et al. |
| 5,707,389 A | 1/1998 | Louw et al. |
| 5,708,175 A | 1/1998 | Loyanagi et al. |
| 5,711,315 A | 1/1998 | Jerusalmy |
| 5,713,839 A | 2/1998 | Shea |
| 5,713,946 A | 2/1998 | Ben-Haim |
| 5,718,702 A * | 2/1998 | Edwards ............ A61B 10/0233 604/22 |
| 5,720,300 A | 2/1998 | Fagan et al. |
| 5,720,719 A | 2/1998 | Edwards et al. |
| 5,722,401 A | 3/1998 | Pietroski et al. |
| 5,722,984 A | 3/1998 | Fischell et al. |
| 5,729,129 A | 3/1998 | Acker |
| 5,730,128 A | 3/1998 | Pomeranz et al. |
| 5,733,248 A | 3/1998 | Adams et al. |
| 5,749,357 A | 5/1998 | Linder |
| 5,749,889 A * | 5/1998 | Bacich ............ A61B 17/3417 600/104 |
| 5,749,920 A | 5/1998 | Quiachon et al. |
| 5,752,513 A | 5/1998 | Acker et al. |
| 5,752,971 A | 5/1998 | Rosenbluth et al. |
| 5,762,604 A | 6/1998 | Kieturakis |
| 5,766,158 A | 6/1998 | Opolski |
| 5,769,821 A | 6/1998 | Abrahamson et al. |
| 5,775,327 A | 7/1998 | Randolph et al. |
| 5,776,158 A | 7/1998 | Chou |
| 5,779,699 A | 7/1998 | Lipson |
| 5,789,391 A | 8/1998 | Jacobus et al. |
| 5,792,100 A | 8/1998 | Shantha |
| 5,797,878 A | 8/1998 | Bleam |
| 5,803,089 A | 9/1998 | Ferre et al. |
| 5,814,016 A | 9/1998 | Valley et al. |
| 5,819,723 A | 10/1998 | Joseph |
| 5,820,568 A | 10/1998 | Willis |
| 5,820,592 A | 10/1998 | Hammerslag |
| 5,823,961 A | 10/1998 | Fields et al. |
| 5,824,044 A | 10/1998 | Quiachon et al. |
| 5,824,048 A | 10/1998 | Tuch |
| 5,824,173 A | 10/1998 | Fontirroche et al. |
| 5,826,576 A | 10/1998 | West |
| 5,827,224 A | 10/1998 | Shippert |
| 5,827,323 A | 10/1998 | Klieman et al. |
| 5,830,188 A | 11/1998 | Abouleish |
| 5,833,608 A | 11/1998 | Acker |
| 5,833,645 A | 11/1998 | Lieber et al. |
| 5,833,650 A | 11/1998 | Imran |
| 5,833,682 A | 11/1998 | Amplatz et al. |
| 5,836,638 A | 11/1998 | Slocum |
| 5,836,935 A | 11/1998 | Ashton et al. |
| 5,836,951 A | 11/1998 | Rosenbluth et al. |
| 5,837,313 A | 11/1998 | Ding et al. |
| 5,843,089 A | 12/1998 | Sahatjian et al. |
| 5,843,113 A | 12/1998 | High |
| 5,846,259 A | 12/1998 | Berthiaume |
| 5,857,998 A | 1/1999 | Barry |
| 5,862,693 A | 1/1999 | Myers et al. |
| 5,865,767 A | 2/1999 | Frechette et al. |
| 5,872,879 A | 2/1999 | Hamm |
| 5,873,835 A | 2/1999 | Hastings |
| 5,879,324 A | 3/1999 | Von Hoffmann |
| 5,882,333 A | 3/1999 | Schaer et al. |
| 5,882,346 A | 3/1999 | Pomeranz et al. |
| 5,887,467 A | 3/1999 | Butterweck et al. |

(56) References Cited

U.S. PATENT DOCUMENTS

| | | |
|---|---|---|
| 5,902,247 A | 5/1999 | Coe et al. |
| 5,902,333 A | 5/1999 | Roberts et al. |
| 5,904,701 A | 5/1999 | Daneshvar |
| 5,908,407 A | 6/1999 | Frazee et al. |
| 5,916,193 A | 6/1999 | Stevens et al. |
| 5,916,213 A | 6/1999 | Haissaguerre et al. |
| 5,928,192 A | 7/1999 | Maahs |
| 5,931,811 A | 8/1999 | Haissaguerre et al. |
| 5,931,818 A | 8/1999 | Werp et al. |
| 5,932,035 A | 8/1999 | Koger et al. |
| 5,935,061 A | 8/1999 | Acker et al. |
| 5,941,816 A | 8/1999 | Barthel et al. |
| D413,629 S | 9/1999 | Wolff et al. |
| 5,947,988 A | 9/1999 | Smith |
| 5,949,929 A | 9/1999 | Hamm |
| 5,954,693 A | 9/1999 | Barry |
| 5,954,694 A | 9/1999 | Sunseri |
| 5,957,842 A | 9/1999 | Littmann et al. |
| 5,967,984 A | 10/1999 | Chu et al. |
| 5,968,085 A | 10/1999 | Morris et al. |
| 5,971,975 A | 10/1999 | Mills et al. |
| 5,976,074 A | 11/1999 | Moriyama |
| 5,979,290 A | 11/1999 | Simeone |
| 5,980,503 A | 11/1999 | Chin |
| 5,980,551 A | 11/1999 | Summers et al. |
| 5,984,945 A | 11/1999 | Sirhan |
| 5,985,307 A | 11/1999 | Hanson et al. |
| 5,987,344 A | 11/1999 | West |
| 5,993,462 A | 11/1999 | Pomeranz et al. |
| 5,997,562 A | 12/1999 | Zadno-Azizi et al. |
| 6,006,126 A | 12/1999 | Cosman |
| 6,006,130 A | 12/1999 | Higo et al. |
| 6,007,516 A | 12/1999 | Burbank et al. |
| 6,007,991 A | 12/1999 | Sivaraman et al. |
| 6,010,511 A | 1/2000 | Murphy |
| 6,013,019 A | 1/2000 | Fischell et al. |
| 6,015,414 A | 1/2000 | Werp et al. |
| 6,016,429 A | 1/2000 | Khafizov et al. |
| 6,016,439 A | 1/2000 | Acker |
| 6,019,736 A | 2/2000 | Avellanet et al. |
| 6,019,777 A | 2/2000 | Mackenzie |
| 6,021,340 A | 2/2000 | Randolph et al. |
| 6,022,313 A | 2/2000 | Ginn et al. |
| 6,027,461 A | 2/2000 | Walker et al. |
| 6,027,478 A | 2/2000 | Katz |
| 6,039,699 A | 3/2000 | Viera |
| 6,042,561 A | 3/2000 | Ash et al. |
| 6,048,299 A | 4/2000 | von Hoffmann |
| 6,048,358 A | 4/2000 | Barak |
| 6,053,172 A | 4/2000 | Hovda et al. |
| 6,056,702 A | 5/2000 | Lorenzo |
| 6,059,752 A | 5/2000 | Segal |
| 6,063,022 A | 5/2000 | Ben-Haim |
| 6,063,079 A | 5/2000 | Hovda et al. |
| 6,071,233 A | 6/2000 | Ishikawa et al. |
| 6,079,755 A | 6/2000 | Chang |
| 6,080,190 A | 6/2000 | Schwartz |
| 6,083,148 A | 7/2000 | Williams |
| 6,083,188 A | 7/2000 | Becker |
| 6,086,585 A | 7/2000 | Hovda et al. |
| 6,092,846 A | 7/2000 | Fuss et al. |
| 6,093,150 A | 7/2000 | Chandler et al. |
| 6,093,195 A | 7/2000 | Ouchi |
| 6,102,891 A | 8/2000 | van Erp et al. |
| 6,109,268 A | 8/2000 | Thapliyal et al. |
| 6,112,541 A | 9/2000 | Cosman et al. |
| 6,113,567 A | 9/2000 | becker |
| 6,117,105 A | 9/2000 | Bresnaham et al. |
| 6,123,697 A | 9/2000 | Shippert |
| 6,135,991 A | 10/2000 | Muni et al. |
| 6,136,006 A | 10/2000 | Johnson et al. |
| 6,139,510 A | 10/2000 | Palermo |
| 6,142,957 A | 11/2000 | Diamond et al. |
| 6,146,402 A | 11/2000 | Munoz |
| 6,146,415 A | 11/2000 | Fitz |
| 6,148,823 A | 11/2000 | Hastings |
| 6,149,213 A | 11/2000 | Sokurenko et al. |
| 6,159,170 A | 12/2000 | Borodulin et al. |
| 6,171,298 B1 | 1/2001 | Matsuura et al. |
| 6,171,303 B1 | 1/2001 | Ben-Haim |
| 6,174,280 B1 | 1/2001 | Oneda et al. |
| 6,176,829 B1 | 1/2001 | Vilkomerson |
| 6,179,776 B1 | 1/2001 | Adams et al. |
| 6,179,788 B1 | 1/2001 | Sullivan |
| 6,179,811 B1 | 1/2001 | Fugoso et al. |
| 6,183,433 B1 | 2/2001 | Bays |
| 6,183,461 B1 | 2/2001 | Matsuura et al. |
| 6,183,464 B1 | 2/2001 | Sharp et al. |
| 6,190,353 B1 | 2/2001 | Makower et al. |
| 6,190,381 B1 | 2/2001 | Olsen et al. |
| 6,193,650 B1 | 2/2001 | Ryan, Jr. |
| 6,195,225 B1 | 2/2001 | Komatsu et al. |
| 6,200,257 B1 | 3/2001 | Winkler |
| 6,206,870 B1 | 3/2001 | Kanner |
| 6,206,900 B1 | 3/2001 | Tabatabaei et al. |
| 6,213,975 B1 | 4/2001 | Laksin |
| 6,221,042 B1 | 4/2001 | Adams |
| 6,231,543 B1 | 5/2001 | Hegde et al. |
| 6,234,958 B1 | 5/2001 | Snoke et al. |
| 6,238,364 B1 | 5/2001 | Becker |
| 6,238,391 B1 | 5/2001 | Olsen et al. |
| 6,238,430 B1 | 5/2001 | Klumb et al. |
| 6,241,519 B1 | 6/2001 | Sedleemayer |
| 6,248,092 B1 | 6/2001 | Miraki et al. |
| 6,249,180 B1 | 6/2001 | Maalej et al. |
| 6,254,550 B1 | 7/2001 | McNamara et al. |
| 6,264,087 B1 | 7/2001 | Whitman |
| 6,268,574 B1 | 7/2001 | Edens |
| 6,270,477 B1 | 8/2001 | Bagaoisan et al. |
| 6,280,433 B1 | 8/2001 | McIvor et al. |
| 6,283,908 B1 | 8/2001 | Aviram et al. |
| 6,290,689 B1 | 9/2001 | Delaney et al. |
| 6,293,957 B1 | 9/2001 | Peters et al. |
| 6,295,990 B1 | 10/2001 | Lewis et al. |
| 6,302,875 B1 | 10/2001 | Makower et al. |
| 6,304,768 B1 | 10/2001 | Blume et al. |
| 6,306,105 B1 | 10/2001 | Rooney et al. |
| 6,306,124 B1 | 10/2001 | Jones et al. |
| D450,382 S | 11/2001 | Nestenborg |
| 6,322,495 B1 | 11/2001 | Snow et al. |
| 6,328,564 B1 | 12/2001 | Thurow |
| 6,328,730 B1 | 12/2001 | Harkrider, Jr. |
| 6,332,089 B1 | 12/2001 | Acker et al. |
| 6,332,891 B1 | 12/2001 | Himes |
| 6,340,360 B1 | 1/2002 | Lyles et al. |
| 6,344,028 B1 | 2/2002 | Barry |
| 6,348,041 B1 | 2/2002 | Klint |
| 6,352,503 B1 | 3/2002 | Matsui et al. |
| 6,364,856 B1 | 4/2002 | Ding et al. |
| 6,375,615 B1 | 4/2002 | Flaherty et al. |
| 6,375,629 B1 | 4/2002 | Muni et al. |
| 6,379,319 B1 | 4/2002 | Garibotto et al. |
| 6,381,485 B1 | 4/2002 | Hunter et al. |
| 6,383,146 B1 | 5/2002 | Klint |
| 6,386,197 B1 | 5/2002 | Miller |
| 6,389,313 B1 | 5/2002 | Marchitto et al. |
| 6,390,993 B1 | 5/2002 | Cornish et al. |
| 6,394,093 B1 | 5/2002 | Lethi |
| 6,398,758 B1 | 6/2002 | Jacobsen et al. |
| 6,409,863 B1 | 6/2002 | Williams et al. |
| 6,419,653 B2 | 7/2002 | Edwards et al. |
| 6,423,012 B1 | 7/2002 | Kato et al. |
| 6,425,877 B1 | 7/2002 | Edwards |
| 6,432,986 B2 | 8/2002 | Levin |
| 6,436,119 B1 | 8/2002 | Erb et al. |
| 6,440,061 B1 | 8/2002 | Wenner et al. |
| 6,443,947 B1 | 9/2002 | Marko et al. |
| 6,445,939 B1 | 9/2002 | Swanson et al. |
| 6,450,975 B1 | 9/2002 | Brennan et al. |
| 6,450,989 B2 | 9/2002 | Dubrul et al. |
| 6,464,650 B2 | 10/2002 | Jafari et al. |
| 6,468,202 B1 | 10/2002 | Irion et al. |
| 6,468,297 B1 | 10/2002 | Williams et al. |
| 6,485,475 B1 | 11/2002 | Chelly |

(56) References Cited

U.S. PATENT DOCUMENTS

| | | | |
|---|---|---|---|
| 6,488,653 B1 | 12/2002 | Lombardo | |
| 6,491,940 B1 * | 12/2002 | Levin | A61K 31/445 424/434 |
| 6,494,894 B2 | 12/2002 | Mirarchi | |
| 6,500,130 B2 | 12/2002 | Kinsella et al. | |
| 6,500,189 B1 | 12/2002 | Lang et al. | |
| 6,503,087 B1 | 1/2003 | Eggert et al. | |
| 6,503,185 B1 | 1/2003 | Waksman et al. | |
| 6,503,263 B2 | 1/2003 | Adams | |
| 6,511,418 B2 | 1/2003 | Shahidi et al. | |
| 6,511,471 B2 | 1/2003 | Rosenman et al. | |
| 6,514,249 B1 | 2/2003 | Maguire et al. | |
| 6,517,478 B2 | 2/2003 | Khadem | |
| 6,520,954 B2 | 2/2003 | Ouchi | |
| 6,524,129 B2 | 2/2003 | Cote et al. | |
| 6,524,299 B1 | 2/2003 | Tran et al. | |
| 6,526,302 B2 | 2/2003 | Hassett | |
| 6,527,753 B2 | 3/2003 | Sekine et al. | |
| 6,529,756 B1 | 3/2003 | Phan et al. | |
| 6,533,754 B1 | 3/2003 | Hisamatsu et al. | |
| 6,536,437 B1 | 3/2003 | Dragisic | |
| 6,537,294 B1 | 3/2003 | Boyle et al. | |
| 6,543,452 B1 | 4/2003 | Lavigne | |
| 6,544,223 B1 | 4/2003 | Kokish | |
| 6,544,230 B1 | 4/2003 | Flaherty et al. | |
| 6,549,800 B1 | 4/2003 | Atalar et al. | |
| 6,551,239 B2 | 4/2003 | Renner et al. | |
| 6,562,022 B2 | 5/2003 | Hoste et al. | |
| 6,569,146 B1 | 5/2003 | Werner et al. | |
| 6,569,147 B1 | 5/2003 | Evans et al. | |
| 6,571,131 B1 | 5/2003 | Nguyen | |
| 6,572,538 B2 | 6/2003 | Takase | |
| 6,572,590 B1 | 6/2003 | Stevens et al. | |
| 6,579,285 B2 | 6/2003 | Sinofsky | |
| 6,585,639 B1 | 7/2003 | Kotmel et al. | |
| 6,585,717 B1 | 7/2003 | Wittenberger et al. | |
| 6,585,718 B2 | 7/2003 | Hayzelden et al. | |
| 6,585,794 B2 | 7/2003 | Shimoda et al. | |
| 6,589,164 B1 | 7/2003 | Flaherty | |
| 6,589,237 B2 | 7/2003 | Woloszko et al. | |
| 6,591,130 B2 | 7/2003 | Shahidi | |
| 6,596,009 B1 | 7/2003 | Jelic | |
| 6,607,546 B1 | 8/2003 | Murken | |
| 6,610,059 B1 | 8/2003 | West, Jr. | |
| 6,612,999 B2 | 9/2003 | Brennan et al. | |
| 6,613,066 B1 | 9/2003 | Fukaya et al. | |
| 6,616,601 B2 | 9/2003 | Hayakawa | |
| 6,616,659 B1 | 9/2003 | de la Torre et al. | |
| 6,616,678 B2 | 9/2003 | Nishtala et al. | |
| 6,616,913 B1 | 9/2003 | Mautone | |
| 6,619,085 B1 | 9/2003 | Hsieh | |
| 6,634,684 B2 | 10/2003 | Spiessl | |
| 6,638,233 B2 | 10/2003 | Corvi et al. | |
| 6,638,268 B2 | 10/2003 | Niazi | |
| 6,638,291 B1 | 10/2003 | Ferrera et al. | |
| 6,645,193 B2 | 11/2003 | Mangosong | |
| 6,645,223 B2 | 11/2003 | Boyle et al. | |
| 6,652,472 B2 | 11/2003 | Jafari et al. | |
| 6,652,480 B1 | 11/2003 | Imran et al. | |
| 6,656,166 B2 | 12/2003 | Lurie et al. | |
| 6,659,106 B1 | 12/2003 | Hovda et al. | |
| 6,663,589 B1 | 12/2003 | Halevy | |
| 6,669,689 B2 | 12/2003 | Lehmann et al. | |
| 6,669,711 B1 | 12/2003 | Noda | |
| 6,672,773 B1 | 1/2004 | Glenn et al. | |
| 6,673,025 B1 | 1/2004 | Richardson et al. | |
| 6,679,833 B2 | 1/2004 | Smith et al. | |
| 6,679,871 B2 | 1/2004 | Hahnen | |
| 6,685,648 B2 | 2/2004 | Flaherty et al. | |
| 6,689,096 B1 | 2/2004 | Loubens et al. | |
| 6,689,146 B1 | 2/2004 | Himes | |
| 6,702,735 B2 | 3/2004 | Kelly | |
| 6,706,010 B1 | 3/2004 | Miki et al. | |
| 6,712,757 B2 | 3/2004 | Becker et al. | |
| 6,714,809 B2 | 3/2004 | Lee et al. | |
| 6,716,183 B2 | 4/2004 | Clayman et al. | |
| 6,716,216 B1 | 4/2004 | Boucher et al. | |
| 6,716,813 B2 | 4/2004 | Lim et al. | |
| 6,719,749 B1 | 4/2004 | Schweikert et al. | |
| 6,719,763 B2 | 4/2004 | Chung et al. | |
| 6,726,701 B2 | 4/2004 | Gilson et al. | |
| 6,738,656 B1 | 5/2004 | Ferre et al. | |
| 6,740,191 B2 | 5/2004 | Clarke et al. | |
| 6,741,884 B1 | 5/2004 | Freeman et al. | |
| 6,743,168 B2 | 6/2004 | Luloh et al. | |
| 6,755,812 B2 | 6/2004 | Peterson et al. | |
| 6,758,857 B2 | 7/2004 | Cioanta et al. | |
| 6,776,772 B1 | 8/2004 | de Vrijer et al. | |
| 6,780,168 B2 | 8/2004 | Jellie | |
| 6,783,522 B2 | 8/2004 | Fischell | |
| 6,783,536 B2 | 8/2004 | Vilsmeier et al. | |
| 6,786,864 B2 | 9/2004 | Matsuura et al. | |
| 6,796,960 B2 | 9/2004 | Cioanta et al. | |
| 6,811,544 B2 | 11/2004 | Schaer | |
| 6,817,364 B2 | 11/2004 | Garibaldi et al. | |
| 6,817,976 B2 | 11/2004 | Rovegno | |
| 6,827,683 B2 | 12/2004 | Otawara | |
| 6,827,701 B2 | 12/2004 | MacMahon et al. | |
| 6,832,715 B2 | 12/2004 | Eungard et al. | |
| D501,677 S | 2/2005 | Becker | |
| 6,849,062 B2 | 2/2005 | Kantor | |
| 6,851,290 B1 | 2/2005 | Meier et al. | |
| 6,855,136 B2 | 2/2005 | Dorros et al. | |
| 6,860,264 B2 | 3/2005 | Christopher | |
| 6,860,849 B2 | 3/2005 | Matsushita et al. | |
| 6,866,669 B2 | 3/2005 | Buzzard et al. | |
| 6,878,106 B1 | 4/2005 | Herrmann | |
| 6,890,329 B2 | 5/2005 | Carroll et al. | |
| 6,899,672 B2 | 5/2005 | Chin et al. | |
| 6,902,556 B2 | 6/2005 | Grimes et al. | |
| 6,913,763 B2 | 7/2005 | Lerner | |
| 6,927,478 B2 | 8/2005 | Paek | |
| 6,939,361 B1 | 9/2005 | Kleshinski | |
| 6,939,374 B2 | 9/2005 | Banik et al. | |
| 6,953,431 B2 | 10/2005 | Barthel | |
| 6,955,657 B1 | 10/2005 | Webler | |
| 6,966,906 B2 | 11/2005 | Brown | |
| 6,971,998 B2 | 12/2005 | Rosenman et al. | |
| 6,979,290 B2 | 12/2005 | Mourlas et al. | |
| 6,979,979 B2 | 12/2005 | Xu et al. | |
| 6,984,203 B2 | 1/2006 | Tartaglia et al. | |
| 6,989,024 B2 | 1/2006 | Hebert et al. | |
| 6,991,597 B2 | 1/2006 | Gellman et al. | |
| 6,997,931 B2 | 2/2006 | Sauer et al. | |
| 6,997,941 B2 | 2/2006 | Sharkey et al. | |
| 7,004,173 B2 | 2/2006 | Sparks et al. | |
| 7,004,176 B2 | 2/2006 | Lau | |
| 7,008,412 B2 | 3/2006 | Maginot | |
| 7,011,654 B2 | 3/2006 | Dubrul et al. | |
| 7,022,105 B1 | 4/2006 | Edwards | |
| 7,037,321 B2 | 5/2006 | Sachdeva et al. | |
| 7,043,961 B2 | 5/2006 | Pandey et al. | |
| 7,044,964 B2 | 5/2006 | Jang et al. | |
| 7,048,711 B2 | 5/2006 | Rosenman et al. | |
| 7,052,474 B2 | 5/2006 | Castell et al. | |
| 7,056,284 B2 | 6/2006 | Martone et al. | |
| 7,056,287 B2 | 6/2006 | Taylor et al. | |
| 7,056,303 B2 | 6/2006 | Dennis et al. | |
| 7,056,314 B1 | 6/2006 | Florio et al. | |
| 7,074,197 B2 | 7/2006 | Reynolds et al. | |
| 7,074,426 B2 | 7/2006 | Kochinke | |
| 7,097,612 B2 | 8/2006 | Bertolero et al. | |
| 7,108,677 B2 | 9/2006 | Courtney et al. | |
| 7,108,706 B2 | 9/2006 | Hogle | |
| 7,117,039 B2 | 10/2006 | Manning et al. | |
| 7,128,718 B2 | 10/2006 | Hojeibane et al. | |
| 7,131,969 B1 | 11/2006 | Hovda et al. | |
| 7,140,480 B2 | 11/2006 | Drussel et al. | |
| D534,216 S | 12/2006 | Makower et al. | |
| 7,160,255 B2 | 1/2007 | Saadat | |
| 7,169,140 B1 | 1/2007 | Kume | |
| 7,169,163 B2 | 1/2007 | Becker | |
| 7,172,562 B2 | 2/2007 | McKinley | |
| 7,174,774 B2 | 2/2007 | Pawar et al. | |

(56) References Cited

U.S. PATENT DOCUMENTS

| | | |
|---|---|---|
| 7,182,735 B2 | 2/2007 | Shireman et al. |
| 7,184,827 B1 | 2/2007 | Edwards |
| 7,186,224 B2 | 3/2007 | Windheuser |
| 7,207,981 B2 | 4/2007 | Quinn et al. |
| 7,214,201 B2 | 5/2007 | Burmeister et al. |
| 7,233,820 B2 | 6/2007 | Gilboa |
| 7,235,099 B1 | 6/2007 | Duncavage et al. |
| 7,237,313 B2 | 7/2007 | Skujins et al. |
| 7,248,914 B2 | 7/2007 | Hastings et al. |
| 7,252,677 B2 | 8/2007 | Burwell et al. |
| 7,282,057 B2 | 10/2007 | Surti et al. |
| 7,292,885 B2 | 11/2007 | Scott et al. |
| 7,294,345 B2 | 11/2007 | Haapakumpu et al. |
| 7,294,365 B2 | 11/2007 | Hayakawa et al. |
| 7,303,533 B2 | 12/2007 | Johansen et al. |
| 7,309,334 B2 | 12/2007 | von Hoffmann |
| 7,313,430 B2 | 12/2007 | Urquhart et al. |
| 7,316,168 B2 | 1/2008 | van der Knokke et al. |
| 7,316,656 B2 | 1/2008 | Shireman et al. |
| 7,318,831 B2 | 1/2008 | Alvarez et al. |
| 7,322,934 B2 | 1/2008 | Miyake et al. |
| 7,326,235 B2 | 2/2008 | Edwards |
| 7,338,467 B2 | 3/2008 | Lutter |
| 7,343,920 B2 | 3/2008 | Toby et al. |
| 7,347,868 B2 | 3/2008 | Burnett et al. |
| 7,359,755 B2 | 4/2008 | Jones et al. |
| 7,361,168 B2 | 4/2008 | Makower et al. |
| 7,366,562 B2 | 4/2008 | Dukesherer |
| 7,371,210 B2 | 5/2008 | Brock et al. |
| 7,381,205 B2 | 6/2008 | Thommen |
| 7,384,407 B2 | 6/2008 | Rodriguez et al. |
| 7,410,480 B2 | 8/2008 | Muni et al. |
| 7,419,497 B2 | 9/2008 | Muni et al. |
| 7,438,701 B2 | 10/2008 | Theeuwes et al. |
| 7,442,191 B2 | 10/2008 | Hovda et al. |
| 7,452,351 B2 | 11/2008 | Miller et al. |
| 7,454,244 B2 | 11/2008 | Kassab et al. |
| 7,462,175 B2 | 12/2008 | Chang et al. |
| 7,471,994 B2 | 12/2008 | Ford et al. |
| 7,481,218 B2 | 1/2009 | Djupesland |
| 7,481,800 B2 | 1/2009 | Jacques |
| D586,465 S | 2/2009 | Faulkner et al. |
| D586,916 S | 2/2009 | Faulkner et al. |
| 7,488,313 B2 | 2/2009 | Segal et al. |
| 7,488,337 B2 | 2/2009 | Saab et al. |
| 7,493,156 B2 | 2/2009 | Manning et al. |
| 7,500,971 B2 | 3/2009 | Chang et al. |
| D590,502 S | 4/2009 | Geisser et al. |
| 7,520,876 B2 | 4/2009 | Ressemann et al. |
| 7,532,920 B1 | 5/2009 | Ainsworth et al. |
| 7,544,192 B2 | 6/2009 | Eaton et al. |
| 7,551,758 B2 | 6/2009 | Florent et al. |
| 7,559,925 B2 | 7/2009 | Goldfarb et al. |
| 7,566,300 B2 | 7/2009 | Devierre et al. |
| 7,610,104 B2 | 10/2009 | Kaplan et al. |
| 7,615,005 B2 | 11/2009 | Stefanchik et al. |
| 7,618,450 B2 | 11/2009 | Zarowski et al. |
| 7,625,335 B2 | 12/2009 | Deichmann et al. |
| 7,632,291 B2 | 12/2009 | Stephens et al. |
| 7,634,233 B2 | 12/2009 | Deng et al. |
| 7,641,644 B2 | 1/2010 | Chang et al. |
| 7,641,668 B2 | 1/2010 | Perry et al. |
| 7,645,272 B2 | 1/2010 | Chang et al. |
| 7,648,367 B1 | 1/2010 | Makower et al. |
| 7,648,517 B2 | 1/2010 | Makower et al. |
| 7,654,997 B2 | 2/2010 | Makower et al. |
| 7,680,244 B2 | 3/2010 | Gertner et al. |
| 7,686,798 B2 | 3/2010 | Eaton et al. |
| 7,691,120 B2 | 4/2010 | Shluzas et al. |
| 7,697,972 B2 | 4/2010 | Verard et al. |
| 7,717,933 B2 | 5/2010 | Becker |
| 7,720,521 B2 | 5/2010 | Chang et al. |
| 7,727,186 B2 | 6/2010 | Makower et al. |
| 7,727,226 B2 | 6/2010 | Chang et al. |
| 7,736,301 B1 | 6/2010 | Webler et al. |
| 7,740,642 B2 | 6/2010 | Becker |
| 7,751,758 B2 | 7/2010 | Yahagi |
| 7,753,929 B2 | 7/2010 | Becker |
| 7,753,930 B2 | 7/2010 | Becker |
| 7,758,497 B2 | 7/2010 | Hern |
| 7,771,409 B2 | 8/2010 | Chang et al. |
| 7,775,968 B2 | 8/2010 | Mathis |
| 7,785,315 B1 | 8/2010 | Muni et al. |
| 7,799,048 B2 | 9/2010 | Hudson et al. |
| 7,799,337 B2 | 9/2010 | Levin |
| 7,803,150 B2 | 9/2010 | Chang et al. |
| 7,833,282 B2 | 11/2010 | Mandpe |
| 7,837,672 B2 | 11/2010 | Intoccia |
| 7,840,254 B2 | 11/2010 | Glossop |
| 7,854,744 B2 | 12/2010 | Becker |
| 7,857,750 B2 | 12/2010 | Belafsky |
| D630,321 S | 1/2011 | Hamilton, Jr. |
| 7,875,050 B2 | 1/2011 | Samson et al. |
| D632,791 S | 2/2011 | Murner |
| 7,881,769 B2 | 2/2011 | Sobe |
| 7,883,717 B2 | 2/2011 | Varner et al. |
| 7,896,891 B2 | 3/2011 | Catanese, III et al. |
| 7,927,271 B2 | 4/2011 | Dimitriou et al. |
| 7,951,132 B2 | 5/2011 | Eaton et al. |
| 7,988,705 B2 | 8/2011 | Galdonik et al. |
| 7,993,353 B2 | 8/2011 | Roβner et al. |
| 8,002,740 B2 | 8/2011 | Willink et al. |
| 8,014,849 B2 | 9/2011 | Peckham |
| 8,016,752 B2 | 9/2011 | Armstrong et al. |
| 8,025,635 B2 | 9/2011 | Eaton et al. |
| 8,075,476 B2 | 12/2011 | Vargas |
| 8,075,478 B2 | 12/2011 | Campos |
| 8,080,000 B2 | 12/2011 | Makower et al. |
| 8,088,063 B2 | 1/2012 | Fujikura et al. |
| 8,088,101 B2 | 1/2012 | Chang et al. |
| 8,090,433 B2 | 1/2012 | Makower et al. |
| 8,100,933 B2 | 1/2012 | Becker |
| 8,104,483 B2 | 1/2012 | Taylor |
| 8,114,062 B2 | 2/2012 | Muni et al. |
| 8,114,113 B2 | 2/2012 | Becker |
| 8,123,722 B2 | 2/2012 | Chang et al. |
| 8,142,422 B2 | 3/2012 | Makower et al. |
| 8,146,400 B2 | 4/2012 | Goldfarb et al. |
| 8,147,545 B2 | 4/2012 | Avior |
| 8,167,821 B2 | 5/2012 | Sharrow |
| 8,172,828 B2 | 5/2012 | Chang et al. |
| 8,190,389 B2 | 5/2012 | Kim et al. |
| 8,197,433 B2 | 6/2012 | Cohen |
| 8,197,552 B2 | 6/2012 | Mandpe |
| 8,249,700 B2 | 8/2012 | Clifford et al. |
| 8,277,386 B2 | 10/2012 | Ahmed et al. |
| 8,317,816 B2 | 11/2012 | Becker |
| 8,337,454 B2 | 12/2012 | Eaton et al. |
| 8,388,642 B2 | 3/2013 | Muni et al. |
| 8,403,954 B2 | 3/2013 | Santin et al. |
| 8,414,473 B2 | 4/2013 | Jenkins et al. |
| 8,425,457 B2 | 4/2013 | John et al. |
| 8,439,687 B1 | 5/2013 | Morriss et al. |
| 8,475,360 B2 | 7/2013 | Brown |
| 8,521,259 B2 | 8/2013 | Mandrusov et al. |
| 8,529,439 B2 | 9/2013 | Ito et al. |
| 8,535,707 B2 | 9/2013 | Arensdorf et al. |
| 8,702,626 B1 | 4/2014 | Kim et al. |
| 8,715,169 B2 | 5/2014 | Chang et al. |
| 8,721,591 B2 | 5/2014 | Chang et al. |
| 8,740,839 B2 | 6/2014 | Eaton et al. |
| 8,740,929 B2 | 6/2014 | Gopferich et al. |
| 8,747,389 B2 | 6/2014 | Goldfarb et al. |
| 8,764,709 B2 | 7/2014 | Chang et al. |
| 8,764,726 B2 | 7/2014 | Chang et al. |
| 8,764,729 B2 | 7/2014 | Muni et al. |
| 8,777,926 B2 | 7/2014 | Chang et al. |
| 8,802,131 B2 | 8/2014 | Arensdorf et al. |
| 8,828,041 B2 | 9/2014 | Chang et al. |
| 2001/0004644 A1 | 6/2001 | Levin |
| 2001/0005785 A1 | 6/2001 | Sachse |
| 2001/0034530 A1 | 10/2001 | Malackowski et al. |
| 2002/0006961 A1 | 1/2002 | Katz et al. |
| 2002/0013548 A1 | 1/2002 | Hinchliffe |

(56) References Cited

U.S. PATENT DOCUMENTS

| | | |
|---|---|---|
| 2002/0055746 A1 | 5/2002 | Burke et al. |
| 2002/0068851 A1 | 6/2002 | Gravenstein et al. |
| 2002/0077593 A1 | 6/2002 | Perkins et al. |
| 2002/0090388 A1 | 7/2002 | Humes et al. |
| 2002/0161389 A1 | 10/2002 | Boyle et al. |
| 2003/0009095 A1 | 1/2003 | Skarda |
| 2003/0013985 A1 | 1/2003 | Saadat |
| 2003/0017111 A1 | 1/2003 | Rabito |
| 2003/0018291 A1 | 1/2003 | Hill et al. |
| 2003/0040697 A1 | 2/2003 | Pass et al. |
| 2003/0051733 A1 | 3/2003 | Kotmel et al. |
| 2003/0073900 A1 | 4/2003 | Senarith et al. |
| 2003/0074045 A1 | 4/2003 | Buzzard et al. |
| 2003/0083608 A1 | 5/2003 | Evans et al. |
| 2003/0114732 A1 | 6/2003 | Webler et al. |
| 2003/0163154 A1 | 8/2003 | Miyata et al. |
| 2003/0167060 A1 | 9/2003 | Buzzard et al. |
| 2003/0171650 A1* | 9/2003 | Tartaglia ............ A61B 1/00147 600/114 |
| 2003/0220551 A1 | 11/2003 | Kimball et al. |
| 2004/0015150 A1 | 1/2004 | Zadno-Azizi |
| 2004/0018980 A1 | 1/2004 | Gurney et al. |
| 2004/0020492 A1 | 2/2004 | Dubrul et al. |
| 2004/0034311 A1 | 2/2004 | Mihakcik |
| 2004/0043052 A1 | 3/2004 | Hunter et al. |
| 2004/0058992 A1 | 3/2004 | Marinello et al. |
| 2004/0064105 A1 | 4/2004 | Capes et al. |
| 2004/0064150 A1* | 4/2004 | Becker .................. A61B 17/32 606/196 |
| 2004/0116958 A1 | 6/2004 | Gopferich et al. |
| 2004/0127820 A1 | 7/2004 | Clayman et al. |
| 2004/0158229 A1 | 8/2004 | Quinn |
| 2004/0181175 A1 | 9/2004 | Clayman et al. |
| 2004/0193073 A1 | 9/2004 | DeMello et al. |
| 2004/0220516 A1 | 11/2004 | Solomon et al. |
| 2004/0230156 A1 | 11/2004 | Schreck et al. |
| 2004/0236231 A1 | 11/2004 | Knighton et al. |
| 2004/0249243 A1 | 12/2004 | Kleiner |
| 2004/0267347 A1 | 12/2004 | Cervantes |
| 2005/0027249 A1 | 2/2005 | Reifart et al. |
| 2005/0038319 A1 | 2/2005 | Goldwasser et al. |
| 2005/0055077 A1 | 3/2005 | Marco |
| 2005/0059930 A1 | 3/2005 | Garrison et al. |
| 2005/0059931 A1 | 3/2005 | Garrison et al. |
| 2005/0089670 A1 | 4/2005 | Large |
| 2005/0107738 A1 | 5/2005 | Slater et al. |
| 2005/0113687 A1 | 5/2005 | Herweck et al. |
| 2005/0113850 A1 | 5/2005 | Tagge |
| 2005/0119590 A1 | 6/2005 | Burmeister et al. |
| 2005/0124856 A1 | 6/2005 | Fujikura et al. |
| 2005/0131316 A1 | 6/2005 | Flagle et al. |
| 2005/0143687 A1 | 6/2005 | Rosenblatt et al. |
| 2005/0182319 A1 | 8/2005 | Glossop |
| 2005/0228224 A1 | 10/2005 | Okada et al. |
| 2005/0234507 A1 | 10/2005 | Geske et al. |
| 2005/0240120 A1 | 10/2005 | Modesitt |
| 2005/0244472 A1 | 11/2005 | Hughes et al. |
| 2005/0283221 A1 | 12/2005 | Mann et al. |
| 2006/0004323 A1 | 1/2006 | Chang et al. |
| 2006/0047261 A1 | 3/2006 | Joshi |
| 2006/0063973 A1 | 3/2006 | Makower et al. |
| 2006/0173382 A1 | 8/2006 | Schreiner |
| 2006/0189844 A1 | 8/2006 | Tien |
| 2006/0190022 A1 | 8/2006 | Beyar et al. |
| 2006/0211752 A1 | 9/2006 | Kohn et al. |
| 2006/0271024 A1 | 11/2006 | Gertner et al. |
| 2006/0284428 A1 | 12/2006 | Beadle et al. |
| 2007/0020196 A1 | 1/2007 | Pipkin et al. |
| 2007/0112358 A1 | 5/2007 | Abbott |
| 2007/0129751 A1 | 6/2007 | Muni et al. |
| 2007/0135789 A1 | 6/2007 | Chang et al. |
| 2007/0167682 A1 | 7/2007 | Goldfarb et al. |
| 2007/0207186 A1 | 9/2007 | Scanlon et al. |
| 2007/0208252 A1 | 9/2007 | Makower |
| 2007/0208301 A1 | 9/2007 | Evard et al. |
| 2007/0249896 A1 | 10/2007 | Goldfarb et al. |
| 2007/0269385 A1 | 11/2007 | Yun et al. |
| 2007/0282305 A1 | 12/2007 | Goldfarb et al. |
| 2007/0293727 A1 | 12/2007 | Goldfarb et al. |
| 2007/0293946 A1 | 12/2007 | Gonzales et al. |
| 2008/0015544 A1 | 1/2008 | Keith et al. |
| 2008/0033519 A1 | 2/2008 | Burwell et al. |
| 2008/0051804 A1 | 2/2008 | Cottler et al. |
| 2008/0097516 A1 | 4/2008 | Chang et al. |
| 2008/0103521 A1 | 5/2008 | Makower et al. |
| 2008/0119693 A1 | 5/2008 | Makower et al. |
| 2008/0125626 A1 | 5/2008 | Chang et al. |
| 2008/0132938 A1 | 6/2008 | Chang et al. |
| 2008/0172033 A1 | 7/2008 | Keith et al. |
| 2008/0183128 A1 | 7/2008 | Morriss et al. |
| 2008/0188803 A1 | 8/2008 | Jang |
| 2008/0188870 A1 | 8/2008 | Andre et al. |
| 2008/0195041 A1 | 8/2008 | Goldfarb et al. |
| 2008/0228085 A1 | 9/2008 | Jenkins et al. |
| 2008/0262508 A1 | 10/2008 | Clifford et al. |
| 2008/0275483 A1 | 11/2008 | Makower et al. |
| 2008/0281156 A1 | 11/2008 | Makower et al. |
| 2008/0287908 A1 | 11/2008 | Muni et al. |
| 2008/0319424 A1 | 12/2008 | Muni et al. |
| 2009/0030274 A1 | 1/2009 | Goldfarb et al. |
| 2009/0088728 A1 | 4/2009 | Dollar et al. |
| 2009/0156980 A1 | 6/2009 | Eaton et al. |
| 2009/0163890 A1 | 6/2009 | Clifford et al. |
| 2009/0187089 A1 | 7/2009 | Say et al. |
| 2009/0187098 A1 | 7/2009 | Makower et al. |
| 2009/0198216 A1 | 8/2009 | Muni et al. |
| 2009/0240112 A1 | 9/2009 | Goldfarb et al. |
| 2009/0240237 A1 | 9/2009 | Goldfarb et al. |
| 2009/0312745 A1 | 12/2009 | Goldfarb et al. |
| 2010/0030031 A1 | 2/2010 | Goldfarb et al. |
| 2010/0042046 A1 | 2/2010 | Chang et al. |
| 2010/0087811 A1 | 4/2010 | Herrin et al. |
| 2010/0114066 A1 | 5/2010 | Makower et al. |
| 2010/0174138 A1 | 7/2010 | Chang et al. |
| 2010/0174308 A1 | 7/2010 | Chang et al. |
| 2010/0198191 A1 | 8/2010 | Clifford et al. |
| 2010/0198247 A1 | 8/2010 | Chang et al. |
| 2010/0198302 A1 | 8/2010 | Shalev |
| 2010/0210901 A1 | 8/2010 | Makower et al. |
| 2010/0211007 A1 | 8/2010 | Lesch, Jr. et al. |
| 2010/0268245 A1 | 10/2010 | Chang et al. |
| 2010/0274188 A1 | 10/2010 | Chang et al. |
| 2010/0290244 A1 | 11/2010 | Nath |
| 2010/0298862 A1 | 11/2010 | Chang et al. |
| 2011/0004057 A1 | 1/2011 | Goldfarb et al. |
| 2011/0015482 A1 | 1/2011 | Carrillo, Jr. |
| 2011/0060214 A1 | 3/2011 | Makower |
| 2011/0112512 A1 | 5/2011 | Muni et al. |
| 2011/0166190 A1 | 7/2011 | Anderson et al. |
| 2012/0071710 A1 | 3/2012 | Gazdzinski |
| 2012/0071824 A1 | 3/2012 | Chang et al. |
| 2012/0136207 A1 | 5/2012 | Goldfarb et al. |
| 2012/0184983 A1 | 7/2012 | Chang et al. |
| 2012/0245419 A1 | 9/2012 | Makower et al. |
| 2012/0265094 A1 | 10/2012 | Goldfarb et al. |
| 2013/0231529 A1 | 9/2013 | Chang et al. |
| 2013/0245608 A1 | 9/2013 | Muni et al. |
| 2013/0261388 A1 | 10/2013 | Jenkins et al. |
| 2015/0088188 A1 | 3/2015 | Muni et al. |
| 2015/0165175 A1 | 6/2015 | Evard et al. |
| 2015/0165176 A1 | 6/2015 | Makower et al. |
| 2015/0182735 A1 | 7/2015 | Chang et al. |
| 2015/0209055 A1 | 7/2015 | Chang et al. |
| 2015/0250992 A1 | 9/2015 | Morriss et al. |
| 2016/0192830 A1 | 7/2016 | Goldfarb et al. |
| 2016/0270863 A1 | 9/2016 | Makower |

FOREIGN PATENT DOCUMENTS

| | | |
|---|---|---|
| CN | 2151720 | 1/1994 |
| CN | 2352818 | 12/1999 |
| CN | 201005758 Y | 1/2008 |
| DE | 3202878 | 8/1983 |
| DE | 4032096 | 4/1992 |

(56) References Cited

FOREIGN PATENT DOCUMENTS

| | | |
|---|---|---|
| DE | 4406077 | 9/1994 |
| DE | 8810044 | 11/1998 |
| DE | 29923582 | 12/2000 |
| DE | 10104663 | 8/2002 |
| DE | 10105592 | 8/2002 |
| EP | 129634 | 1/1985 |
| EP | 0200430 | 11/1986 |
| EP | 257605 | 3/1988 |
| EP | 355996 | 2/1990 |
| EP | 418391 | 3/1991 |
| EP | 427852 | 5/1991 |
| EP | 0515201 | 11/1992 |
| EP | 623582 | 11/1994 |
| EP | 624349 | 11/1994 |
| EP | 744400 | 11/1996 |
| EP | 585757 | 6/1997 |
| EP | 893426 | 1/1999 |
| EP | 0920882 | 6/1999 |
| EP | 0974936 | 1/2000 |
| EP | 1042998 | 10/2000 |
| EP | 1086664 | 3/2001 |
| EP | 1112103 | 7/2001 |
| EP | 1166710 | 1/2002 |
| EP | 1413258 | 4/2004 |
| EP | 1944053 | 7/2008 |
| FR | 2662083 | 11/1991 |
| FR | 2859377 | 3/2005 |
| FR | 2916144 | 11/2008 |
| GB | 2125874 | 3/1984 |
| GB | 2305174 | 4/1997 |
| JP | 53-67935 | 6/1978 |
| JP | S61-16750 | 1/1986 |
| JP | 10-24098 | 1/1989 |
| JP | 10-034376 | 2/1989 |
| JP | H10-034376 | 2/1989 |
| JP | H01-305965 | 12/1989 |
| JP | 3-503011 | 7/1991 |
| JP | 3-504935 | 10/1991 |
| JP | 4-221313 | 8/1992 |
| JP | 4-224766 | 8/1992 |
| JP | H5-503650 | 6/1993 |
| JP | 5-211985 | 8/1993 |
| JP | H05-506805 | 10/1993 |
| JP | 06-17751 | 3/1994 |
| JP | 6-277296 | 10/1994 |
| JP | 7-327916 | 12/1995 |
| JP | 8-317989 | 12/1996 |
| JP | H10-501159 | 2/1998 |
| JP | H10-94543 | 4/1998 |
| JP | 11-507251 | 6/1999 |
| JP | 2000-501634 | 2/2000 |
| JP | 2000-126303 | 5/2000 |
| JP | 2001-025508 | 1/2001 |
| JP | 2001-501846 | 2/2001 |
| JP | 2001-095815 | 4/2001 |
| JP | 2001-526077 | 12/2001 |
| JP | 2002-028166 | 1/2002 |
| JP | 2002-508214 | 3/2002 |
| JP | 2002-537908 | 11/2002 |
| JP | 2002-538850 | 11/2002 |
| JP | 2003-507140 | 2/2003 |
| JP | 2003-062080 | 3/2003 |
| JP | 2003-521327 | 7/2003 |
| JP | 2004-049583 | 2/2004 |
| JP | 2004-357728 | 12/2004 |
| JP | 2005-323702 | 11/2005 |
| JP | 2005-532869 | 11/2005 |
| JP | 2008-539031 | 11/2008 |
| RU | 2108764 | 4/1998 |
| RU | 2213530 | 10/2003 |
| SU | 1662571 | 7/1991 |
| WO | WO 90/011053 | 10/1990 |
| WO | WO 90/014865 | 12/1990 |
| WO | WO 91/017787 | 11/1991 |
| WO | WO 92/015286 | 9/1992 |
| WO | WO 92/022350 | 12/1992 |
| WO | WO 94/012095 | 6/1994 |
| WO | WO 94/021320 | 9/1994 |
| WO | WO 95/002430 | 1/1995 |
| WO | WO 96/029071 | 9/1996 |
| WO | WO 97/021461 | 6/1997 |
| WO | WO 98/055174 | 12/1998 |
| WO | WO 99/000064 | 1/1999 |
| WO | WO 99/024106 | 5/1999 |
| WO | WO 99/026692 | 6/1999 |
| WO | WO 99/030655 | 6/1999 |
| WO | WO 99/032041 | 7/1999 |
| WO | WO 99/059649 | 11/1999 |
| WO | WO 00/009190 | 2/2000 |
| WO | WO 00/009192 | 2/2000 |
| WO | WO 00/023009 | 4/2000 |
| WO | WO 00/051672 | 9/2000 |
| WO | WO 00/053252 | 9/2000 |
| WO | WO 00/067834 | 11/2000 |
| WO | WO 01/005462 | 1/2001 |
| WO | WO 01/045572 | 6/2001 |
| WO | WO 01/054558 | 8/2001 |
| WO | WO 01/056481 | 8/2001 |
| WO | WO 01/068178 | 9/2001 |
| WO | WO 01/070325 | 9/2001 |
| WO | WO 01/074266 | 10/2001 |
| WO | WO 01/082800 | 11/2001 |
| WO | WO 01/097895 | 12/2001 |
| WO | WO 02/062269 | 8/2002 |
| WO | WO 02/089899 | 11/2002 |
| WO | WO 03/049603 | 6/2003 |
| WO | WO 03/063703 | 8/2003 |
| WO | WO 03/105657 | 12/2003 |
| WO | WO 04/006788 | 1/2004 |
| WO | WO 04/018980 | 3/2004 |
| WO | WO 04/026391 | 4/2004 |
| WO | WO 04/045387 | 6/2004 |
| WO | WO 04/058045 | 7/2004 |
| WO | WO 04/082525 | 9/2004 |
| WO | WO 05/018730 | 3/2005 |
| WO | WO 05/077450 | 8/2005 |
| WO | WO 05/089670 | 9/2005 |
| WO | WO 05/117755 | 12/2005 |
| WO | WO 06/034008 | 3/2006 |
| WO | WO 06/078884 | 7/2006 |
| WO | WO 06/107957 | 10/2006 |
| WO | WO 06/116597 | 11/2006 |
| WO | WO 06/118737 | 11/2006 |
| WO | WO 06/135853 | 12/2006 |
| WO | WO 07/034203 | 3/2007 |
| WO | WO 07/035204 | 3/2007 |
| WO | WO 07/111636 | 10/2007 |
| WO | WO 07/124260 | 11/2007 |
| WO | WO 08/036149 | 3/2008 |
| WO | WO 08/045242 | 4/2008 |
| WO | WO 08/051918 | 5/2008 |
| WO | WO 08/134382 | 11/2008 |

OTHER PUBLICATIONS

Aust, R., et al. 'The Functional Size of the Human Maxillary Ostium in Vivo' Acta. Otolaryn. (9178) vol. 78 pp. 432-435.

Baim, D.S., MD 'Grossman's Cardiac Catheterization, Angiography, and Intervention' (2000) Lippincott Williams & Wilkins pp. 76, 84 & 214.

Barrett, S. 'Be Wary of Neurocranial Restructuring (NCR)' Chirobase; Jul. 2003; www.chirobase.org/06DD/ncr.html.

Bartal, N. 'An Improved stent for Use in the Surgical Management of Congential Posterior Choanal Atresia' J. Laryngol. Otol (1988) vol. 102 pp. 146-147.

Becker, A.E. 'Restenosis After Angioplasty' The Lancet (1988) vol. 331, No. 8584 p. 532.

Bellis, M. History of the Catheter-Balloon Catheter-Thomas Fogarty. www.inventors.about.com/library/inventors/blcatheter.htm?p=1.

Benninger et al., Adult Chronic Rhinosinusitis: Definitions, Diagnosis, Epidemiology, and Pathophysilogy' Arch Otolarygol Head and Neck Surg. vol. 129 (Sep. 2003) pp. A1-S32.

(56) References Cited

OTHER PUBLICATIONS

Bent et al. 'The Frontal Cell as a Cause of Frontal Sinus Obstruction' American Journal of Rhinology, vol. 8, No. 4 (1994) pp. 185-191.
Binner et al. 'Fibre-Optic Transillumination of the Sinuses: A Comparison of the Value of Radiography and Transillumination in Antral Disease' Clinical Otolaryngology. vol. 3(1978) pp. 1-11.
Brown, C.L. et al., 'Safety and Feasibility of Balloon Catheter Dilation of Paranasal Sinus Ostia: A Preliminary Investigation' Annals of Otology, Rhinology & Laryngology (2006) vol. 115, No. 4 pp. 293-299.
Casiona et al. 'Endoscopic Lothrop Procedure: The University of Miami Experience' Amencan Journal of Rhinology, vol. 12, No. 5 (1998) pp. 335-339.
Casserly, I.P. et al., Chapter 7. 'Guides and Wires in Percutaneous Coronary Intervention' Strategic Approaches in Coronary Intervention (2006) Lippincott Williams & Wilkins pp. 91-99.
Chien, Y.W. et al. 'Nasal Systemic Drug Delivery'Drugs and Pharmaceutical Sciences, vol. 39, pp. 60-63.
Cohen et al. 'Endoscopic Sinus Surgery: Where we are and where we're going' Current Opinion in Otolaryngology & Head and Neck Surgery, vol. 13 (2005) pp. 32-38.
Colla, A. et al., 'Trihaloacetylated Enol Ethers-General Synthetic Procedure and Heterocyclic Ring Closure Reactions with Hydroxylamine' Synthesis, (Jun. 1991) pp. 483-486.
Costa, M.N. et al. 'Endoscopic Study of the Intranasal Ostium in External Dacryocystorhinostomy Postoperative. Influence of Saline Solution and 5-Flurorouracil' Clinics (2007) vol. 62, Issue1, pp. 41-46.
Cussler, E.L. 'Diffusion: Mass transfer in Fluid Systems' Cambridge University Press (1996).
Davis, G.E. et al. 'A Complication from Neurocranial Restructuring' Arch Otolaryngol Head Neck Surg. vol. 129 (Apr. 2003) pp. 472-474.
Deutschmann, R. et al. 'A Contribution to the Topical Treatment of [Maxillary] Sinusitis Preliminary Communication' Stomat DDR 26, (1976) pp. 585-592.
Domb, A. et al. 'Handbook of Biodegradable Polymers' Hardwood Academic Publishers (1997).
Doyle Nasal Splints, Jan. 25, 2007; www.doylemedical.com/nasalsplints.htm.
Draf, W. 'Endonasal Micro-Endoscopic Frontal Sinus Surgery: the Fulda Concept' Op Tech Otolaryngol Head Neck Surg. vol. 2 (1991) pp. 234-240.
"Durometer Made Easy Durometer Hardness Scales—General Reference Guide." Paramount Industries, Inc. 2008. Accessed online: http//www.paramountind.com/pdfs/paramount_durometer_scale_guide.pdf.
"Durometer Shore Hardness Scale." Smooth-On, Inc. 2016. Accessed online: https://www.smooth-on.com/page/durometer-shore-hardness-scale/.
Edmond, C. et al. 'ENT Surgical Stimulator' Nov. 1989.
ENT Checklist; Physical Examination Performance Checklist [date of publication unknown].
Eremychev, V.A. 'Needles for Puncture and Drainage of the Maxillary Sinus' Meditsinskaya Tekhnika, No. 5 (1974) pp. 54.55.
Feldman, R.L. et al., 'New Steerable, Ultra-Low-Profile, Fixed Wire Angioplasty Catheter: Initial Experience with the Cordis OrionTM Steerable PTCA Balloon Catheter' Cathet. Cardiovasc. Diagn. (1990) vol. 19, No. 2 pp. 142-145.
Ford, C.N. 'A Multipurpose Laryngeal Injector Device' Otolaryngol. Head Neck Surg. (1990) vol. 103, No. 1 pp. 135-137.
Friedman, M., M.D., et al. 'Frontal Sinus Surgery: Endoscopic Technique' Operative Techniques in Otolarynology—Head and Neck Surgery. vol. 12, No. 2 (Jun. 2001) pp. 60-65.
Friedman, et al. 'Intraoperative and Postoperative Assessment of Frontal Sinus Patency by Transillumination' Laryngoscope. vol. 110 (Apr. 2000) pp. 683-684.

Friedman, et al 'Middle Turbinate Medialization and Preservation in Endoscopic Surgery' Otolaryngology—Head and Neck Surgery. (2000) vol. 123, No. 1, part 1, pp. 76-80.
Fung, M.K.T. 'Template for Frontal Osteoplastic Flap' Laryngoscope. vol. 96 (1986) pp. 578-579.
Gatot, A. et al. 'Early treatment of Orbital Floor Fractures with Catheter Balloon in Children' Int J. Pediatric Otorhinolaryngol (1991) vol. 21 pp. 97-101.
Gerus, I.I. et al. 'β-Ethoxyvinyl Polyfluroroalkyl Ketones-Versatile Synthones in Fluoroorganic Chemistry' Journal of Fluorine Chemistry. vol. 69 (1994) pp. 195-198. Elsevier Science S.A.
Good, R.H. 'An Intranasal Method for Opening the Frontal Sinus Establishing the Largest Possible Drainage' Laryngoscope. vol. 18 (1908) pp. 266-274.
Gopferich 'Polymer Degradation and Erosion: Mechanisms and Application' Eur. J. Parm. Biophar. vol. 42 (1996) pp. 1-11.
Gorlov, D.V. et al 'Acylation of Z-Methoxypropene with Anhydrides and Halides of Perflurocarboxylic Acids in the Presence of Teriary Amines' Russian Chemical Bulletin. vol. 48 No. 9 (Sep. 1999) pp. 1791-1792. Kluwer Academic/Plenum Publishers.
Gottmann, et al. 'Balloon Dilatation in the Nasal Cavity and Paranasal Sinuses' CIRSE. (Sep. 25, 2004) pp. 1-27.
Gottmann, et al. 'Balloon Dilatation of Recurrent Ostial Occlusion of the Frontal Sinus' CIRSE Abstract (Mar. 2001) B-04353.
Gottman, et al., Balloon Dilatation of Recurrent Ostial Occlusion of the Front Sinus' OASIS-Online Abstract Submission and Invitation System, 1996-2006, Coe Truman Technologies, Inc.
Gottmann, et al. 'Successful Treatment of Recurrent Post-Operative Frontal Sinus Stenoses by Balloon Dilatation' CIRSE. (Oct. 5, 2002)
Gottmann, D. 'Treatment of Stenoses of Upper Air Routes by Balloon Dilation' Proceeding of the 83rd Annual Convention of Association of West German ENT Physicians (1999).
Gupta, D. et al., 'Dacrystitis Secondary to an Iatrogenic Foreign Body in the Lacrimal Apparatus' Ear, Nose & Throat Journal (2009) www.findarticles.com/p/articles/mi_m0BUM/is_7_88/ai_n32428620/.
Hashim, et al. 'Balloon Compression of the Intermaxillary Sinus for Intractable Post Traumatic Bleeding from the Maxillary Artery' Scandinavian Journal of Plastic and reconstruction Surgery and Hand Surgery (1999) vol. 33 pp. 321-324.
Hojo, M. et al, 'Electrophilic Substitutions of Olefinic Hydrogens II. Acylation of Vinyle Ethers and N Vinyl Amides Chemistry Letters' (1976) pp. 499-502. Chemical Society of Japan.
Hopf, J.U.G. et al. 'Miniature Endoscopes in Otorhinolaryngologic Applications' Min Invas Ther & Allied Technol. (1998) vol. 7, No. 3 pp. 209-218.
Hosemann, W. et al. A Dissection Course on Endoscopic Endonasal Sinus Surgery (2005) Endo-Press, Tuttlingen pp. 4-37.
Hosemann, W. et al. 'Endonasal Frontal Sinusotomy in Surgical Management of Chronic Sinusitis: A Critical Evaluation' American Journal of Rhinology. vol. 11, No. 1 (1997) pp. 1-9.
Hosemann, M.E. et al. 'Experimentelle Untersuchungen sur Wundheilung in den Nasenebenholhlen. II. Spontaner Wundschluss und medikamentose Effekte im standardisierten Wundmodell.' HNO 39 (1991) pp. 48-54. 'Experimental investigations on wound healing of the paranasal sinuses. II. Spontaneous wound closure and pharmacological effects in a standardized animal model.' HNO 39 (1991) pp. 48-54.
Hosemann, W.G. et al. 'Minimally Invasive Endonasal Sinus Surgery' Thieme, Stuttgart, New York (2000).
Hosemann, M.E. et al. 'Normal Wound Healing of the Paranasal Sinuses—Clinical and Experimental Investigations' Eur Arch Otorhinolarygol. vol. 248, (1991) pp. 390-394.
Hosemann, W. et al. 'Behandlung nach Nasennebenhohleneingriffen, part 2: Theapeutische Maßnahem' HNO akutell 7(1999) pp. 291-302
Hospital Corpsman Sickcall Screener's Handbook. Naval Hospital Great Lakes (Apr. 1999) www.brooksidepress.org/Products/Operationa. Medicine/DATA. 2001 pp. 1-6.
Hybels, R.L. 'Transillumination During Osteoplastic Frontal Sinusotomy' The Laryngoscope. vol. 91 (Sep. 1981) pp. 1560.

(56) References Cited

OTHER PUBLICATIONS

Ijaduola, T.G.A. 'Use of a Foley Catheter for Short-Term Drainage in Frontal Sinus Surgery' The Journal of Laryngology and Otology. (1989) vol. 103. pp. 375.378.
Ingals, E.F. 'New Operation and Instruments for Draining the Frontal Sinus' Ann. Otol. Rhinol. Layyngol. vol. 14 (1905) pp. 644-649.
Iro, H. et al., 'A New Device for Frontal Sinus Endoscopy: First Clinical Report' Otolaryngol. Head Neck Surg. (2001) vol. 125 No. 6 pp. 613-616.
Jacobs, J.B. '100 Years of Frontal Sinus Surgery' Laryngoscope. vol. 107 (1997) pp. 1-36.
K-Splint Internal Nasal Splints; Jan. 25, 2007; www.invotec.net/rhinology/ksplint.html.
Kaiser, H. et al 'Cortizontherapie, Corticoide in Klinik und Praxis' Thieme, Stuggart (1992) pp. 390-401.
Kennedy, D.W., M.D. et al. 'Diseases of the Sinuses: Diagnosis and Management' (Copyright 2001) by B.C. Decker Inc.
Khomutov, S.M. et al. 'Dissolution of a Mixture of Steroids in Cyclodextrin Solutions: a Model Description' Pharmaceutical Chemistry Journal. vol. 35, No. 11 (Nov. 2001) pp. 627-629.
Kingdom, T.T. et al. 'Image-Guided Surgery of the Sinuses: Current Technology and Applications' Otolaryngol. Clin. North Am. vol. 37, No. 2 (Apr. 2004) pp. 381-400.
Klossek, J.M. et al. 'Local Safety of Intranasal Trimcinolone Acentonide: Clinical and Histological Aspects of Nasal Mucosa in the Long-Term Treatment of Perennial Allergic Rhinitis' Rhinology. vol 39, No. 1 (2001) pp. 17-22.
Kozlov et al. 'Diagnosis and Treatment of Sinusitis by YAMIK Sinus Catheters' Rhinology (1996) vol. 34, pp. 123-124.
Kuhn, et al. 'The Agger Nasi Cell in Frontal Recess Obstruction: An Anatomic, Radiology and Clinical Correlation' Operative Techniques in Otolaryngology-Head and Neck Surgery. vol. 2, No. 4 (1991) pp. 226-231.
Laliberte, F. et al. 'Clinical and Pathologic Methods to Assess the Long-Term Safety of Nasal Corticosteroids' Allergy. vol. 55, No. 8 (2000) pp. 718-722.
Lang, E.V., et al., 'Access Systems for Puncture at an Acute Angle' J. Vasc. Interv. Radiol. (1995) vol. 6, No 5 pp. 711-713.
Lanza, D.C. 'Postoperative Care and Avoiding Frontal Recess Stenosis' International Advanced Sinus Symposium Jul. 21-24, 1993.
Large, G.C. 'Crystalline Tetracycline Hydrochloride in the Treatment of Acute and Chronic Maxillary Sinusitis' Canda M.A.J. (1958) vol. 79 pp. 15-16.
Lund, V.J. 'Maximal Medical Therapy for Chronic Rhinosinusitis' Otolaryngol Clin N. Am. vol. 38 (2005) pp. 1301-1310.
Maran, A.G.D. et al. 'The Use of the Foley Balloon Catheter in the Tripod Fracture' J. Laryngol. Otol. (1971) vol. 85, Issue 9, pp. 897-902.
May, M. et al. 'Frontal Sinus Surgery: Endonasal Drainage Instead of an External Osteopolstic Approach' Op Tech Otolaryngo Head Neck Surgery. 6 (1995) pp. 184-192.
Medtronic, xomed.com-MicroFrance Catalog Browser. Www.xomcat.com/xomfrance/index.php?zone=both&cat=18&sub=58&prodline=1272 (Dec. 31, 2003) pp. 1-2.
Mehan, V.K. et al., 'Coronary Angioplasty through 4 French Diagnostic Catheters' Cathet. Cardiovasc. Diagn. (1993) vol. 30, No. 1 pp. 22-26.
Mellor, J.M. et al 'Synthesis of Trifluromethylnaphthalenes' Tetrahedron. vol. 56 (2000) pp. 10067-10074. Elsevier Science Ltd.
Metson, R., et al., 'Endoscopic Treatment of Sphenoid Sinusitis' Otolaryngol. Head Neck Surg. (1996) vol. 114, No. 6 pp. 736-744.
Metson, R. 'Holmium: YAG Laser Endoscopic Sinus Surgery: A Randomized Controlled Study' Laryngoscope. vol. 106, Issue 1, Supplement 77 (Jan. 1996) pp. 1-18.
Miller, et al. 'Management of Fractures of the Supraorbital Rim' Journal of Trauma. vol. 18, No. 7 (Jul. 1978) pp. 507-512.
Min, Y-G et al. 'Mucociliary Activity and Histopathology of Sinus Mucosa in Experimental Maxilary Sinusitis: A Comparison of Systemic Administration of Antibiotic and Antibiotic Delivery by Polylactic Acid Polymer' Laryngoscope. vol. 105 (Aug. 1995) pp. 835-842.
Mols, B. 'Movable Tool Tip for Keyhole Surgery' Delft Outlook, vol. 3 (2005) pp. 13-17.
Mooney, M.R., et al., 'Monorail™ Piecolino Catheter: A New Rapid Exchange/Ultralow Profile Coronary Angioplasty System' Cathet. Cardiovasc. Diagn. (1990) vol. 20, No. 2 pp. 114-119.
Moriguchi, T. et al. 'Additional-Elimination Reaction in the Trifluoroacetylation of Electron-Rich Olefins' J. Org. Chem. vol. 60, No. 11 (1995) pp. 3523.3528. American Chemical Society.
Nasal Surgery and Accessories, Jan. 25, 2007; www.technologyforlife.com/au/ent/nasal.html.
Park, K. et al. 'Biodegradable Hydrogels for Durg Delivery' (1993) Technomic Publishing Inc. Lancaster.
Piccirillo, J.F. et al. 'Physchometric and Clinimetric Validity of the 20-Item Sino-Nasal Outcome test (SNOT-2O)' Copyright 1996 Washington University, St. Louis, MO.
Piers, et al. 'A Flexible Distal Tip with Two Degrees of Freedom for Enhanced Dexterity in Endoscopic Robot Surgery' Proceedings 13th Micromechanics Europe Workshop (2002) pp. 271-274.
Podoshin, L et al. 'Balloon Technique for Treatment of Frontal Sinus Fractures' The journal of Laryngology & Otology (1967), vol. 81. pp. 1157-1161.
Pownell, P.H. et al., 'Diagnostic Nasal Endoscopy' plastic & Reconstructive Surgery (1997) vol. 99, Iss5 pp. 1451-1458.
Prince, et al. 'Analysis of the Intranasal Distribution of Ointment' J Otolaryngol. vol. 26 (1997) pp. 357-360.
Ramsdale, D.R., Illustrated Coronary Intervention: A case-oriented approach, (2001) Martin Dunitz Ltd. pp. 1-5.
Ritter, F.N. et al., Atlas of Paranasal Sinus Surgery (1991) Igaku-Shoin Medical Pub. pp. 1-81.
Robison, J. Mathews, M.D. 'Pressure Treatment of Maxillary Sinusitis' J .A.M.A. (May 31, 1952) pp. 436-440.
Robison, J. Mathews, M.D. 'Pressure Treatment of Purulent Maxillary Sinusitis' TEXAS State Journal of Medicine (May 1952) pp. 281-288.
St. Croix et al. 'Genes Expressed in Human Tumor Endothelium' Science, vol. 289 (May 15, 2000) pp. 1197-1202.
Sama, A., et al., 'Current Opinions on the Surgical Management of Frontal Sinus Disease' ENT News. Www.pinpointmedical.com/ent-news (2009) vol. 17, No. 6 pp. 60-63.
Sanborn, T.A. et al., 'Percutaneous Endocardial Transfer and Expression of Genes to the Myocardium Utilizing Fluropscopic Guidance' Catheter Cardiovasc. Interv. (2001) vol. 52, No. 2 pp. 260-266.
Sawbones Catalog 2001, Pacific Research Laboratories, Inc., Vashon Washington 98070 USA.
Saxon, R.R. et al., 'Technical Aspects of Accessing the Portal Vein During the TIPS Procedure' J. Vasc. Interv. Radiol. (1997) vol. 8, No. 5 pp. 733-744.
Schaeffer, S.D., M.D. 'Rhinology and Sinus Disease: A Problem-Oriented Approach' (Copyright 1988) by Mosby, Inc.
Schneider. Pfizer Ad for Softip [date of publication unknown].
Shah, N.J. et al., 'Endoscopic Pituitary Surgery—A Beginner's Guide' Indian Journal of Otolaryngology and Head and Neck Surgery (2004) vol. 56, No. 1 pp. 71-78.
Shah, N.J. 'Functional Endoscopic Sinus Surgery' (1999); found at bhj.org/journal/1999_4104_oct99/sp_659.htm.
Single-Pole and Multi-Pole Lightguides for UV Spot Light Curing Sytems.
Sinusitis, Maxillary, Acute Surgical Treatment. Http://www.emedicine.com/ent/topic340.htm. Aug. 29, 2006. pp. 1-11.
Sobol, et al. 'Sinusitis, Maxillary, Acute Surgical Treatment.' eMedicine. Retrieved from the Internet: <<http://emedicine.medscape.com/article/862030-print>> (Nov. 16, 2010) pp. 1-11.
Stammberger, H. 'Komplikationen entzundlicher Nasennebenhohlenerkrankungen eischließ iatrogen bedingter Komplikationen' Eur Arch Oti-Rhino-Laryngol Supple. (Jan. 1993) pp. 61-102.
Stammberger, et al. Chapter 3 'Special Endoscopic Anatomy of the Lateral Nasal Wall and Ethmoidal Sinuses' Functional Endoscopic Sinus Surgery. (1991) Ch. 3, pp. 49-87.

(56) References Cited

OTHER PUBLICATIONS

Strohm, et al. Die Behandlung von Stenosen der oberen Luftwege mittels rontgenologisch gesteuerter Ballondilation (Sep. 25, 1999) pp. 1-4.
Strohm, et al 'Le Traitement des Stenoses Voies Aeriennes Superieures Par Dilation Ay Balloon' Sep. 25, 1999.
Strohm, et al. 'Treatment of Stenoses of the Upper Airways by Balloon Dilation' Sudwestdeutscher Abstract 45 (Sep. 25, 1999) pp. 1-3.
SurgTrainer Product Information 2003, Surg Trainer, Ltd. Ibaraki, Japan.
SurgTrainer Product Information 'Incisive Human Nasal Model for ESS Training' Surg Trainer, Ltd. Ibaraki, Japan (2004) www1.accsnet.ne.jp/~juliy/st/en/partslist.html.
Tabor, M.H. et al., 'Symptomatic Bilateral Duct Cysts in a Newborn—Rhinoscopic Clinic' Ear, Nose & Throat Journal (2003) www.findarticles.com/p/articles/mi_m0BUM/is_2_82/ai_98248244 pp. 1-3.
Tarasov, D.I. et al. 'Application of Drugs Based on Polymers in the Treatment of Acute and Chronic Maxillary Sinusitis' Vestn Otorinoloaringol. vol. 6 (1978) pp. 45-47.
Terumo. Medi-Tech. Boston Scientific. (1993) Ad of Glidewire.
The Operating Theatre Journal (www.otjonline.com) 'Disposable Medical Device for Wound Disclosure/The Tristel Purple Promotion—A Collaboration between Tristel PLC and Karl Storz Endoscopy (UK) Ltd.' p. 4.
Weber, R. et al. 'Endonasale Stirnhohlenchirugie mit Langzeiteinlage eines Platzhalters' Laryngol. Rhinol. Otol. vol. 76 (1997) pp. 728-734. (English Abstract).
Weber, R. et al., 'Videoendoscopic Analysis of Nasal Steroid Distribution' Rhinology. vol. 37 (1999) pp. 69-73.
Weiner, R.I., D.O., et al., 'Development and Application of Transseptal Left Heart Catheterization' Cathet. Cardiovasc. Diagn. (1988) vol. 15, No. 2, pp. 112-120.
Wiatrik, B.J., et al., 'Unilateral Choanal Atresia: Initial Presentation and Endoscopic Repair' International Journal of Pediatric Otorhinolaryngology (1998) vol. 46, pp. 27-35.
Woog, et al. 'Paranasal Sinus Endoscopy and Orbital Fracture Repair' Arch Ophthalmol. vol. 116 (May 1998) pp. 688-691.
Wormald, P.J., et al., 'The 'Swing-Door' Technique for Uncinectomy in Endoscopic Sinus Surgery' The Journal of Laryngology and Otology (1998) vol. 112, pp. 547-551.
Xomed-Treace. Bristol-Myers Squibb. Ad for Laser Shield II. Setting the Standards for Tomorrow. [date of publication unknown].
Yamauchi, Y. et al., 'Development of a Silicone Model for Endoscopic Sinus Surgery' Proc International Journal of Computer Assisted Radiology and Surgery vol. 99 (1999) p. 1039.
Yamauchi, Y., et al., 'A Training System for Endoscopic Sinus Surgery with Skill Evaluation' Computer Assisted Radiology and Surgery (2001) with accompanying copy of poster presentation.
Yanagisawa et al. 'Anterior and Posterior Fontanelles.' Ear, Nose & Throat Journal (2001) vol. 80. pp. 10-12.
Zimarino, M., M.D., et al., 'Initial Experience with the EuropassTM: A new Ultra-Low-Profile Monorail Balloon Catheter' Cathet. Cardiovasc. Diagn. (1994) vol. 33, No. 1, pp. 76-79.
Australian Office Action, Examiners First Report dated Apr. 8, 2010 for Application No. AU 2005274794.
Australian Office Action, Examiners First Report dated Dec. 9, 2011 for Application No. AU 2006292818.
Australian Office Action dated Feb. 12, 2014 for Application No. AU 2012202103.
Australian Office Action dated Aug. 1, 2014 for Application No. AU 2012244072.
Australian Office Action dated Sep. 17, 2014 for Application No. AU 2012202103.
Australian Office Action dated Sep. 30, 2014 for Application No. AU 2009293312.
Australian Office Action dated Oct. 1, 2014 for Application No. AU 2009333010.
Australian Office Action dated Jul. 8, 2015 for Application No. AU 2012244072.
Canadian Office Action dated Jul. 10, 2015 for Application No. CA 2,617,054.
Canadian Office Action dated Dec. 16, 2015 for Application No. CA 2,751,665.
Chinese Office Action, First Office Action dated Nov. 5, 2012 for CN 200980137396.1.
Chinese Search Report dated Oct. 29, 2012 for Application No. CN 200980137396.1.
Chinese Search Report dated Jan. 11, 2013 for Application No. CN 200980152995.0.
Chinese Office Action, First Office Action dated Jan. 29, 2013 for CN 200980152995.1.
Chinese Office Action, Decision of Rejection, dated 2014 for Application No. CN 200980152995.1.
Chinese Office Action, Third Office Action dated Feb. 27, 2014 for Application No. CN 200980152995.1.
Chinese Office Action and Search Report dated Jan. 21, 2015 for Application No. CN 201310672731.6.
European Communication dated Sep. 4, 2008 for Application No. EP 05773189.
European Communication dated Jun. 19, 2009 for Application No. EP 05773189.
European Communication dated Sep. 27, 2011 for Application No. EP 06800540.4.
European Communication dated Aug. 1, 2012 for Application No. EP 06784759.0.
European Communication dated Aug. 24, 2012 for Application No. EP 05798331.4.
European Communication dated Nov. 9, 2012 for Application No. EP 07750248.2.
European Communication dated Apr. 19, 2012 for Application No. EP 08746715.5.
European Communication dated Jan. 7, 2013 for Application No. EP 08746715.5.
European Communication dated Apr. 11, 2013 for Application No. EP 05778834.1.
European Communication dated May 10, 2013 for Application No. EP 06751637.7.
European Communication dated Sep. 3, 2013 for Application No. EP 12182998.0.
European Communication dated Feb. 26, 2014 for Application No. EP 06800540.4.
European Communication dated Aug. 11, 2014 for Application No. EP 12182998.0.
European Communication dated Aug. 26, 2014 for Application No. EP 12183000.4.
European Communication dated Nov. 26, 2014 for Application No. EP 07836108.6.
European Communication dated Feb. 17, 2016 for Application No. EP 12162712.9.
European Exam Report dated Feb. 22, 2006 for Application No. EP 02716734.5.
European Exam Report dated Feb. 8, 2007 for Application No. EP 02716734.5.
European Search Report and Written Opinion dated Sep. 11, 2009 for Application No. EP 06815174.
European Search Report dated Mar. 16, 2010 re Application No. EP 06718986.
European Search Report dated Sep. 27, 2011 for Application No. EP 10182961.
European Search Report dated Sep. 29, 2011 for Application No. EP 10182893.
European Search Report dated Jul. 23, 2012 for Application No. EP 12162709.
European Search Report dated Jul. 24, 2012 for Application No. EP 12162712.
European Search Report dated Aug. 31, 2012 for Application No. EP 12173295.
European Search Re ort dated Oct. 10, 2012 for Application No. EP 12175607.
European Search Report dated Nov. 22, 2012 for Application No. EP 12182993.

(56) References Cited

OTHER PUBLICATIONS

European Search Report dated Dec. 5, 2012 for Application No. EP 12182998.
European Search Report dated Jan. 9, 2013 for Application No. EP 12183000.
European Search Report dated Jan. 11, 2013 for Application No. EP 12183002.
European Search Report dated Aug. 13, 2013 for Application No. EP 13172140.
European Search Report dated Sep. 9, 2013 for Application No. EP 13179223.
European Search Report dated May 19, 2015 for Application No. EP 08746464.0.
European Search Report dated Jun. 23, 2015 for Application No. EP 12162712.9.
European Search Report dated Jun. 23, 2015 for Application No. EP 12162709.5.
Extended European Search Report dated Jan. 17, 2014 for Application No. EP 108426321.1.
Extended European Search Report dated Sep. 15, 2015 for Application No. EP 15163549.7.
Partial European Search Report dated Sep. 20, 2007 for Application No. EP 07252018.
Partial European Search Report dated Mar. 25, 2008 for Application No. EP 07252018.
Supplemental Partial European Search Report dated Jun. 2, 2008 for Application No. EP 05773189.
Supplemental Partial European Search Report dated Jul. 1, 2009 for Application No. EP 06815285.
Supplemental Partial European Search Report dated Nov. 19, 2010 for Application No. EP 06751637.
Supplemental European Search Report dated Jan. 29, 2010 for Application No. EP 07836108.
Supplemental European Search Report dated Feb. 2, 2010 for Application No. EP 07836109.
Supplemental European Search Report dated Feb. 17, 2010 for Application No. EP 07836110.
Supplemental European Search Report dated Mar. 1, 2010 for Application No. EP 05778834.
Supplemental European Search Report dated Mar. 16, 2010 for Application No. EP 06718986.
Supplemental European Search Report dated Jun. 22, 2010 for Application No. EP 06784759.
Supplemental European Search Report dated Sep. 23, 2010 for Application No. EP 08746715.
Supplemental European Search Report dated Jan. 28, 2011 for Application No. EP 07777004.
Supplemental European Search Report dated Mar. 31, 2011 for Application No. EP 05798331.
Supplemental European Search Report dated Aug. 30, 2011 for Application No. EP 06800540.
Supplemental European Search Report dated Sep. 29, 2011 for Application No. EP 07750248.
Supplemental European Search Report dated Jan. 14, 2014 for Application No. EP 13184009.
Supplemental European Search Report dated Jan. 17, 2014 for Application No. EP 1084263.
Supplemental European Search Report dated Dec. 9, 2014 for Application No. EP 07839152.
Supplemental European Search Report dated Feb. 13, 2014 for Application No. EP 08746464.
PCT Search Report dated Nov. 30, 2009 for Application No. UPCT/US2009/057203.
International Preliminary Report on Patentability dated Aug. 7, 2006 for Application No. PCT/US05/25371.
International Preliminary Report on Patentability and Written Opinion dated Sep. 25, 2007 for Application No. PCT/US06/002004.
International Preliminary Report on Patentability dated Feb. 15, 2008 for Application No. PCT/US05/13617.
International Preliminary Report on Patentability and Written Opinion dated Nov. 18, 2008 for Application No. PCT/US07/11449.
International Preliminary Report on Patentability and Written Opinion dated Apr. 7, 2009 for Application No. PCT/US07/021170.
International Preliminary Report on Patentability and Written Opinion dated May 5, 2009 for Application No. PCT/US06/036960.
International Preliminary Report on Patentability and Written Opinion dated Oct. 13, 2009 for Application No. PCT/US08/059786.
International Preliminary Report on Patentability and Written Opinion dated Oct. 27, 2009 for Application No. PCT/US08/061343.
International Preliminary Report on Patentability dated Jun. 29, 2011 for Application No. PCT/US2009/069143.
International Search Report dated Jun. 3, 2002 for Application No. PCT/EP02/01228.
International Search Report and Written Opinion dated Apr. 10, 2006 for Application No. PCT/US05/25371.
International Search Report dated May 8, 2007 for Application No. PCT/US2006/16026.
International Search Report dated Aug. 17, 2007 for Application No. PCT/US05/013617.
International Search Report dated Aug. 29, 2007 for Application No. PCT/US06/002004.
International Search Report dated Sep. 25, 2007 for Application No. PCT/US06/037167.
International Search Report dated Oct. 19, 2007 for Application No. PCT/US07/003394.
International Search Report dated May 29, 2008 for Application No. PCT/US07/021170.
International Search Report dated May 29, 2008 for Application No. PCT/US07/021922.
International Search Report dated Jul. 1, 2008 for Application No. PCT/US06/022745.
International Search Report dated Jul. 3, 2008 for Application No. PCT/US2006/029695.
International Search Report dated Jul. 7, 2008 for Application No. PCT/US07/016213.
International Search Report dated Jul. 8, 2008 for Application No. PCT/US07/011474.
International Search Report dated Jul. 17, 2008 for Application No. PCT/US06/036960.
International Search Report and Written Opinion dated Jul. 21, 2008 for Application No. PCT/US05/033090.
International Search Report dated Aug. 25, 2008 for Application No. PCT/US2008/000911.
International Search Report dated Sep. 10, 2008 for Application No. PCT/US07/016212.
International Search Report and Written Opinion dated Sep. 12, 2008 for Application No. PCT/US07/16214.
International Search Report and Written Opinion dated Sep. 17, 2008 for Application No. PCT/US08/059786.
International Search Report and Written Opinion dated Sep. 17, 2008 for Application No. PCT/US08/061343.
International Search Report and Written Opinion dated Oct. 1, 2008 for Application No. PCT/US07/011449.
International Search Report dated Oct. 15, 2008 for Application No. PCT/US2008/061048.
International Search Report dated Nov. 30, 2009 for Application No. PCT/US2009/057203.
International Search Report dated Dec. 10, 2009 for Application No. PCT/US2009/052236.
International Search Report dated Dec. 16, 2009 for Application No. PCT/US2009/050800.
International Search Report dated Mar. 31, 2010 for Application No. PCT/US2009/069143.
International Search Report dated Jul. 8, 2010 for Application No. PCT/US2010/027837.
International Search Report and Written Opinion dated Oct. 6, 2010 for Application No. PCT/US2010/040548.
International Search Report dated Mar. 25, 2011 for Application No. PCT/US2010/062161.
International Search Report dated Mar. 28, 2011 for Application No. PCT/US2010/061850.

(56) References Cited

OTHER PUBLICATIONS

International Search Report dated Mar. 31, 2011 for Application No. PCT/US2010/060898.
International Search Report dated Aug. 9, 2011 for Application No. PCT/US2011/038751.
International Search Report dated May 18, 2012 for Application No. PCT/US2011/052321.
International Written Opinion dated Aug. 9, 2011 for Application No. PCT/US2011/038751.
Partial International Search Report dated Feb. 7, 2012 for Application No. PCT/US2011/052321.
Japanese Office Action, Examiner's Decision of Refusal dated Oct. 18, 2011 for Application No. JP 2007-509632.
Japanese Office Action, Notification of Reasons for Refusal dated Apr. 26, 2011 for Application No. JP 2007-532485.
Japanese Office Action, Notification of Reasons for Refusal dated Jan. 24, 2012 for Application No. JP 2007-532485.
Japanese Office Action, Notification of Reasons for Refusal dated Aug. 16, 2011 for Application No. JP 2008-516013.
Japanese Office Action, Notification of Reasons for Refusal dated Nov. 8, 2011 for Application No. JP 2008-524250.
Japanese Office Action, Notification of Reasons for Refusal dated Jun. 25, 2013 for Application No. JP 2012-131840.
Japanese Office Action, Notification of Reasons for Refusal dated Sep. 18, 2013 for Application No. JP 2011-527942.
Japanese Office Action, Notification of Reasons for Refusal dated Nov. 12, 2013 for Application No. JP 2011-542562.
Japanese Office Action, Notification of Reasons for Refusal dated Jan. 7, 2014 for Application No. JP 2012-266049.
Japanese Office Action, Reasons for Refusal, dated Sep. 2, 2014 for Application No. JP 2012-544859.
Japanese Office Action, Reasons for Refusal, dated Jun. 9, 2015 for Application No. JP 2014-147174.
Russian Office Action dated Sep. 28, 2012 for Application No. RU 2011130530.
Russian Office Action dated Mar. 19, 2013 for Application No. RU 2011130530.
USPTO Office Action dated Sep. 16, 2005 for U.S. Appl. No. 10/259,300.
USPTO Office Action dated Jul. 7, 2006 for U.S. Appl. No. 10/259,300.
USPTO Office Action dated Feb. 13, 2007 for U.S. Appl. No. 10/259,300.
USPTO Office Action dated Oct. 9, 2007 for U.S. Appl. No. 10/259,300.
USPTO Office Action dated Jan. 24, 2008 for U.S. Appl. No. 10/259,300.
USPTO Office Action dated Oct. 6, 2008 for U.S. Appl. No. 10/259,300.
USPTO Office Action dated May 29, 2007 for U.S. Appl. No. 10/912,578.
USPTO Office Action dated Nov. 14, 2007 for U.S. Appl. No. 10/912,578.
USPTO Office Action dated Dec. 10, 2007 for U.S. Appl. No. 10/912,578.
USPTO Office Action dated Oct. 18, 2007 for U.S. Appl. No. 11/037,548.
USPTO Office Action dated Dec. 6, 2007 for U.S. Appl. No. 11/037,548.
USPTO Office Action dated Apr. 9, 2008 for U.S. Appl. No. 11/037,548.
USPTO Office Action dated Nov. 28, 2007 for U.S. Appl. No. 11/234,395.
USPTO Office Action dated Sep. 12, 2008 for U.S. Appl. No. 10/829,917.
USPTO Office Action dated Nov. 17, 2008 for U.S. Appl. No. 10/829,917.
USPTO Office Action dated Mar. 18, 2009 for U.S. Appl. No. 10/829,917.
USPTO Office Action dated Nov. 9, 2009 for U.S. Appl. No. 10/829,917.
USPTO Office Action dated Oct. 29, 2008 for U.S. Appl. No. 11/347,147.
USPTO Office Action dated Feb. 4, 2009 for U.S. Appl. No. 11/347,147.
USPTO Office Action dated Aug. 6, 2009 for U.S. Appl. No. 11/347,147.
USPTO Office Action dated Nov. 7, 2008 for U.S. Appl. No. 10/944,270.
USPTO Office Action dated Jan. 28, 2009 for U.S. Appl. No. 10/944,270.
USPTO Office Action dated Apr. 21, 2009 for U.S. Appl. No. 10/944,270.
USPTO Office Action dated Nov. 17, 2008 for U.S. Appl. No. 12/117,582.
USPTO Office Action dated Mar. 3, 2009 for U.S. Appl. No. 12/117,582.
USPTO Office Action dated Aug. 6, 2009 for U.S. Appl. No. 12/117,582.
USPTO Office Action dated Nov. 17, 2008 for U.S. Appl. No. 12/118,931.
USPTO Office Action dated Mar. 4, 2009 for U.S. Appl. No. 12/118,931.
USPTO Office Action dated Jul. 30, 2009 for U.S. Appl. No. 12/118,931.
USPTO Office Action dated Nov. 25, 2008 for U.S. Appl. No. 12/117,961.
USPTO Office Action dated Aug. 6, 2009 for U.S. Appl. No. 12/117,961.
USPTO Office Action dated Dec. 5, 2008 for U.S. Appl. No. 12/120,902.
USPTO Office Action dated Oct. 21, 2009 for U.S. Appl. No. 12/120,902.
USPTO Office Action dated Mar. 17, 2009 for U.S. Appl. No. 11/690,127.
USPTO Office Action dated Mar. 23, 2009 for U.S. Appl. No. 11/804,309.
USPTO Office Action dated Mar. 23, 2009 for U.S. Appl. No. 11/926,326.
USPTO Office Action dated Aug. 28, 2009 for U.S. Appl. No. 11/150,847.
USPTO Office Action dated Dec. 29, 2008 for U.S. Appl. No. 11/193,020.
USPTO Office Action dated May 13, 2009 for U.S. Appl. No. 11/193,020.
U.S. Appl. No. 60/844,874, filed Sep. 15, 2006.
U.S. Appl. No. 60/922,730, filed Apr. 9, 2007.
U.S. Appl. No. 61/052,413, filed May 12, 2008.
U.S. Appl. No. 61/084,949, filed Jul. 30, 2008.
U.S. Appl. No. 11/789,705, filed Apr. 24, 2007.
U.S. Appl. No. 11/804,308, filed May 16, 2007.
U.S. Appl. No. 11/804,309, filed May 16, 2007.
U.S. Appl. No. 14/221,550, filed Mar. 21, 2014.
U.S. Appl. No. 14/221,621, filed Mar. 21, 2014.
U.S. Appl. No. 14/221,714, filed Mar. 21, 2014.
U.S. Appl. No. 14/265,888, filed Apr. 30, 2014.
U.S. Appl. No. 14/266,002, filed Apr. 30, 2014.
U.S. Appl. No. 14/266,025, filed Apr. 30, 2014.
U.S. Appl. No. 14/327,593, filed Jul. 10, 2014.
U.S. Appl. No. 14/464,948, filed Aug. 21, 2014.
U.S. Appl. No. 14/993,444, filed Jan. 12, 2016.
U.S. Appl. No. 15/083,826, filed Mar. 29, 2016.
U.S. Appl. No. 15/187,938, filed Jun. 21, 2016.
U.S. Appl. No. 15/624,111, filed Jun. 15, 2017.
Definition of "bent" as accessed on Sep. 10, 2015 http://dictionary.reference.com/browse/bent.
Meriam-Webster definition of "lumen" as accessed Jun. 10, 2016, http://www.meriam-webster.com/dictionary/lumen.
European Communication dated Sep. 26, 2016 for Application No. EP 12162712.9.
Extended European Search Report dated Jun. 28, 2017 for Application No. EP 17159646.3.

(56) References Cited

OTHER PUBLICATIONS

Supplemental European Search Report and Written Opinion dated Sep. 8, 2011 for EP 06800540.4.
Supplemental European Search Report dated Mar. 24, 2010 for Application No. EP 07836108.6.
Supplemental European Search Report dated Feb. 27, 2014 for Application No. EP 08746464.0.
Japanese Office Action, Notification of Reasons for Refusal dated Mar. 29, 2016 for Application No. JP 2012-266049.

* cited by examiner

ENDOSCOPIC METHODS AND DEVICES FOR TRANSNASAL PROCEDURES

CROSS-REFERENCE

This application is a continuation of application Ser. No. 14/993,444, filed Jan. 12, 2016, published as U.S. Pub. No. 2016/0192830 on Jul. 7, 2016, which is a continuation of application Ser. No. 11/888,284, filed Jul. 31, 2007, now U.S. Pat. No. 9,265,407, issued Feb. 23, 2016, which is a divisional application of application Ser. No. 11/647,530, filed Dec. 27, 2006, published as U.S. Pub. No. 2007/0167682 on Jul. 19, 2007, now abandoned, which claims the benefit of Provisional Application No. 60/844,874, filed Sep. 15, 2006, and which is a continuation-in-part application of application Ser. No. 11/522,497, filed Sep. 15, 2006, now U.S. Pat. No. 7,559,925, issued Jul. 14, 2009, and which is also a continuation-in-part application of application Ser. No. 11/193,020, filed Jul. 29, 2005, published as U.S. Pub. No. 2006/0063973 on Mar. 23, 2006, now abandoned, which is a continuation-in-part application of application Ser. No. 10/829,917, filed Apr. 21, 2004, now U.S. Pat. No. 7,654,997 issued Feb. 2, 2010; Ser. No. 10/944,270, filed Sep. 17, 2004, published as U.S. Pub. No. 2006/0004323 on Jan. 5, 2006, now abandoned; Ser. No. 11/116,118, filed Apr. 26, 2005, now U.S. Pat. No. 7,720,521, issued May 18, 2010; and Ser. No. 11/150,847, filed Jun. 10, 2005, now U.S. Pat. No. 7,803,150, issued Sep. 28, 2010. Each of the aforementioned applications are hereby expressly incorporated by reference herein, in their entireties, and to which application we claim priority under 35 USC § 120 and 35 USC § 119, respectively.

This application also claims the benefit of U.S. Provisional Application No. 60/844,874, filed Sep. 15, 2006, which application is expressly incorporated herein, in its entirety, by reference thereto and to which we claim priority under 35 USC § 119.

FIELD OF THE INVENTION

The present invention relates generally to medical apparatus and methods and more particularly to devices and methods that are useable to facilitate transnasal insertion and positioning of guidewires and various other apparatus at desired locations within the ear, nose, throat, paranasal sinuses or cranium.

BACKGROUND OF THE INVENTION

Functional endoscopic sinus surgery (FESS) is currently the most common type of surgery used to treat chronic sinusitis. In a typical FESS procedure, an endoscope is inserted into the nostril along with one or more surgical instruments. The surgical instruments are then used to cut tissue and/or bone, cauterize, suction, etc. In most FESS procedures, the natural ostium (e.g., opening) of at least one paranasal sinus is surgically enlarged to improve drainage from the sinus cavity. The endoscope provides a direct line-of-sight view whereby the surgeon is typically able to visualize some but not all anatomical structures within the surgical field. Under visualization through the endoscope, the surgeon may remove diseased or hypertrophic tissue or bone and may enlarge the ostia of the sinuses to restore normal drainage of the sinuses. FESS procedures can be effective in the treatment of sinusitis and for the removal of tumors, polyps and other aberrant growths from the nose.

The surgical instruments used in the prior art FESS procedures have included; applicators, chisels, curettes, elevators, forceps, gouges, hooks, knives, saws, mallets, morselizers, needle holders, osteotomes, ostium seekers, probes, punches, backbiters, rasps, retractors, rongeurs, scissors, snares, specula, suction cannulae and trocars. The majority of such instruments are of substantially rigid design.

In order to adequately view the operative field through the endoscope and/or to allow insertion and use of rigid instruments, many FESS procedures of the prior art have included the surgical removal or modification of normal anatomical structures. For example, in many prior art FESS procedures, a total uncinectomy (e.g., removal of the uncinate process) is performed at the beginning of the procedure to allow visualization and access of the maxilary sinus ostium and/or ethmoid bulla and to permit the subsequent insertion of the rigid surgical instruments. Indeed, in most traditional FESS procedures, if the uncinate process is allowed to remain, such can interfere with endoscopic visualization of the maxillary sinus ostium and ethmoid bulla, as well as subsequent dissection of deep structures using the available rigid instrumentation.

More recently, new devices, systems and methods have been devised to enable the performance of FESS procedures and other ENT surgeries with minimal or no removal or modification of normal anatomical structures. Such new methods include, but are not limited to, uncinate-sparing procedures using Balloon Sinuplasty™ tools and uncinate-sparing ethmoidectomy procedures using catheters, non-rigid instruments and advanced imaging techniques (Acclarent, Inc., Menlo Park, Calif.). Examples of these new devices, systems and methods are described in incorporated U.S. patent application Ser. No. 10/829,917 entitled Devices, Systems and Methods for Diagnosing and Treating Sinusitis and Other Disorders of the Ears, Nose and/or Throat, now U.S. Pat. No. 7,654,997, issued Feb. 2, 2010; Ser. No. 10/944,270 entitled Apparatus and Methods for Dilating and Modifying Ostia of Paranasal Sinuses and Other Intranasal or Paranasal Structures, now abandoned; Ser. No. 11/116,118 entitled Methods and Devices for Performing Procedures Within the Ear, Nose, Throat and Paranasal Sinuses filed Apr. 26, 2005, now U.S. Pat. No. 7,720,521, issued May 18, 2010 and Ser. No. 11/150,847 filed Jun. 10, 2005, now U.S. Pat. No. 7,803,150, issued Sep. 28, 2010, each of which is hereby incorporated herein, in its entirety. Procedures using Balloon Sinuplasty™ tools such as those described in the aboire-noted applications, for example, are performable using various types of guidance including but not limited to C-arm fluoroscopy, transnasal endoscopy, optical image guidance and/or electromagnetic image guidance.

In FESS procedures, the surgeon typically holds or navigates the endoscope with one hand while using the other hand to handle the surgical instruments. Recognizing the desirability of integrating an endoscope with an operative device so that both could be moved with a single hand, application Ser. No. 11/234,395 filed Sep. 23, 2005, now U.S. Pat. No. 7,410,480, issued Aug. 12, 2008 describes a number of transnasally insertable sinus guides that have endoscopes attached thereto or integrated therewith.

There remains a need for further development of new devices and methodology to facilitate the integration of endoscopes with sinus guides and/or other instruments to facilitate endoscopic viewing of guidewires and/or other devices/instruments as they are transnasally inserted, positioned and used to treat disorders of the ear, nose, throat, paranasal sinuses or other intracranial disorders that are transnasally accessible.

SUMMARY OF THE INVENTION

A beneficial aspect of the present invention is to allow a user to be able to see an adjustable view, with an endoscope, that is generally aligned with the same axis of movement of the user's working device. This is particularly useful when the axis of movement is at an angle with respect to the axis of entry into the patient. This aspect allows the user to see "around the corner" of anatomy that ordinarily would block his/her view and which would therefore require removal in a traditional FESS procedure to allow visualization. This aspect of the invention allows the user to also verify the location of his/her Balloon Sinuplasty™ tools without having to use fluoroscopy or image guidance systems, so that the procedure does not have to be performed in an operating room. Another beneficial aspect of the present invention is that it enables a reduction in the amount of fluoroscopy that needs to be performed by the user doing the procedure, resulting in a reduction in radiation exposure to the user and the patient.

Another beneficial aspect of the present invention is that it allows a user to hold a tool with an endoscope attached or incorporated therein, such that both can be held with one hand while allowing the user to manipulate another tool with the other hand, thereby eliminating the need for an assistant.

Another aspect of the invention is a disposable, flexible endoscope that is inexpensive enough for the user to dispose of after ten uses or less, or even after a single use, because the expensive optics that are normally present in the proximal end portion of a conventional flexible (or rigid) endoscope have been relocated in the present embodiments to a re-usable coupler. Also, steerability elements that are normally present in a conventional flexible endoscope have been removed in the present embodiments. Importantly, in at least one embodiment, the entire diameter of the flexible endoscope has an outer diameter of about 0.035 inches or less, so that interventional devices such as a dilatation catheter can be loaded onto and passed over the flexible endoscope. At least one embodiment of the present invention allows the user to load and remove the flexible endoscope from a curved tool, even one having an acute angle bend therein, without breaking or damaging the lens and/or fibers in the endoscope.

In accordance with the present invention, there is provided a method for positioning a working device (e.g., a guidewire, catheter, instrument or other device useable to perform or facilitate a therapeutic or diagnostic task) at a desired location within the ear, nose, throat or cranium of a human or animal subject. In general, this method includes the steps of: (A) providing a guide device that comprises an elongate shaft, a distal end, a second channel into which a working device may be inserted and an first channel into which an endoscope may be inserted; (B) providing an endoscope sized to be received within the endoscope channel; (C) providing a working device sized to be received within the second channel; (D) positioning the endoscope in the endoscope channel; (E) inserting the guide device through a nostril of the subject; (F) using the endoscope to guide or visually verify the positioning of the guide device at the desired location; (G) inserting a working device into the second channel; and (H) advancing the working device to the desired location.

Further in accordance with the present invention, there is provided an endoscope/sinus guide device that is useable to position a working device at a desired location within the ear, nose, throat or cranium of a human or animal subject. In general, this device comprises a transnasally insertable elongate shaft (e.g., a rigid or flexible catheter, cannula or tube) having a proximal end, a distal end, a working channel through which the working device may be advanced and an endoscope channel, a portion of which is angled relative to the elongate shaft, and into which an endoscope may be inserted such that the endoscope may be used to view at least an area beyond the distal end of the shaft. After the endoscope has been used to facilitate placement of the distal end of the guide device to or near the desired location, a working device (e.g., a guidewire, catheter, instrument or other device useable to perform or facilitate a therapeutic or diagnostic task) is then advanceable through the working channel and to the desired location. The elongate shaft of the endoscope/sinus guide device may be straight, curved, malleable or steerable.

Still further in accordance with the present invention, there is provided a transnasally insertable guide system and method for positioning a guidewire at a desired location within the ear, nose, throat or cranium of a human or animal subject. In general, this system comprises a tubular guide (e.g., a sinus guide) that has an elongate shaft and a lumen. At least a portion of the elongate shaft has a predetermined shape, and may be straight, curved, malleable or steerable. A sheath is sized to be inserted into the lumen of the tubular guide. Such sheath comprises an elongate flexible body having a distal end, a scope lumen and a guidewire lumen. An endoscope is advanceable through the scope lumen of the sheath and a guidewire is advanceable through the guidewire lumen such that a distal portion of the guidewire extends out of the distal end of the sheath. The endoscope is useable to view at least a portion of the guidewire as it advances out of the distal end of the sheath. In this manner, the endoscope may be used to guide the advancement of the guidewire to or near the desired location. Thereafter, the sheath and endoscope may be removed leaving the tubular guide and guidewire in place. A working device (e.g., a guidewire, catheter, instrument or other device useable to perform or facilitate a therapeutic or diagnostic task) may then be advanced through the tubular guide and over the guidewire to the desired location where it is useable to perform or facilitate a therapeutic or diagnostic task. In some embodiments, a distal portion of the sheath may be advanceable out of and beyond the distal end of the tubular guide and such distal portion of the sheath may be deflectable (e.g., steerable) in situ. In such deflectable (e.g., steerable) embodiments, a handpiece may be attached to the proximal end of the sheath and such handpiece may include an actuator or other control that is useable to cause the distal portion of the sheath to deflect (e.g., steer) when so desired.

Still further in accordance with the present invention, there is provided a guide system and method wherein a translucent body (e.g., a flexible guidewire tip) is mounted on the distal end of a guide member. An elongate scope is engageable with the translucent body such that light will be cast from the scope, through the translucent body and images will be received by the scope through the translucent body. In this manner, the scope is useable to view an area adjacent to the elongate guide tip, thereby facilitating advancement of the elongate guide tip to a desired location within the body of a human or animal subject. After the elongate guide tip has been advanced to or near the desired location, a working device (e.g., a catheter or other device useable to perform a diagnostic or therapeutic task) is then advanced over the endoscope, translucent member and guide tip. In this manner, the endoscope, translucent member and guide tip combine to perform a function of a continuous guidewire.

Still further in accordance with the present invention, there is provided another guide system and method wherein an elongate guide member (e.g., a flexible guidewire tip) is attached to and extends from the distal end of a rigid or flexible catheter having a side opening. An endoscope is advanceable out of the side opening of the elongate catheter and useable, when so advanced, to view an area adjacent to the elongate guide tip, thereby facilitating advancement of the elongate guide tip to a desired location within the body of a human or animal subject. Thereafter, the endoscope may be retracted back into the catheter and a working device (e.g., a catheter or other device useable to perform a diagnostic or therapeutic task) is then advanceable over the catheter and guide member. In this manner, the catheter and the guide member combine to perform the function of a continuous guidewire.

Further aspects, elements and advantages of the present invention will be understood by those of skill in the art upon reading of the detailed description set forth herebelow.

BRIEF DESCRIPTION OF THE DRAWINGS

FIG. 10A shows a step in a method for using a guide catheter system of the present invention in conjunction with the guidewire of FIG. 10.

FIG. 10B shows another step in a method for using a guide catheter system of the present invention in conjunction with the guidewire of FIG. 10.

FIG. 28 shows an illuminating guidewire having been extended distally of the limit of illumination of the scope, to effectively extend the illumination distance viewable by the scope.

FIG. 37A is a cross sectional view through line 15A-15A of FIG. 37.

FIG. 41A' is a sectional view of a proximal connector device of the present invention operatively attached to the proximal end of the device of FIG. 40A.

FIG. 41B' is a sectional view of a proximal connector device of the present invention operatively attached to the proximal end of the device of FIG. 40D.

DETAILED DESCRIPTION OF THE INVENTION

Before the present devices and methods are described, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a channel" includes a plurality of such channels and reference to "the endoscope" includes reference to one or more endoscopes and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The following detailed description, the accompanying drawings and the above-set-forth Brief Description of the Drawings are intended to describe some, but not necessarily all, examples or embodiments of the invention. The contents of this detailed description do not limit the scope of the invention in any way.

Sinus Guide with Continuous Endoscope Channel

Figures 1, 2:
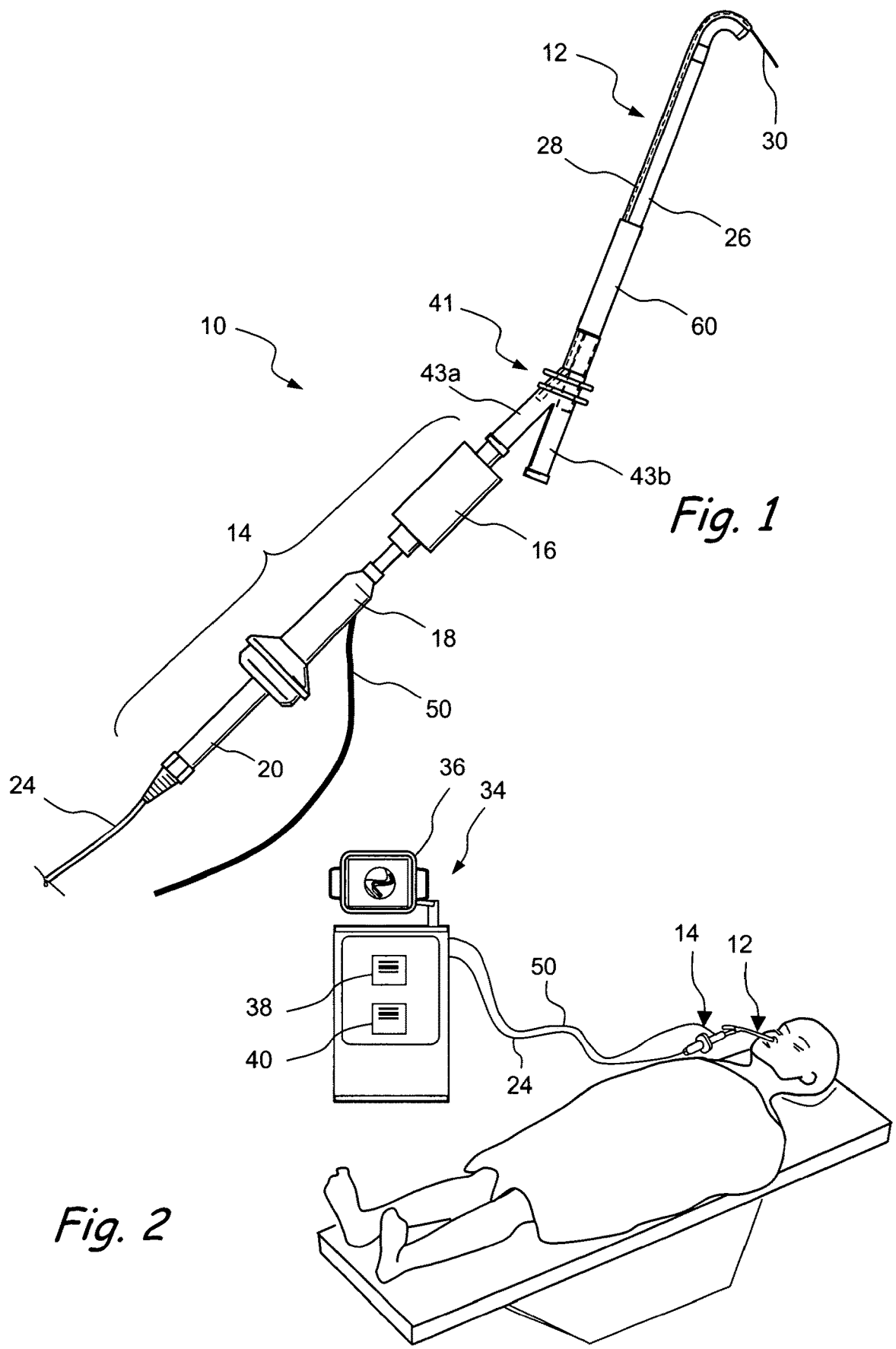
FIG. 1 is a perspective view of one embodiment of a guide system of the present invention.
FIG. 2 is a perspective view of the guide system of the present invention in use on a human subject.
Figure 3A:
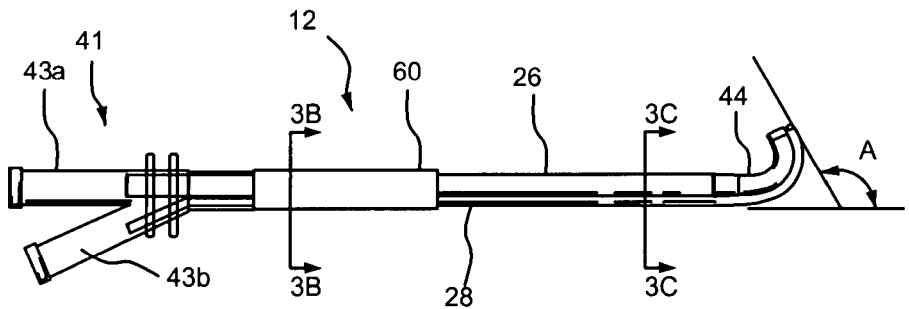
FIG. 3A is a side view of the guide catheter of the system of FIG. 1.
Figure 3B:
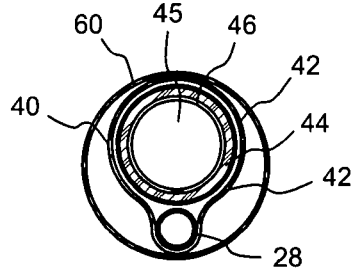
FIG. 3B is a cross sectional view through line 3B-3B of FIG. 3A.
Figure 3C:
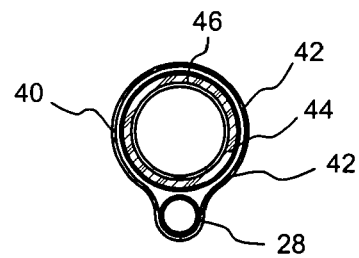
FIG. 3C is a cross sectional view through line 3C-3C of FIG. 3A.

FIG. 1 shows one embodiment of a sinus guide system 10 of the present invention. This sinus guide system 10 comprises a sinus guide 12 and a camera/transmission/endoscope assembly 14. This embodiment of the sinus guide 12 is shown in more detail in FIGS. 3A-3C. As shown, this sinus guide 12 comprises a sinus guide body 26 and an endoscope channel 28 in generally side-by-side arrangement. The sinus guide body 26 comprises a tube 44 having a lumen 45 (e.g., see FIG. 3B), such as a polymer tube made of biocompatible polymeric material. Optionally, a liner 46 (FIG. 3B) may be disposed within the lumen 45 of the tube 44. Such liner may be formed of lubricious or smooth material such as polytetrafluoroethylene (PTFE). Also, optionally, a proximal portion of the tube 44 may be surrounded by an outer tube member 42 formed of material such as stainless steel hypotube. In the embodiment shown, a distal portion of tube 44 extends out of and beyond the distal end of outer tube 42. This protruding distal portion of tube 44 may be straight or curved. Also, it may be preformed at the time of manufacture or malleable to a desired shape at the time of use. When intended for use in accessing the ostium of a paranasal sinus, the distal portion of tube 44 may be curved to form an angle A from about 0 degrees to about 120 degrees. For example, a series of sinus guides 12 having angles A of 0, 30, 70, 90 and 110 degrees may be provided thereby allowing the physician to select the sinus guide angle A that is most appropriate for the particular paranasal sinus ostium to be accessed. Additionally, in some embodiments, a rotation grip 60 may be positioned about a proximal portion of the sinus guide 10, as seen in FIGS. 1, 3A and 3B. This rotation grip 60 may have a smooth or textured round outer surface (e.g., it may be a cylindrical tube) that may be grasped between the fingers of the operator's hand and easily rotated, thereby facilitating rotation (e.g., rolling) of the sinus guide 12 as it is being used. Such rotation of the sinus guide 12 may be desirable for a number of reasons including but not limited to positioning of the distal end of the sinus guide 12 at a desired location and/or maneuvering the location of an endoscope 30 that is inserted through the endoscope channel 28.

The endoscope channel 28 may comprise any structure (e.g., tube, track, groove, rail, etc.) capable of guiding the advancement of a flexible endoscope. In the particular examples shown in these figures, the endoscope channel 28 comprises a tube (e.g., a polymer tube) having a lumen 29 extending therethrough. In the embodiment seen in FIGS. 1-3C, the endoscope channel 28 is attached to and extends along substantially the entire length of the sinus guide body 26. In another embodiment, the endoscope channel 28 can be inside the sinus guide body 26. In other embodiments, such as that shown in FIGS. 4A-4C and described herebelow, the endoscope channel 28 may be interrupted, non-continuous or may extend over less than the entire length of the sinus guide body 26. An outer skin 40 may be heat shrunk or otherwise disposed around the sinus guide body 26 and endoscope channel 28 to hold the endoscope channel 28 at a desired position on the outer surface of the sinus guide body 26. Alternatively, the endoscope channel 28 may be attached to the sinus guide body 26 at one or more locations by any other suitable attachment substance, apparatus or technique, including but not limited to adhesive, soldering, welding, heat fusion, coextrusion, banding, clipping, etc. The particular circumferential location of the endoscope channel 28 can be important in some applications, particularly when the sinus guide body 26 includes a curve formed in its distal portion 44. In this regard, for some applications, the endoscope channel 28 may be affixed at a particular circumferential location on the sinus guide body 26 to allow a flexible fiber endoscope 30 inserted through the endoscope channel 28 to provide a view from a desired or optimal vantage point, without obstruction from adjacent anatomical structures. For example, FIGS. 11A, 11B and 11C show embodiments where the endoscope channel $28_{lower}$, $28_{side}$ and $28_{upper}$ is attached to the sinus guide body 26 at alternative locations and wherein a curve is formed in the distal portion of tube 44.

Figure 11:
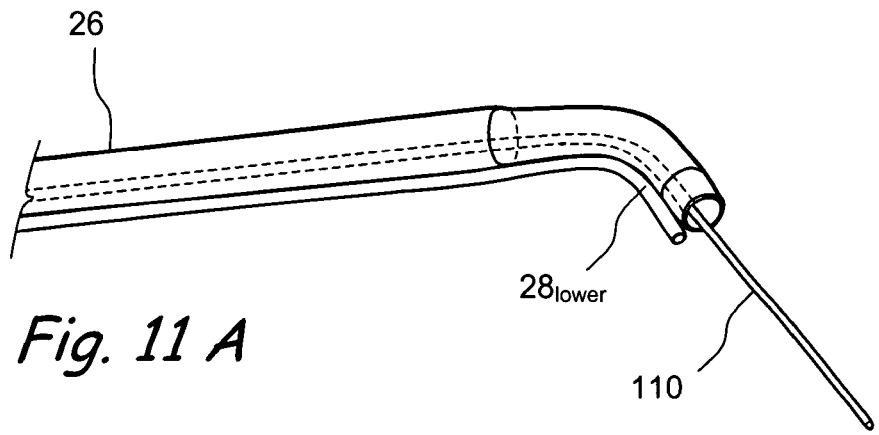
FIG. 11A is a perspective view of the distal portion of a guide catheter device of the present invention having its endoscope lumen disposed on top of the curvature of the guide catheter.
FIG. 11B is a perspective view of the distal portion of a guide catheter device of the present invention having its endoscope lumen disposed along side of the curvature of the guide catheter.
FIG. 11C is a perspective view of the distal portion of a guide catheter device of the present invention having its endoscope lumen disposed below the curvature of the guide catheter.
Figure 11:
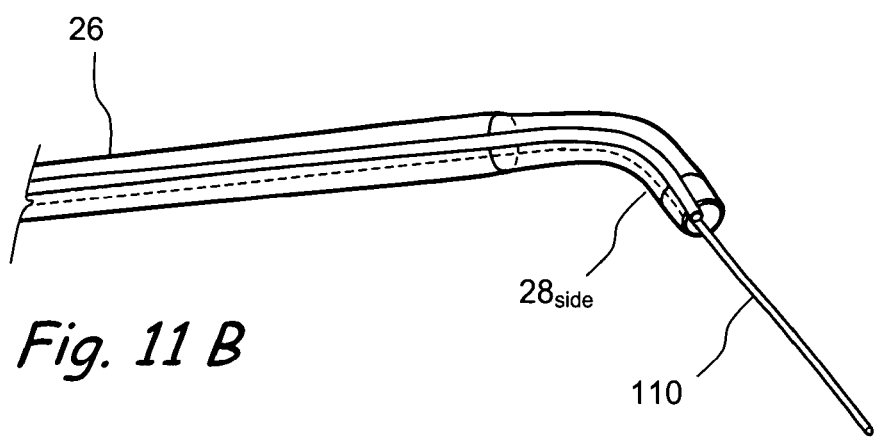
Figure 11:
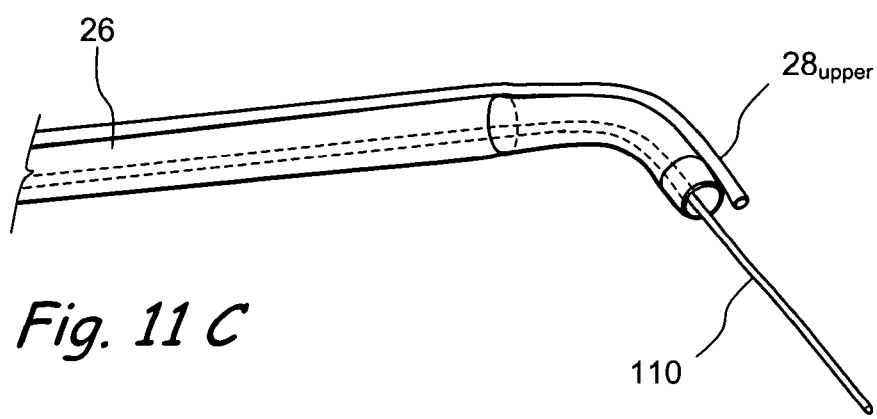

In the example of FIG. 11A, the endoscope channel $28_{lower}$ is on the lower side of the sinus guide body 26 (e.g., the 6 o'clock position adjacent to the lesser aspect of the curve). This construction provides an endoscopic vantage point that is desirable for applications where the ostium of a sphenoid sinus is to be accessed.

In the example of FIG. 11B, the endoscope channel $28_{side}$ is on the right side of the sinus guide body 26 (e.g., the 3 o'clock position adjacent to the right side of the curve). This construction provides an endoscopic vantage point that is desirable for applications where the ostium of a maxillary sinus is to be accessed. Alternatively, the maxillary lumen may terminate before the distal end of the guide, then it can be located on the outside or on the side of the sinus guide body 26.

In FIG. 11C, the endoscope channel $28_{up}$, is on the upper side of the sinus guide body 26 (e.g., the 12 o'clock position adjacent to the greater aspect of the curve). This construction provides an endoscopic vantage point that is desirable for applications where the ostium of a frontal sinus is to be accessed.

Again referring to FIGS. 1-3C, a proximal Y connector 41 may be attached to the proximal end of the sinus guide 12. A first arm 43b of this Y connector comprises a female Luer fitting that is connected to the lumen 45 of the sinus guide body 26. The other arm 43a is a female Luer fitting that is connected to the lumen 29 of the endoscope channel 26.

A camera/cable/endoscope assembly 14 is attachable to arm 43a. In the particular embodiment shown in FIGS. 1 and 3F, the camera/cable/endoscope assembly 14 comprises an adjustable scope/lock extension 16, an endoscope 18 having an elongate flexible scope body 30 and integrated light cable 50, a camera 20 and a monitor cable 24. The scope body 30 is advanced through the scope/lock extension 16 and through the lumen 29 of the endoscope channel 28. As shown in FIG. 2, the light cable 50 and monitor cable 24 may be connected to console 34 that houses a monitor 36, light source 38 and video recorder 40.

Figure 3D:
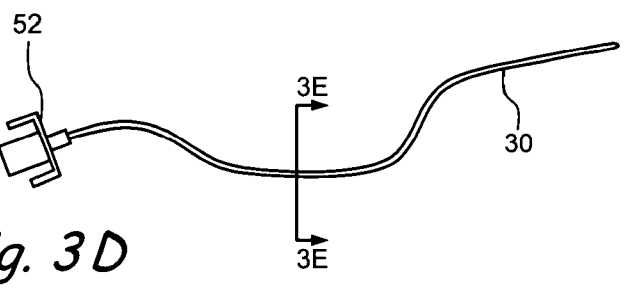
FIG. 3D is a side view of the endoscope of the system of FIG. 1.
Figure 3E:
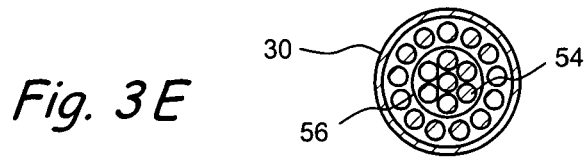
FIG. 3E is a cross sectional view through line 3E-3E of FIG. 3D.
Figure 3F:
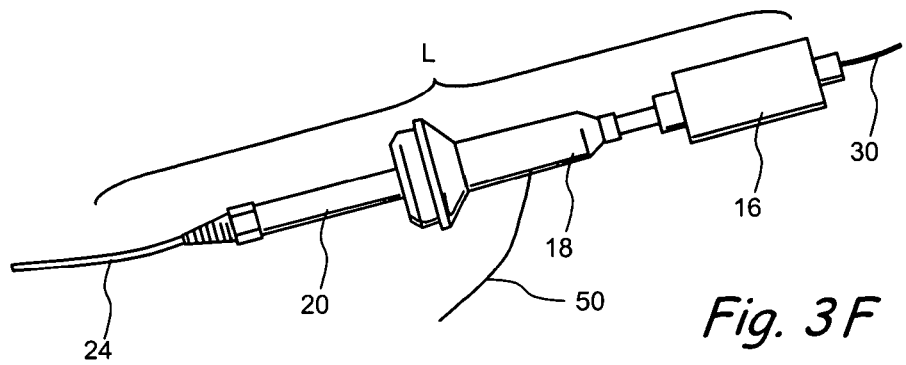
FIG. 3F is a side view of the connector/camera/light cable assembly of the system of FIG. 1.
Figure 4:
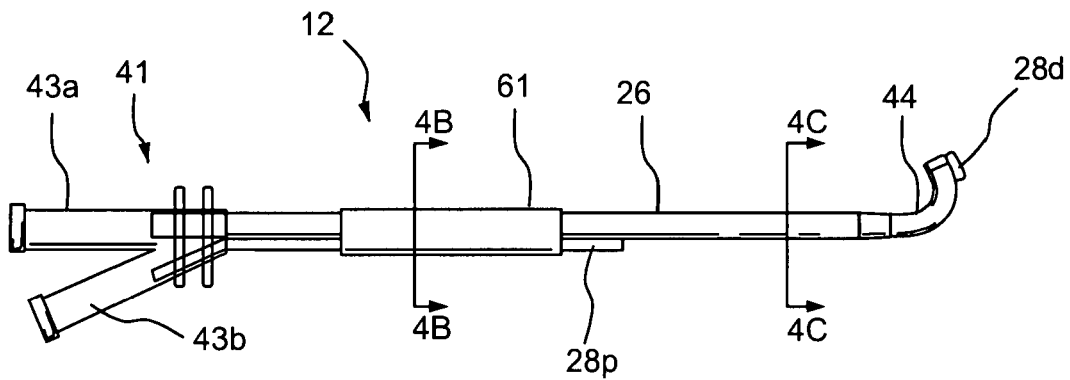
FIG. 4A is a side view of another embodiment of a guide catheter device useable in the guide catheter systems of the present invention.
FIG. 4B is a cross sectional view through line 4B-4B of FIG. 4A.
FIG. 4C is a cross sectional view through line 4C-4C of FIG. 4A.
Figure 4:
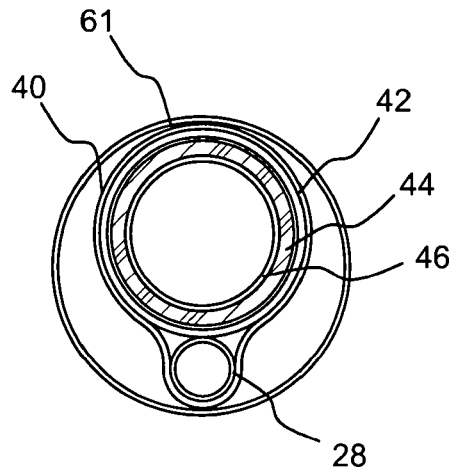
Figure 4:
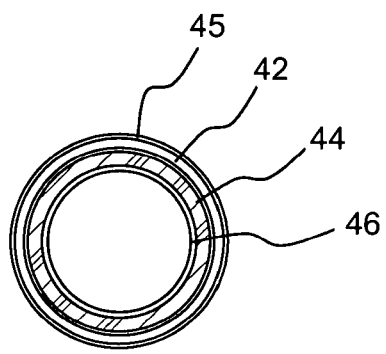

FIGS. 3D and 3E show a flexible endoscope 30 attached to a proximal body member 52 that engages and attaches to the adjustable scope/lock extension 16. As seen in the cross section of FIG. 3E, the scope 30 comprises a flexible shaft having an image fiber bundle 54 that extends coaxially through the center with light transmitting fibers 56 disposed about the periphery. In one preferred embodiment, the flexible shaft is a braided polyimide sheathing that has a maximum outer diameter of 0.0375 inches and a length of two feet. Preferably, the image fiber bundle is made up of 10,000 thin image fibers and the light transmitting fibers are illumination fibers with a diameter of between about 0.008 and 0.020 inches, with a minimum lux of about 10,000. Preferably, the distal end of the flexible shaft has a lens with a minimum field of view of about seventy degrees.

Sinus Guide with Proximal and Distal Endoscope Channel

FIGS. 4A-5E show another embodiment of a sinus guide 12a which differs from the above-described sinus guide 12 of FIGS. 1 and 3A only in that it does not have a single continuous endoscope channel 28 that extends over its entire length, but rather a proximal endoscope channel 28p that is spaced apart from a distal endoscope channel 28d. These proximal and distal endoscope channels 28p, 28d may comprise any structure (e.g., tube, track, groove, rail, etc.) capable of guiding the advancement of an endoscope.

The proximal endoscope channel 28p extends along a proximal portion of the sinus guide body 26 and the distal endoscope channel 28d extends along a distal portion of the sinus guide body 26. The proximal channel 28p and distal channel 28d are oriented at an angle relative to one another such that there is an angle A between the respective longitudinal axes of the two channels. Also, this sinus guide 12a may optionally include a longitudinally moveable sheath 61 which is moveable from a retracted position (Shown in FIGS. 5A and 5D described below) and an extended position (shown in FIG. 5C described below). In the Figs., this embodiment of the sinus guide 12a is shown without a rotation grip 60. However, such rotation grip 60 may be included in this and all other embodiments. If a rotation grip 60 is included, the moveable sheath 61 will be positioned over such rotation grip 60, or located distally of the distal edge of the rotation grip 60, when the sheath 61 is in its retracted position.

FIGS. 5A-5C show a method for loading the flexible fiber endoscope 30 into this embodiment. As seen in FIG. 5A, with the optional moveable sheath 61 in a retracted position, the flexible fiber endoscope 30 is advanced through the proximal endoscope channel 28p such that its distal end emerges out of the distal end of the proximal endoscope channel 28p. Thereafter, as seen in FIG. 5B, the distal end of the flexible fiber endoscope 30 may be grasped, pulled in the distal direction and oriented at an angle with a gentle curve in the flexible endoscope and the distal most portion of the flexible endoscope being straight so that the fragile lens in the distal most portion of the flexible endoscope is not broken or damaged, but will facilitate insertion of the distal end of the flexible fiber endoscope 30 into or through the distal endoscope channel 28d. With the flexible fiber endoscope 30 so oriented, it is inserted into or through the distal endoscope channel 28d, as shown. Then, as seen in FIG. 5C, the optional moveable sheath 61 (if present) is moved to its advanced position so as to compress any slack in the flexible endoscope 30 and to hold a portion of the flexible endoscope 30 between the proximal endoscope channel 28p and the distal endoscope channel 28p in juxtaposition to the adjacent sinus guide body 26.

Figure 5:
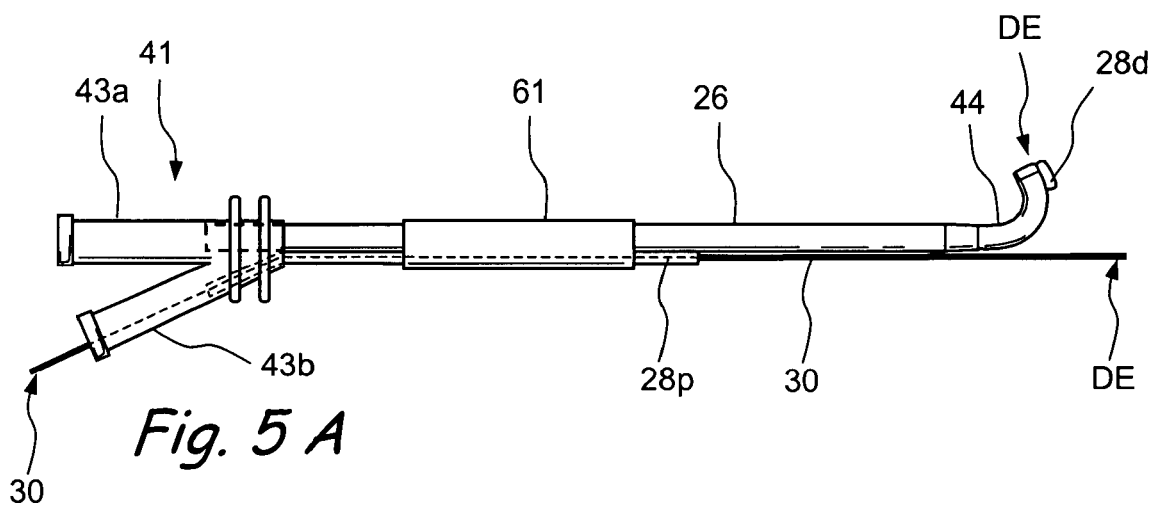
FIGS. 5A-5C show steps in a method for using a flexible endoscope in conjunction with the guide catheter component of FIG. 4A.
FIG. 5D shows one embodiment of a fixture apparatus that is useable to facilitate passage of a flexible endoscope through the distal endoscope guide lumen of the guide catheter of FIG. 4A.
FIG. 5E shows another embodiment of a fixture apparatus that is useable to facilitate passage of a flexible endoscope through the distal endoscope guide lumen of the guide catheter of FIG. 4A.
Figure 5:
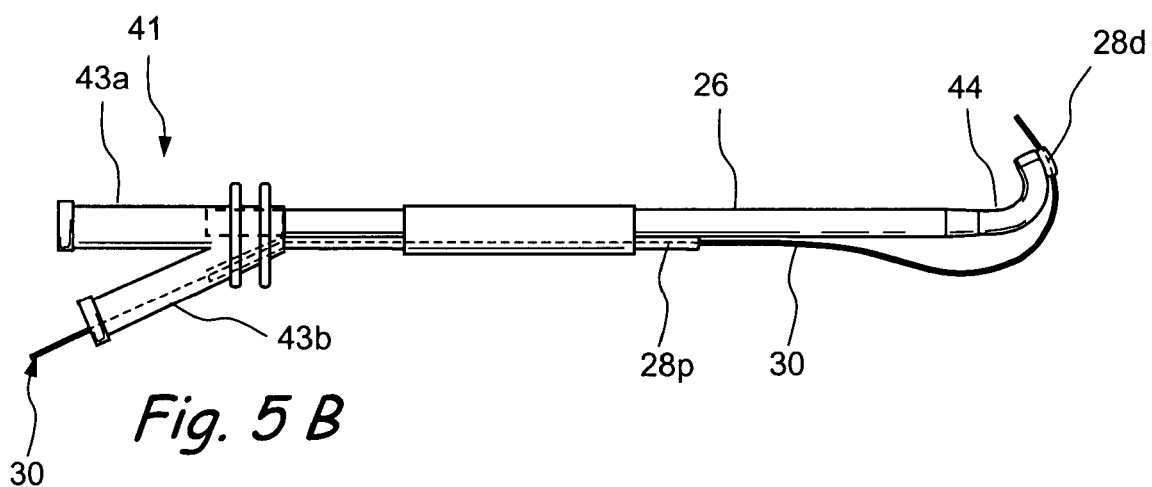
Figure 5:
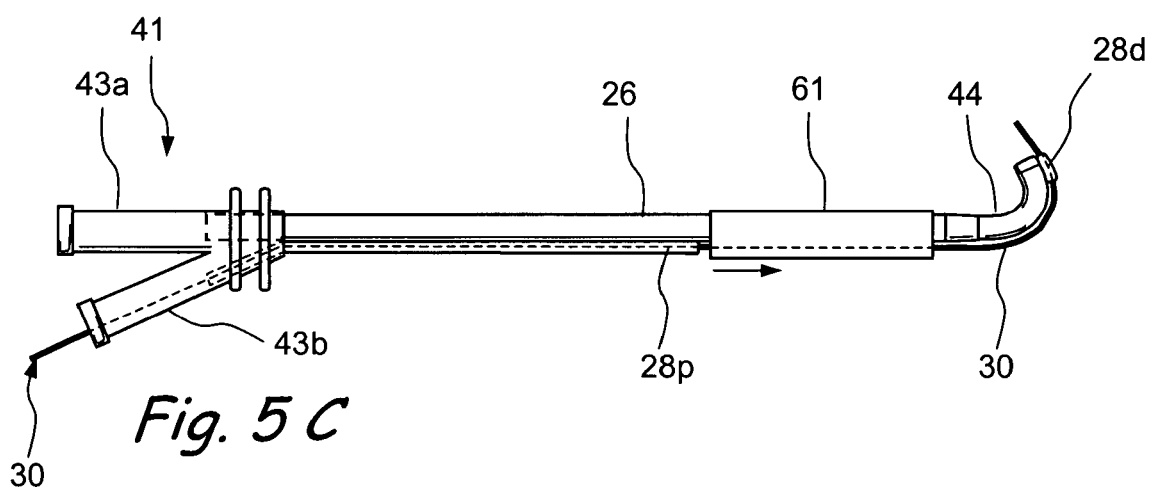
Figure 5D:
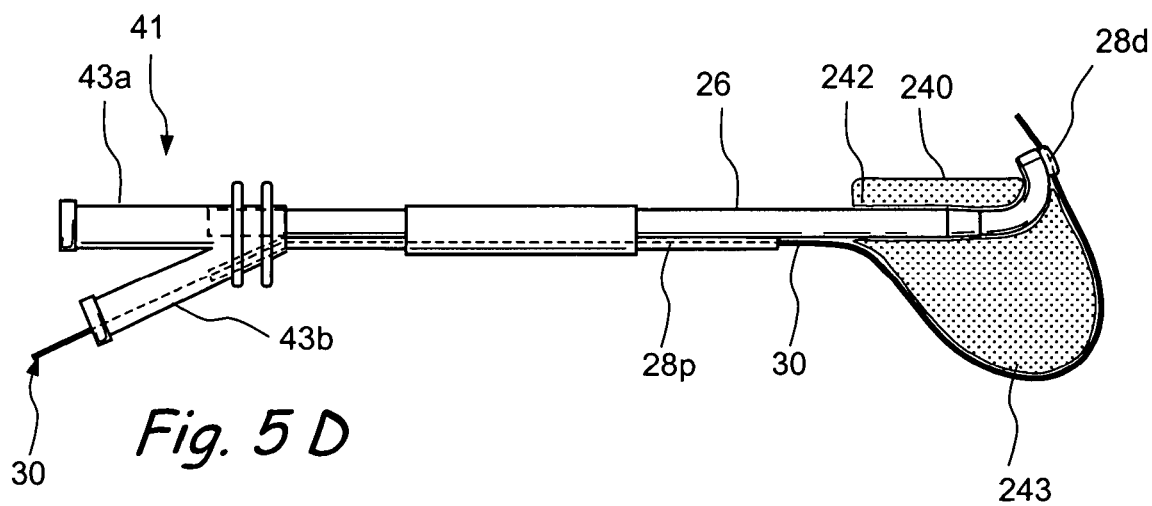
Figure 5E:
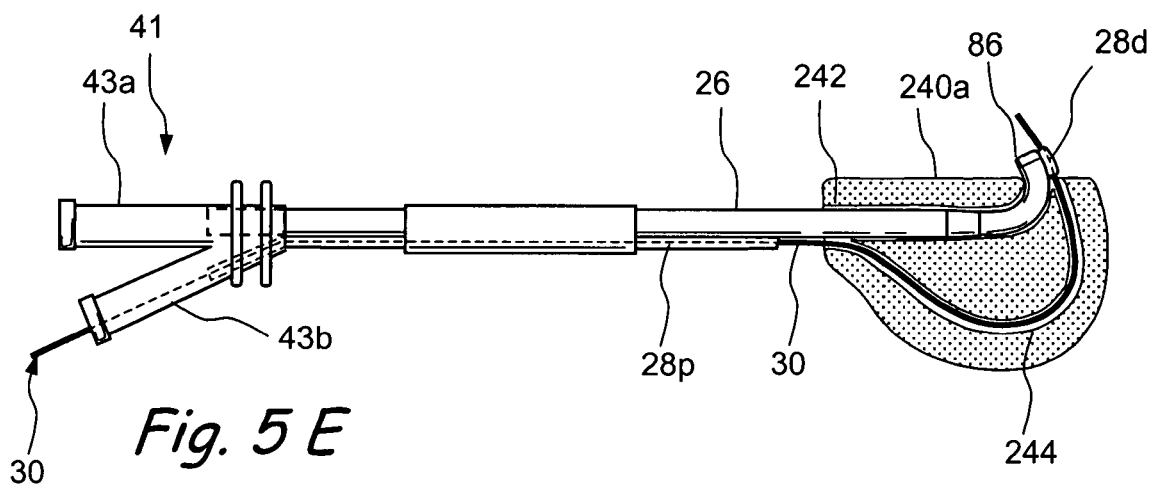

FIGS. 5D and 5E show fixture devices 240, 240a that may be used during loading of the flexible endoscope 30 to ensure that the distal end of the flexible endoscope 30 is oriented at an angle that will facilitate insertion into or through the distal endoscope channel 28d, while at the same time protecting the lens in the distal most portion of the flexible endoscope 30.

In FIG. 5D, the fixture device 240 comprises a rigid body formed of suitable material, such as molded plastic. A groove 242, shaped to correspond to a distal portion of the sinus guide device 12, is formed in the upper surface of the fixture device 240. The outer edge 243 of the fixture device 240 is shaped such that, when the endoscope 30 is extended along and in contact with such edge 243, the distal end of the endoscope 30 will be in an orientation that facilitates its passage into or through the distal endoscope channel 28d. After the distal end of the endoscope 30 has been successfully passed into or through the distal endoscope channel 28d, the sinus guide 12a and endoscope 30 are removed from the fixture device 240, the loading of the endoscope 30 is completed in accordance with FIG. 5C described above.

FIG. 5E shows another fixture device 240a which is substantially same as the fixture device 240 shown in FIG. 5D, but wherein an endoscope receiving groove 244 is also formed in the upper surface of the fixture device 240. This endoscope receiving groove 244 is shaped such that, when the endoscope 30 is placed in groove 244, the distal end of the endoscope 30 will be in an orientation that facilitates its passage into or through the distal endoscope channel 28d.

Optional Linkage of Endoscope to Working Device

Figure 6:
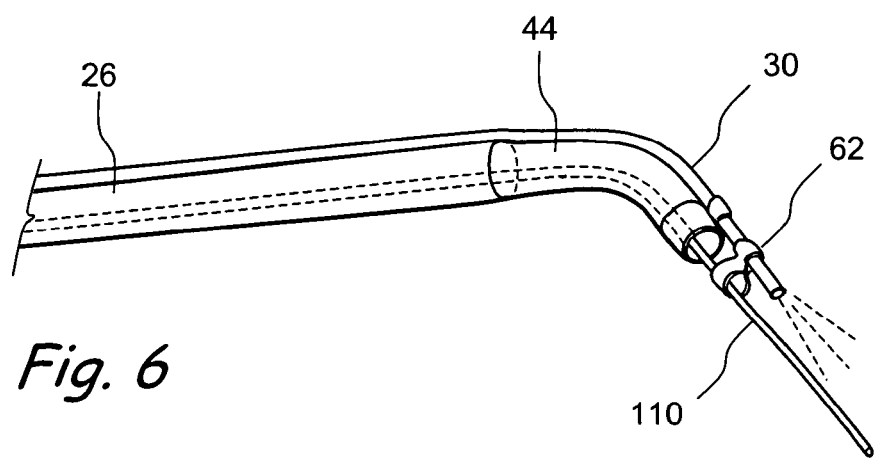
FIG. 6 is a partial perspective view of a guide catheter of the present invention with an optional linking apparatus for linking the endoscope to a guidewire to deter divergence of the endoscope away from the path of the guidewire.

In some applications, it may be desirable to advance the flexible endoscope 30 out of and beyond the distal end of the endoscope channel 28, 28d. For example, as shown in FIG. 6, the endoscope 30 may sometimes be advanced along side a working device, such as a guidewire 110, so as to view the advancement, positioning and/or use of the working device. In such instances, it is desirable to prevent the endoscope from diverging away from the working device and/or to maintain the endoscope 30 at a specific spaced distance away from the working device. To accomplish this, an optional linkage device 62 may be used to link (e.g., couple, connect or attach) the endoscope 30 to the guidewire 110 or other working device.

Sinus Guide with Dynamic Endoscope Channel

Figure 7A:
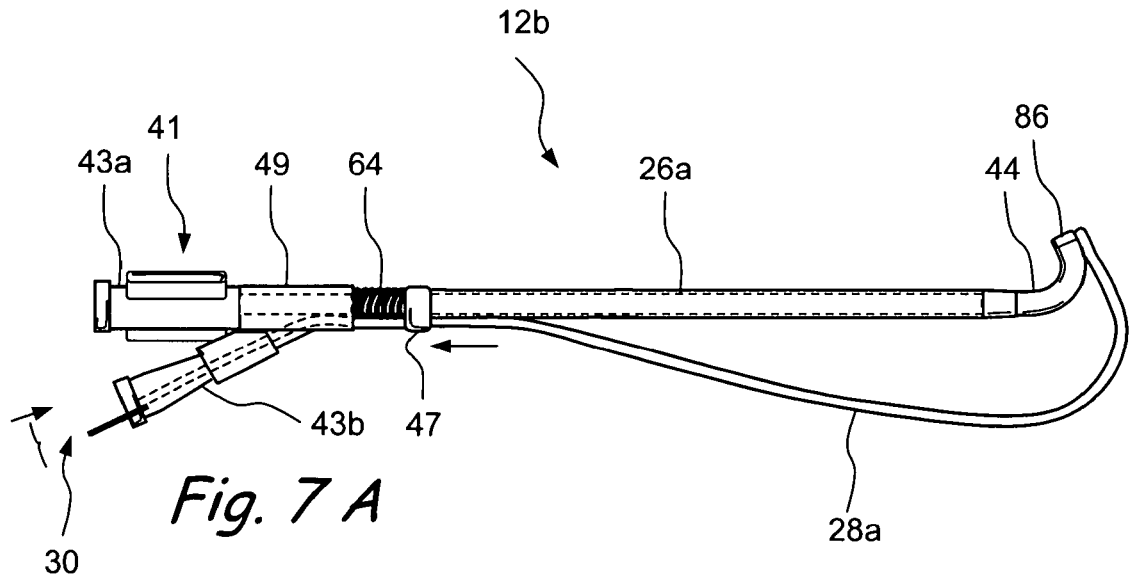
FIG. 7A shows another embodiment of a guide catheter device useable in the guide catheter systems of the present invention during insertion of a flexible endoscope into a dynamic endoscope lumen.
Figure 7B:
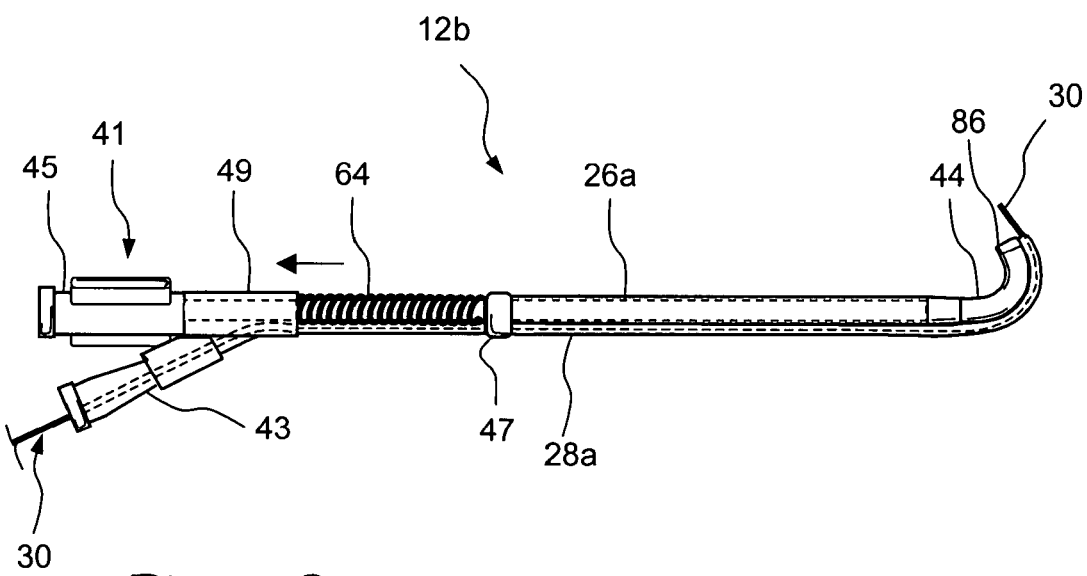
FIG. 7B shows the guide catheter device of FIG. 7A after the endoscope has been fully advanced through the dynamic endoscope lumen.

FIGS. 7A-7B show another embodiment of a sinus guide 12b which incorporates a spring loaded curved sinus guide body 26a and a dynamic endoscope channel 28a. In this example, the endoscope channel 28a comprises a flexible tube, wherein only the distal end of the dynamic endoscope channel 28a is attached to the sinus guide body 26a. A spring 64 is mounted between stop 47 and proximal sleeve 49 such that spring 64 may be compressed in the distal direction. As shown in FIG. 7A, the flexible endoscope 30 is inserted into the dynamic endoscope lumen 28a and advanced until the distal end of the endoscope begins to navigate the curve near the distal end of the device. This causes the endoscope channel 28a to deform or move outwardly and exerts distally directed pressure on spring 64, thereby compressing spring 64. As seen in FIG. 7B, as the distal end of the endoscope navigates the curve and advances to a position where it is flush with or extended out of the distal end of the endoscope channel 28a, the spring 64 will relax and the dynamic endoscope lumen 28a will return to a position where it extends along side of the sinus guide body 26, as shown.

Figure 8:
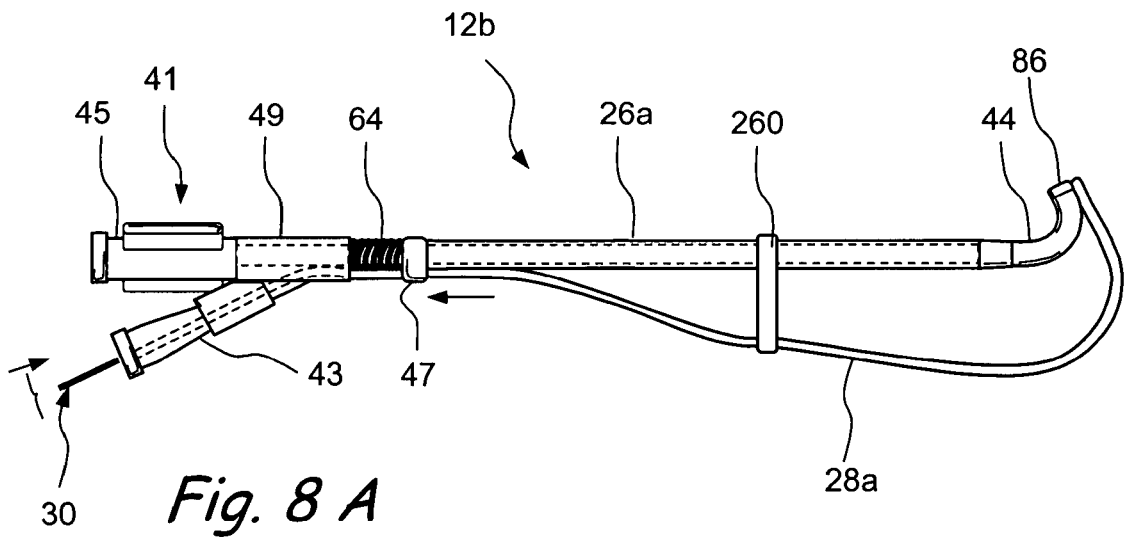
FIG. 8A shows the guide catheter device of FIG. 7A with an optional endoscope lumen retractor, during insertion of a flexible endoscope into a dynamic endoscope lumen.
FIG. 8B shows the guide catheter device of FIG. 8A after the endoscope has been fully advanced through the dynamic endoscope lumen.
Figure 8:
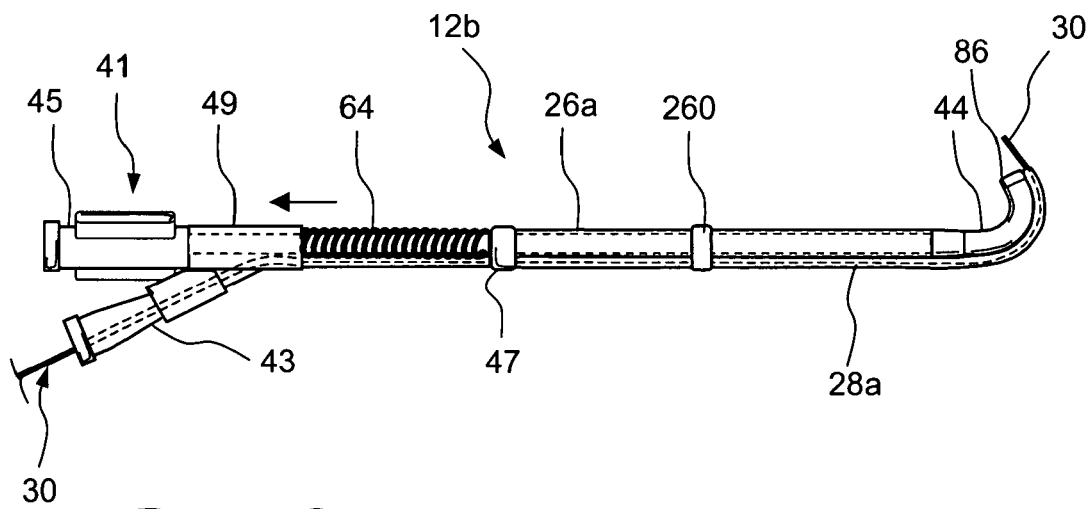

FIGS. 8A and 8B show the sinus guide 12b as seen in FIGS. 7A and 7B with the inclusion of an optional retraction member 260, such as an elastic band, to assist the dynamic endoscope channel 28a in returning to its position along side the sinus guide body 26a after the distal end of the endoscope has successfully navigated the curve.

Figure 9:
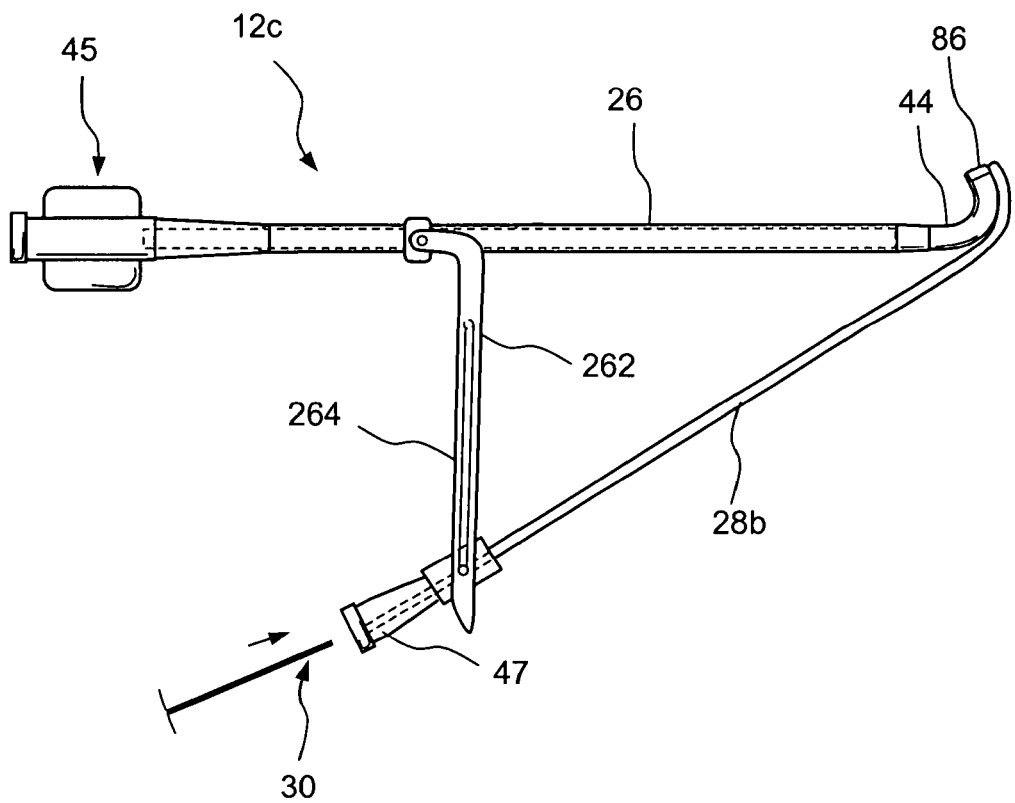
FIG. 9A shows an embodiment of a guide catheter of the present invention having a pivoting arm apparatus in an extended position to facilitate loading of an endoscope into the endoscope lumen.
FIG. 9B shows the guide catheter of FIG. 9A with the pivoting arm apparatus in a non-extended position after the endoscope has been loaded into the endoscope lumen.
Figure 9:
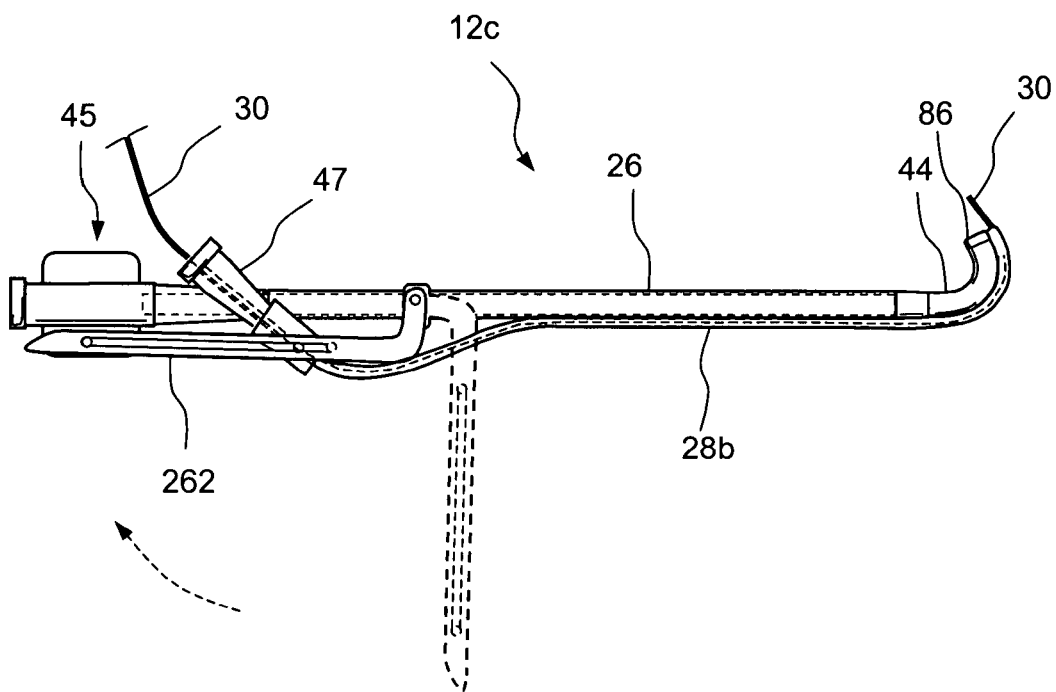

FIGS. 9A and 9B show another embodiment of a sinus guide 12c which is the same as the first embodiment 12 shown in FIG. 1 except that only a distal portion of the endoscope channel 28b is attached to the sinus guide body 26, a single female Luer hub 45 is on the proximal end of the sinus guide body and a separate single Luer hub 47 is on the proximal end of the endoscope channel 28b. A pivot arm 262 is pivotally attached to the sinus guide body 26, as shown. The proximal hub 47 of the endoscope channel 28b is slidably engaged within a spring loaded track 264 on the pivot arm. During loading of the endoscope 30, the pivot arm 262 is placed in an extended position and a spring within spring loaded track 264 causes the proximal proximal hub 47 to be located at the outer end of the spring loaded tack 264, as shown in FIG. 9A. This causes the endoscope channel 28b to be held in a position that facilitates passage of the endoscope 30 through the endoscope channel and around the curve formed near its distal end. After the endoscope 30 has been advanced around the curve, the pivot arm 262 is moved to the collapsed position shown in FIG. 9b, thereby causing the spring within the spring loaded tack 264 to compress and proximal hub 47 to move to the opposite end of spring loaded track 262. In this manner, the endoscope channel 28b extends along side of the sinus guide body 26 and the proximal hub 47 of the endoscope channel 28b is held in an accessible position adjacent to the proximal hub 45 of the sinus guide body 26.

Operation and Positioning of the Endoscope and Working Device

In the examples of sinus guides 12, 12a, 12b, 12c described above, the flexible fiber endoscope 30 may be freely advanced to or beyond the end of the sinus guide and retracted during use, in order to facilitate endoscopic viewing of the desired anatomical structures and/or to view, guide and/or verify the positioning of the sinus guide device or a working device that has been inserted through the sinus guide. The ability to advance the tip of the flexible fiber endoscope 30 beyond the end of the sinus guide allows the tip to be positioned closer to anatomy or to reach spaces in the paranasal sinuses that the sinus guide tip cannot travel to due to size constraints.

Figure 10:
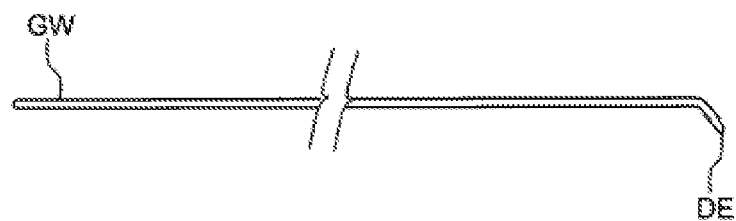
FIG. 10 is a side view of a prior art guidewire having an angled distal tip.
Figure 10:
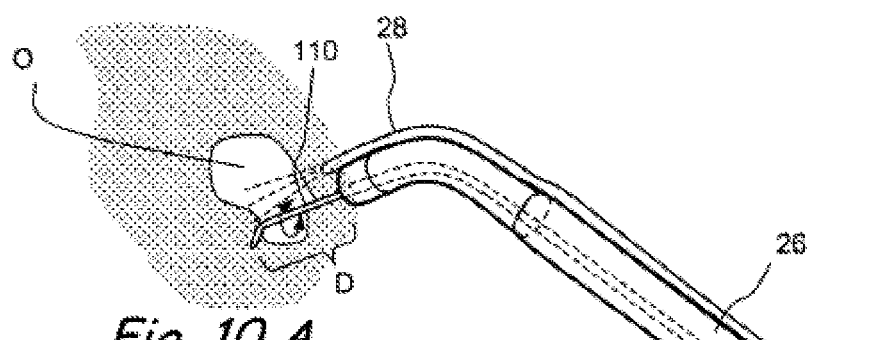
Figure 10:
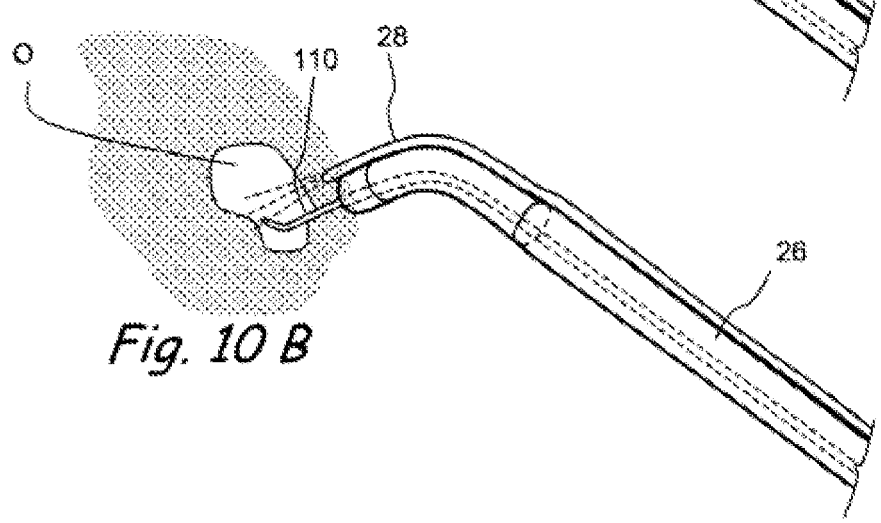

In some instances, it may be desired to advance a guidewire 110 into or through a specific body opening, such as an opening of a paranasal sinus. In such applications, as shown in FIG. 10, it is sometimes desirable to form a bend in the guidewire 110 near its distal end DE so that rotation of the guidewire in situ will redirect its distal end DE. The guidewire may be maneuvered into the opening by simply rotating the guidewire 110. FIGS. 10A and 10B show an example of such a procedure, wherein the guide device 12 is advanced to a position where its distal end is a spaced distance D from the opening O into which the guidewire 110 is to be inserted. In some instances, the user may use fluoroscopy and/or a surgical navigation system to position the guide device as described in previous applications to which this application claims priority and which have been incorporated herein by reference. With the guide device 12 so positioned, an endoscope inserted through the endoscope channel 28 may be used to view the distal end DE of the guidewire 110 as it advances out of the distal end of the sinus guide body 26. With the flexible endoscope 30 so positioned, the user has a view generally along the same axis as the distal opening of the guide device, rather than the proximal axis of the guide device. Furthermore the view can be from behind anatomy that normally would block a conventional endoscope view. In FIG. 10A, the view provided by the endoscope allows the operator to see that the distal end. of the guidewire 110 is not directed into the opening O. As a result, the operator may rotate the guidewire 110 causing its distal end DE to be directed into the opening O as verified by the view provided from the endoscope. Thus, in these sorts of applications, it is desirable to place the distal end of the sinus guide device 12 at a spaced distance D back from the opening O rather than advancing it to a point where the distal end of the sinus guide body is immediately adjacent to or within the opening O. In an alternative embodiment, the guidewire can be an illuminating guidewire as described in co-pending application Ser. No. 11/522,497, titled "Methods and Devices for Facilitating Visualization in a Surgical Environment", filed Sep. 15, 2006, now U.S. Pat. No. 7,559,925, issued Jul. 14, 2009, which was incorporated by reference above, in its entirety, and/or as described in the following section.

Illuminating Guidewire

Figure 12A:
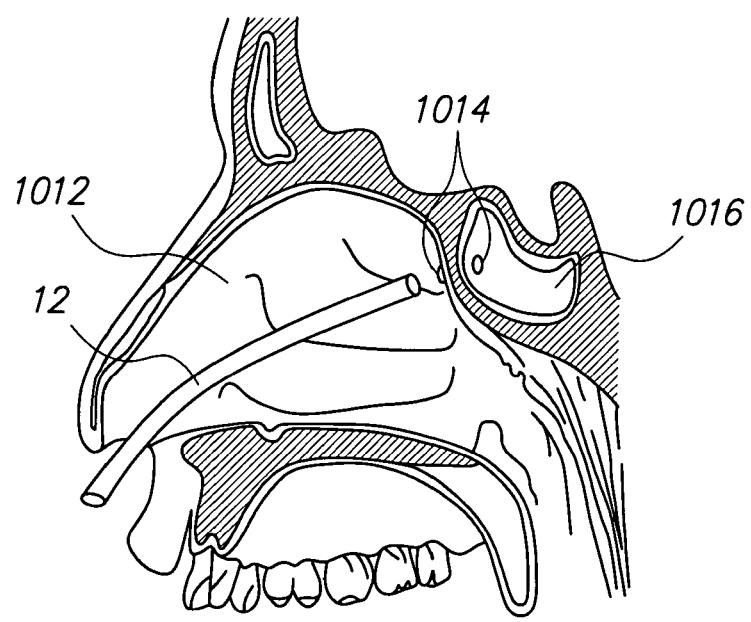
FIGS. 12A through 12D are illustrations of partial sagittal sectional views through a human head showing various steps of a method of gaining access to a paranasal sinus using a sinus guide.

FIGS. 12A through 12D are illustrations of partial sagittal sectional views through a human head showing various steps of a method of gaining access to a paranasal sinus using a sinus guide. In FIG. 12A, a first introducing device in the form of a sinus guide 12 is introduced through a nostril and through a nasal cavity 1012 to a location close to an ostium 1014 of a sphenoid sinus 1016. Sinus guide 12 may be straight, malleable, or it may incorporate one or more preformed curves or bends as further described above, as well as in U.S. Patent Publication Nos. 2006/004323; 2006/0063973; and 2006/0095066, now U.S. Pat. No. 7,462,175, issued Dec. 9, 2008, for example, each of which are incorporated herein, in their entireties, by reference thereto. In embodiments where sinus guide 12 is curved or bent, the deflection angle of the curve or bend may be in the range of up to about 135 degrees.

Figure 12B:
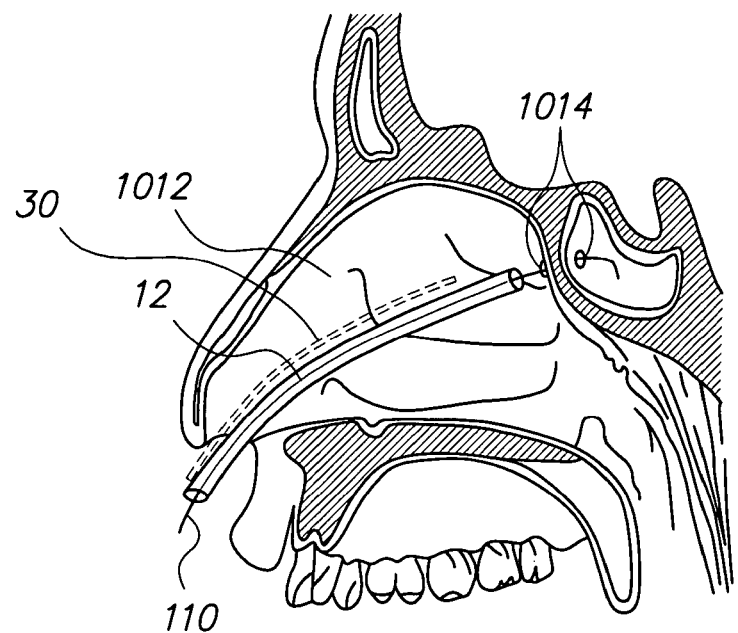

In FIG. 12B, a second introduction device comprising a guidewire 110 is introduced through the first introduction device (i.e., sinus guide 12) and advanced so that the distal end portion of guidewire 110 enters the sphenoid sinus 1016 through the ostium 1014.

Figure 12C:
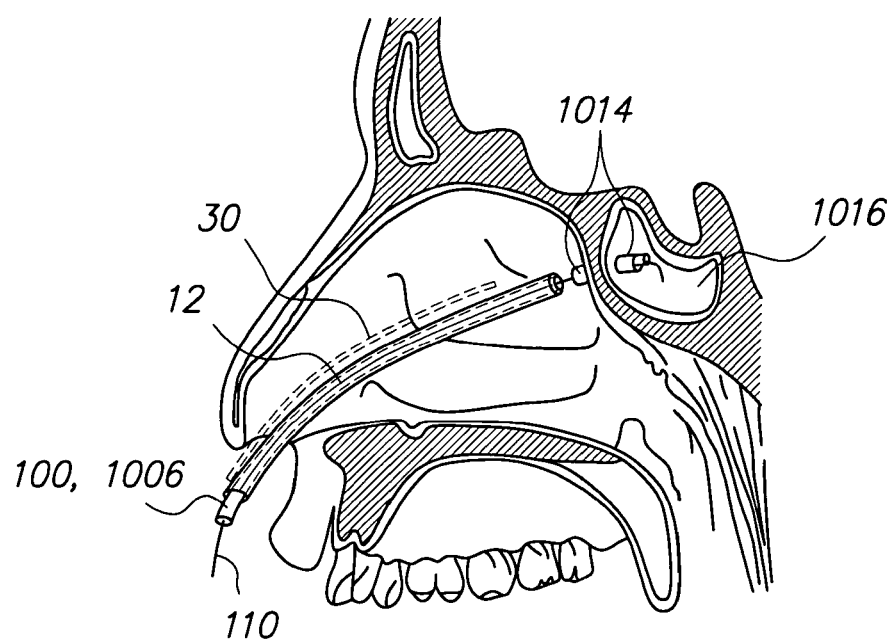
Figure 12D:
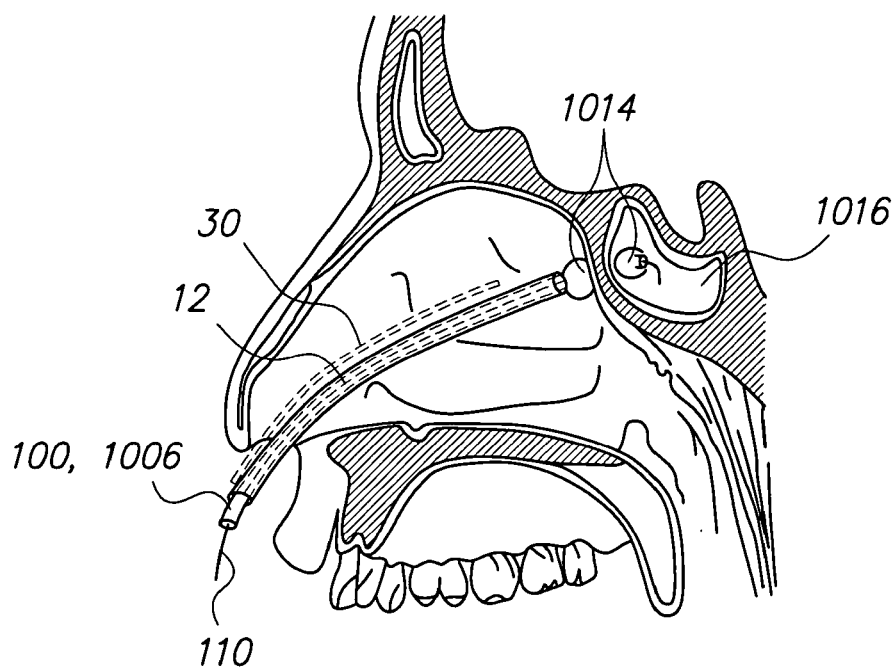

In FIG. 12C, a working device 1006, for example a balloon catheter 100, is introduced over guidewire 110 and advanced to extend the distal end portion of device 1006, 100 into the sphenoid sinus 1016. Thereafter, in FIG. 12D, working device 1006, 100 is used to perform a diagnostic or therapeutic procedure. In this particular example, the procedure is dilatation of the sphenoid sinus ostium 1014, as is illustrated in FIG. 12D, where the balloon of device 1006 is expanded to enlarge the opening of the ostium 1014. After completion of the procedure, sinus guide 12, guidewire 110 and working device 1006, 100 are withdrawn and removed. It will be appreciated that the present invention may also be used to dilate or modify any sinus ostium or other man-made or naturally occurring anatomical opening or passageway within the nose, paranasal sinuses, nasopharynx or adjacent areas. As will also be appreciated by those of ordinary skill in the art, in this or any of the procedures described in this patent application, the operator may additionally advance other types of catheters, and that guidewire 110 may be steerable (e.g. torquable, actively deformable) or shapeable or malleable.

FIGS. 12B-12D show an optional scope 30 in dotted lines, that may be inserted to provide visualization of advancement of sinus guide 12 and/or inserted alongside sinus guide 12 to provide visualization of all or at least a portion of working tool 1006, 100. It is to be appreciated that optional scope 30 may comprise any suitable types of rigid or flexible endoscope and such optional scope may be separate from or incorporated into the working devices and/or introduction devices of the present invention, as further described herein. In one preferred embodiment, endoscope 30 is a flexible fiber endoscope 30 as described herein.

Although scope 30 may be useful to reduce or eliminate the need for fluoroscopic visualization during placement of sinus guide 12 and/or for visualization of the procedure performed by working device 1006, 100, it does not provide stand-alone capability to see inside the sinus (e.g., sphenoid sinus 1016 or other sinus of interest), and therefore cannot provide sufficient visual feedback for use in guiding guidewire 110 into the desired sinus (e.g., frontal sinus, or some other sinus of interest) or sufficient visual image confirmation of correct placement of guidewire 110 into the desired sinus.

Figure 13:
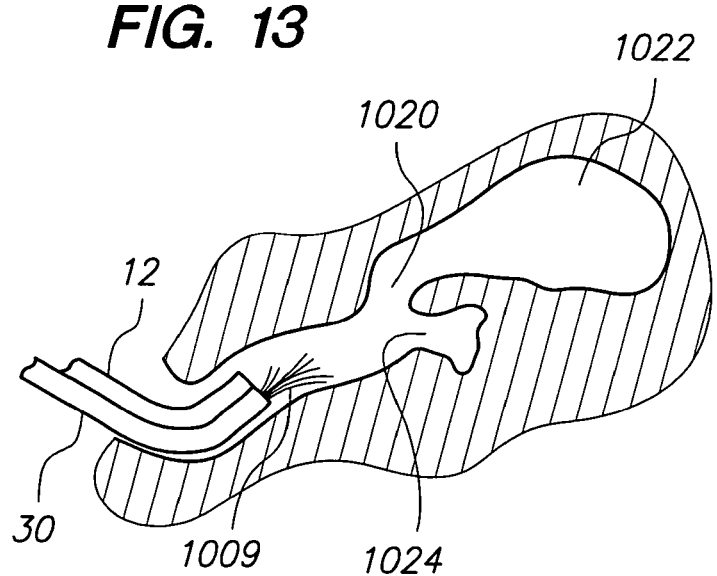
FIG. 13 illustrates a scope introduced on the side of the sinus guide.

Further, depending upon the particular configuration of the sinus passageways to be traversed to gain access to a target ostium, the scope 30, due to physical limitations (e.g., outside diameter, degree of rigidity, etc.) may be unable to visualize as deep as the location of the ostium of interest. For example, FIG. 13 illustrates a situation where scope 30 has been inserted as far as possible without causing significant trauma to the patient. The range of adequately illuminated visibility in this case does not extend all the way to ostium 1020, as indicated schematically by the rays 1009 shown extending distally from scope 30. In this case, adequately illuminated visualization of guidewire 110 into ostium 1020 would not be possible via scope 30. Additionally, if sinus guide 12 is physically capable of being extended further distally to place the distal end thereof at the approach to ostium 1020, scope 30 would also not be capable of adequately visualizing this. Thus, prior to the provision of an illuminated guidewire 11 as described herein, fluoroscopic or other x-ray visualization of these procedures was required, in order to ensure that the devices approach (and extend through) the appropriate ostium 1020 and not another adjacent opening, such as opening 1024.

In order to overcome these and other problems, the guidewire devices 110 of the present invention include their own light emitting capability. By illuminating a distal end portion of guidewire 110, a process known as transillumination occurs as guidewire 110 traverses through the sinus passageways, passes through an ostium and enters a sinus cavity. Transillumination refers to the passing of light through the walls of a body part or organ. Thus, when guidewire 110 is located in a sinus, the light emitted from guidewire 110 passes through the facial structures and appears as a glowing region on the skin (e.g., face) of the patient. It is noted that the light emitted from scope 30, such as positioned in FIG. 13, for example, results in transillumination as well, but the resultant glow is much more diffuse and larger in area. As the light source in guidewire 110 gets closer to the surface of the structure that it is inserted into (e.g., the surface of the sinus), the transillumination effect becomes brighter and more focused (i.e., smaller in area). Additionally, the movements of the guidewire 110 can be tracked by following the movements of the transillumination spot produced on the skin of the patient.

Figure 14:
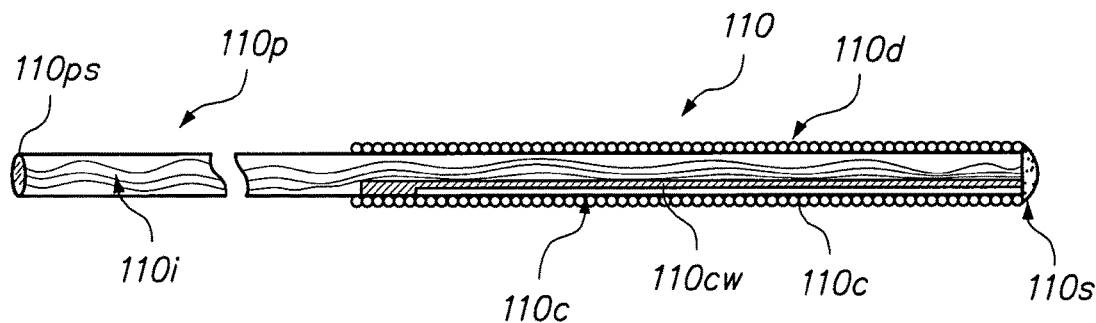
FIG. 14 shows an illuminating guidewire according to one embodiment of the present invention.

FIG. 14 shows an illuminating guidewire 110 according to one embodiment of the present invention. Device 110 includes a flexible distal end portion 110d that provides a similar degree of flexibility to a standard, non-illuminating type of guidewire. Distal end portion 110d may include a coil 110c as an exterior portion thereof, to help provide the desired flexibility to this portion. The proximal end portion 110p of device 110 extends the device to provide a sufficient length so that device 110 extends proximally out of the patient (and, when inserted through another device, such as a sinus guide, proximally out of the device into which guidewire 110 is inserted), at all times, including the deepest location into which the distal end of device 110 is placed. The proximal end portion 110p can have visible markings, preferably spaced at equal intervals, that can be observed by the user to confirm how far the guidewire 110 has been placed in the patient. Proximal end portion 110p also provides the necessary mechanical properties required to make the guidewire function properly. These mechanical properties include torquability, i.e., the ability to torque the proximal end portion 110p from a location outside of the patient and have that torque transmitted to the distal end portion 110p; pushability, i.e., sufficient rigidity, so that when an operator pushes on the proximal end portion 110p from a location outside of the patient, the pushing force transmits to the distal portion 110d to advance the distal portion 110p without buckling the device 110; and tensile strength so that an operator can pull on the proximal end portion 110p from a location outside of the patient and withdraw device 110 from the patient without significant plastic deformation or any disintegration of the device.

Coil 110c may be formed from a stainless steel wire, for example. The diameter of the coil wire can be between about 0.004 and about 0.008 inches, typically about 0.006 inches. Alternative materials from which coil 110c may be formed include, but are not limited to: ELGILOY®, CONICHROME® or other biocompatible cobalt-chromium-nickel alloy; nickel-titanium alloys, or other known biocompatible metal alloys having similar characteristics. Further alternatively, distal end portion may comprise a braided metallic construction of any of the aforementioned materials in lieu of a coil.

The external casing of the proximal portion 110p can be made from a polyimide sheath, a continuous coil (optionally embedded in polymer or having polymer laminated thereon), a hypotube (e.g., stainless steel hypotube), a laser-cut hypotube, a cable tube, or a tube made from PEBAX® (nylon resin) or other medical grade resin. In any of these cases the construction needs to meet the required torquability, pushability and tensile requirements of the device.

In the example shown, coil 110c is joined to proximal portion 110p by solder, epoxy or other adhesive or mechanical joint. One or more illumination channels 110i are provided in device 110 and extend the length thereof. Illumination channels 110i are configured to transport light from the proximal end of device 110 to and out of the distal end of device 110. In the example shown, two illumination channels are provided, each comprising a plastic illumination fiber. The plastic used to make the illumination fibers is compounded for light transmission properties according to techniques known and available in the art. As one example, ESKA™ (Mitsubishi Rayon), a high performance plastic optical fiber may be used, which has a concentric double-layer structure with high-purity polymethyl methacrylate (PMMA) core and a thin layer of specially selected transparent fluorine polymer cladding. In one example, illumination fibers each have an outside diameter of about 0.010". The illumination fibers can have an outside diameter in the range of about 0.005 inches to about 0.010 inches. Alternatively, a single plastic illumination fiber 10i may be used that has an outside diameter of about 0.020". Further alternatively, glass illumination fibers may be substituted which are much smaller in outside diameter, e.g., about 0.002". In this case, more illumination fibers may be provided in a bundle, e.g., about six to fifty glass fibers 110*i* may be provided.

The distal end of device 110 is sealed by a transparent (or translucent) seal 110*s* which may be in the form of epoxy or other transparent or translucent adhesive or sealing material. Seal 110*s* maintains the distal ends of illumination fibers 110*i* coincident with the distal end of device 110 and also provides an atraumatic tip of the device 110. Further, seal 110*s* prevents entrance of foreign materials into the device. The distal end can be designed to either focus or distribute the light as it emanates therefrom, to achieve maximum transillumination effects. In this regard, the distal end can include a lens, prism or diffracting element.

The proximal end of device 110 is also sealed by a transparent (or translucent) seal 110*ps* which may be in the form of epoxy or other transparent or translucent adhesive or sealing material. Seal 110*ps* maintains the proximal ends of illumination fibers 110*i* coincident with the proximal end of device 110. The proximal end of device 110 maybe further prepared by grinding and polishing to improve the optical properties at the interface of the proximal end of device 110 with a light source. The illumination fibers 110*i* at locations intermediate of the proximal and distal ends need not be, and typically are not fixed, since no mapping of these fibers is required, as device 110 provides only illumination, not a visualization function like that provided by an endoscope. Further, by leaving illumination fibers free to move at locations between the proximal and distal ends, this increases the overall flexibility and bendability of device 110 relative to a similar arrangement, but where the illumination fibers 110*i* are internally fixed.

The outside diameter of device 110 may be in the range of about 0.025 inches to about 0.040 inches, typically about 0.030 to 0.038 inches, and in at least one embodiment, is about 0.035"±0.005". At least the distal portion 110*p* of device 110 is provided with a core support 110*cw* that is contained therein. In the example shown in FIG. 14, core support 110*cw* is a wire that is fixed to proximal section 110*p* such as by laser welding, epoxy or other adhesive or mechanical fixture. Core support 110*cw* may extend substantially the full length of device 110. In any case, core support 110*cw* is typically formed from stainless steel NITINOL (nickel-titanium alloy) or other biocompatible nickel-titanium alloys, cobalt-chromium alloys, or other metal alloys that are biocompatible and provide the necessary rigidity and torquability. Core support 110*cw* may be formed as a wire, as in the example shown in FIG. 14, or alternatively, may be braided from any of the same materials or combination of materials mentioned above. Core support 110*cw*, when formed as a wire can be ground to different diameters to provide varying amounts of rigidity and torquability. When formed as a braid, the braid can be formed to have varying amounts of rigidity and torquability along the length thereof. For example, core wire 110*cw* has a larger outside diameter at the proximal end portion than at the distal end portion so that it is more rigid and transfers more torque from the proximal portion of device 110, whereas at the distal end portion, core 110*cw* is relatively more flexible and twistable. For core supports 110*cw* that extend through proximal portion 110*p*, the portion of core support near the proximal end of device 110 may have an even larger outside diameter.

Core support 110*cw* particularly increases the pushability and the torquability of coil 110*c* which, by itself, is quite flexible and twistable. Combined with the core support 110*cw*, the distal portion is much more effective at transferring pushing and torquing forces without buckling or twisting. Additionally, core support 110*cw* may be plastically deformed or memory set into a bent shape, an example of which is shown in FIG. 5. Bend 110*b* provides a steerability function, allowing an operator to direct the distal end of device 110 in different directions by torquing device about the longitudinal axis of the device, as indicated by the arrows in FIG. 15. In some embodiments this bending can be performed by an operator in the midst of a procedure, which can be particularly useful in combination with a scope 30, as viewing through the scope may make it apparent to the operator that the guidewire 110 needs to be inserted or directed at an angle offset from where the straight direction along the longitudinal axis of the device would direct it to. In some embodiments, the guidewire 110 does not have a core support or core wire. In these embodiments, the outer jacket (e.g., a coil, cable tube, laser-cut hypotube, braided polymer tube, etc.) provides the support for torque, pushability and tension. An advantage of not having a core wire/core support is that the full inner diameter of the guidewire is then available to be filled with illumination fibers.

Figure 16:
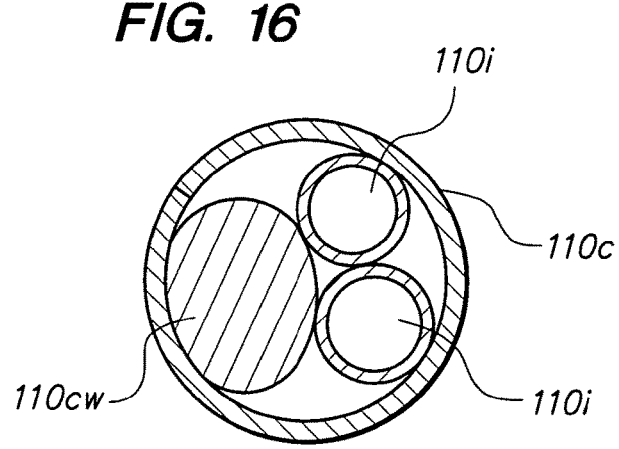
FIG. 16 is a cross-sectional illustration of a distal end portion of a guidewire device showing a core support fixed to the coil.

The illumination fibers, as noted above, can be free to move about radially within the device. Further, there is no need to center the illumination fibers 110*i* with respect to device 110 even at the distal and proximal ends of the device. FIG. 16 is a sectional illustration of a distal end portion of device 110 showing core support 110*cw* fixed to coil 110*c*, with illumination fibers 110*i* residing adjacent to core support 110*cw*, but not fixed to either core support 110*cw* or coil 110*c*.

Figure 17:
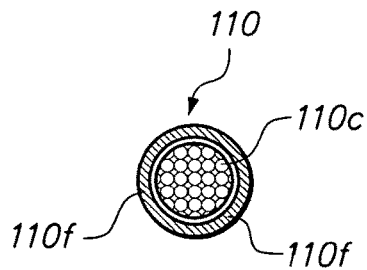
FIG. 17 shows a cross-sectional view of a guidewire device that includes a fiber optic bundle of light fibers.

The plastic or glass illumination fibers 110*i* of the device shown in FIG. 14 are typically used to transmit light from a light source such as one provided in an operating room for use by endoscopes, e.g., xenon light source, halogen light source, metal halide light source, etc. Alternatively, device 110 may be configured to transmit light from other light sources, such as a laser light source, wherein laser fibers 110*f* would be substituted for the illumination fibers described above, and extend through device 110 in a fiber optic bundle as illustrated in the cross-sectional view of FIG. 17. The fiber optic bundle, like the illumination fibers 110*i*, contributes to stiffness (in both bending and torquing motions) of device 110, thereby enhancing trackability, steering and other torquing.

Figure 18:
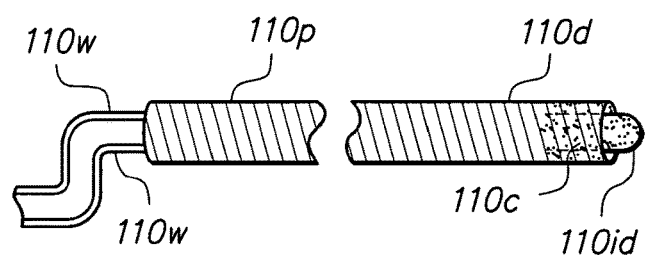
FIG. 18 shows an illuminating guidewire according to another embodiment of the present invention.

FIG. 18 illustrates another embodiment of an illuminating guidewire 110. In this example, proximal end portion of device 110 is formed externally by a coil with a polymer layer laminated thereon, but any of the other arrangements described above may be substituted. In this example, illumination is provided by a high intensity light emitting diode (LED) 110*id* fitted at the distal end of device 110. The proximal end of device 110 may be sealed such as with epoxy, or any of the other alternatives mentioned above with regard to the proximal end of device 110 in FIG. 14, in order to prevent pulling on the wires 110*iw* at the connections with LED 110*id*, as well as to seal the proximal end of the device. Grinding and polishing are not necessary, as the proximal end of device 110 in FIG. 18 does not transmit light.

Figure 19:
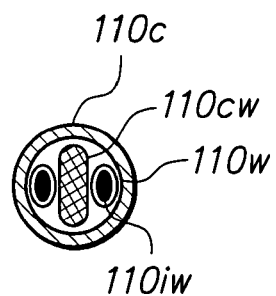
FIG. 19 is a cross-sectional illustration of a distal end portion of the guidewire shown in FIG. 18.

Device 110 in FIG. 18 performs substantially similar to the device 110 of FIG. 14 with regard to the properties of pushability, torquability and tensile properties. Device 110 of FIG. 18, however, does not require illumination fibers or laser fibers. Instead, a pair of insulated lead wires are electrically connected to the terminals of LED 110*id* (not shown) and then extend within device 110 over the length of device 110 to extend proximally from the proximal end of device 110. The free ends of wires 110w are configured to be connected to a power source that functions as the source of electrical power, to deliver electrical energy to LED 110id to illuminate it. FIG. 19 illustrates a cross-sectional view of a distal end portion of device 110 of FIG. 18. In this example, core support 110cw is in the form of a flattened distal end core wire or shaping ribbon as known in the art, that extends between the two wires 110w. FIG. 19 also illustrates the insulation layer 110iw over each wire.

Any of the devices 110 described herein may optionally include one or more radiopaque markers and/or electromagnetic coils on the tip of the device 110 and/or elsewhere along the device for enhancing visibility by fluoroscopy systems, image guided surgery (IGS) systems, or other visualization systems.

Figure 20:
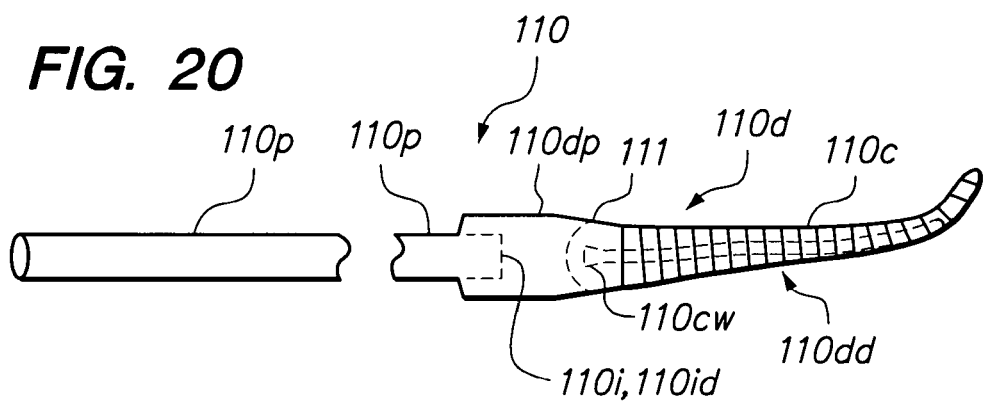
FIG. 20 shows an illuminating guidewire according to another embodiment of the present invention.

FIG. 20 shows an alternative design of device 110 in which light is emitted proximally of the distal end of the device. This configuration may employ any of the various light transmission means described above (e.g., illumination fibers, laser fibers, LED). The proximal portion 110p may be constructed in any of the manners described above with regard to other embodiments of device 110. The distal portion 110d includes a transparent proximal end portion 110dp that mounts over the distal end of proximal end portion 110p of the device 110. The transparent portion 110dp permits the illumination emitted from illumination member 110i or 110id to pass out of the device 110 at the location of transparent portion 110dp. The illumination member(s) 110i or 110id thus terminate at the proximal end portion 110dp of the distal end portion of device 110. Distally of this transparent portion 110dp, the distal portion 110dd of distal end portion 110d of device 110 extends as a floppy guidewire leader or tip. This floppy guidewire leader or tip 110dd may include a coiled section 110c and may optionally include a core support 110cw in the manner described above with regard to FIG. 14. The light emitted from illumination fibers will disperse naturally through the transparent portion 110dp. Optionally, a deflector 111, such as a convex mirror (e.g., parabolic or other convex) shape or other reflective surface may be provided distally of illumination fibers/light emitting portion 110i, 110id of device 110 to deflect light rays out of the transparent portion. Additionally, or further alternatively, illumination fibers 110i may be angled at the distal end portions thereof to direct the emitted light out through the transparent portion.

This configuration may be beneficial in further protecting the illumination emitter(s) 110i, 110id from foreign materials inside the body, as well as from trauma that may be induced by bumping the illumination emitter up against structures within the body. Further, a floppy guidewire leader 110dd of this type may provide more flexibility and maneuverability than a device in which the illumination emitter is located on the distal tip of the device.

Figure 21:
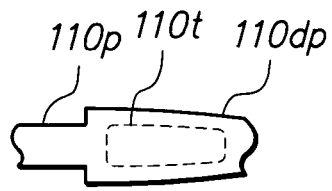
FIG. 21 illustrates an alternative transparent portion that may be included in a device shown in FIG. 20.
Figure 22:
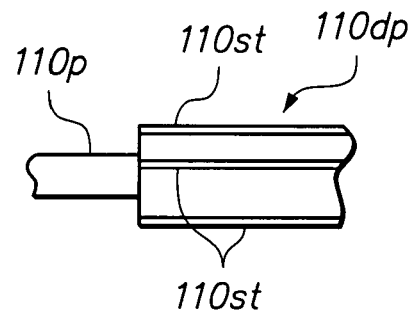
FIG. 22 illustrates another alternative transparent portion that may be included in a device shown in FIG. 20.

Transparent portion 110dp may be provided as a clear plastic or glass integral tube, or may have openings or windows 110t provided therein (see the partial view of FIG. 21). Further alternatively, transparent portion may be formed by a plurality of struts 110st circumferentially arranged to interconnect the distal floppy tip 110dd with the proximal end portion 110p of device 110 as shown in the partial illustration of FIG. 22. Alternatively members 110st may be intersecting in a criss-crossing cage like configuration or other cage configuration. In any of these alternative configurations, members 110st may be transparent, but need not be and could be formed of non-transparent materials, such as metals or opaque plastics, for example.

Device 110 should be readily connectable to and disconnectable from a power source to enable attachment for providing illumination for positioning the guidewire 110 and/or other devices during a procedure, detachment to allow another device to be slid onto the guidewire 110 from a free proximal end thereof, and reattachment to again provide illumination, to assist in guidance/visualization of the device being passed over the guidewire 110, for example.

Figure 23A:
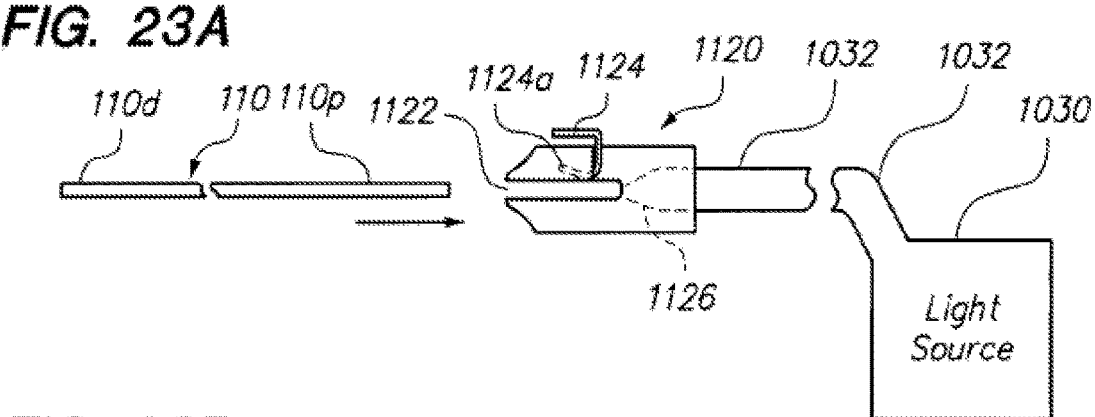
FIG. 23A illustrates an illuminating guidewire device including a quick release connector that is optically coupled to a light source.
Figure 23B:
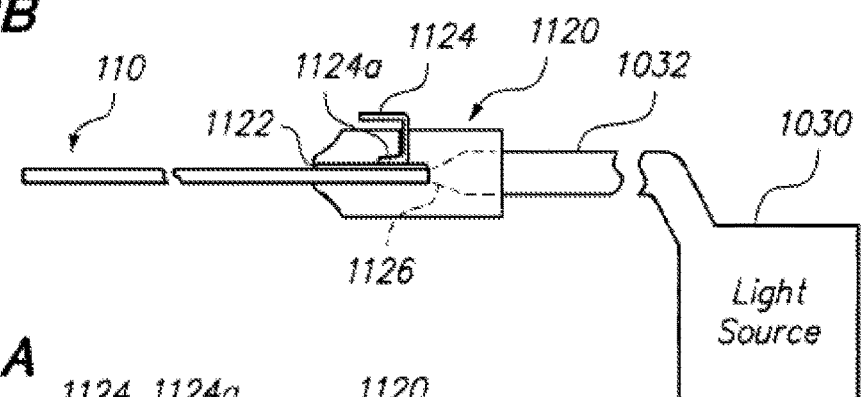
FIG. 23B is a view of the arrangement of FIG. 23A in which the quick release locking mechanism is in the locked position.

FIGS. 23A and 23B illustrate one example of a coupler or connector 1120 that is configured for quick connection and disconnection of an illumination guidewire 110 that employs illumination fibers 110i or laser fibers 110f. Coupler 1120 is connected to a light source 1030, such as a conventional endoscope light source, for example, or other light source capable of delivering preferably at least 10,000 lux through coupler 1120. Light cable 1032 optically connects connector 1120 with light source 1030 to deliver light from the light source 1030 to connector 1120. Light cable 1032 can optionally be a fluid-filled light cable, such as the type provided with DYMAX BlueWave™ 200 and ADAC Systems Cure Spot™ light cables, for example. A liquid filled light cable comprises a light conducting liquid core within plastic tubing. The liquid is non-toxic, non-flammable and transparent from 270 to 720 nm. The ends of a liquid filled light cable can be sealed with high quality quartz glass and metal spiral tubing surrounded by a plastic sleeve for exterior protection.

Connector 1120 includes a proximal channel, slot or bore 1122 that has an inside dimension or circumference that is slightly greater than the outside diameter or circumference of device 110 at the proximal end portion 110p. A quick release locking mechanism 1124 is provided for locking and unlocking device 110 within connector 1120. Quick release locking mechanism is biased toward the locking position shown in FIG. 23B, in which the locking portion 1124a of mechanism 1124 is driven into channel slot or bore 1122 and may even abut against the opposite wall of the channel, slot or bore 1122, when no guidewire 110 has been inserted. Locking mechanism 1124 may be spring-biased toward the locked position, for example. Additionally, locking mechanism 1124 may include a ball and detent arrangement, or other temporary locking means to maintain the mechanism 1124 in the locked configuration. An additional, similar mechanism may be provided to temporarily fix locking mechanism 1124 in the unlocked configuration shown in FIG. 23A. Alternative locking mechanisms may be employed, such as a pivoting lock arm, for example, that is manually pivotable between the locked and unlocked orientations, or other mechanism that would be apparent to one of ordinary skill in the mechanical arts, such as a collapsible silicone valve that grips the device, for example.

Light cable 1032 generally has a much larger inside diameter than the inside diameter or combined inside diameters of the illumination fibers 110i. Accordingly, the proximal end portion of connector 1120 provides a tapering or funnel shaped pathway 1126 having a proximal inside diameter that is substantially equivalent to the inside diameter of cable 1032 or greater, and which tapers to a distal inside diameter that is about the same or only slightly greater than the inside diameter or combined inside diameters of the illumination fiber(s), or alternatively, that is about the same or only slightly greater than the outside diameter of the proximal end of device 110. The light cable 1032 generally has a larger diameter bundle of illumination fibers than that contained within the illuminating guidewire 110. Accordingly, the taper 1126 is used to transition between the larger bundle in the light cable 1032 and the smaller bundle in the guidewire 110. With this arrangement, light delivered through light cable 1032 is concentrated or focused down to a pathway where most of the light can be transmitted through the illumination fibers.

To insert device 110 into connector 1120, an operator retracts quick connect locking mechanism 1124 to the open position shown in FIG. 23A. If quick connect mechanism 1124 is provided with a temporary locking mechanism as referred to above, then quick connect locking mechanism 1124 can be temporarily fixed in the orientation shown in FIG. 23A, without the operator having to hold it open. Otherwise, the operator will hold connector 1124 open in the position shown in FIG. 23A. The proximal end of device 110 is next inserted into the open channel, slot or bore 1122 and slid proximally with respect to connector 1120 until the proximal end of device 110 abuts against the proximal end of channel, slot or bore 1122. Quick release mechanism is next released by the operator (in embodiments when there is no temporary locking mechanism to maintain the quick release in the open configuration) or released from the temporary locked open configuration, so that the locking arm 1124a is advanced toward the proximal end portion 110p of device 110, by the biasing of quick connect locking mechanism 1124 described above. Locking arm 1124a contacts device 110 and holds device 110 under compression between locking arm 1124a and the opposite inner wall of channel, slot or bore 1122, with sufficient force to prevent device 110 from sliding out of connector 1120 even if the distal tip of device 110 is pointed straight down in a vertical direction. Optionally, locking arm 1124a may be additionally temporarily locked in place by a ball and detent mechanism, or other temporary locking mechanism, as mentioned above. To remove device 110 from connector 120, quick connect locking mechanism 1124 is repositioned to the open or unlocked orientation shown in FIG. 23A and the device is slid distally with respect to the connector until it is free from the connector 1120.

Figure 24A:
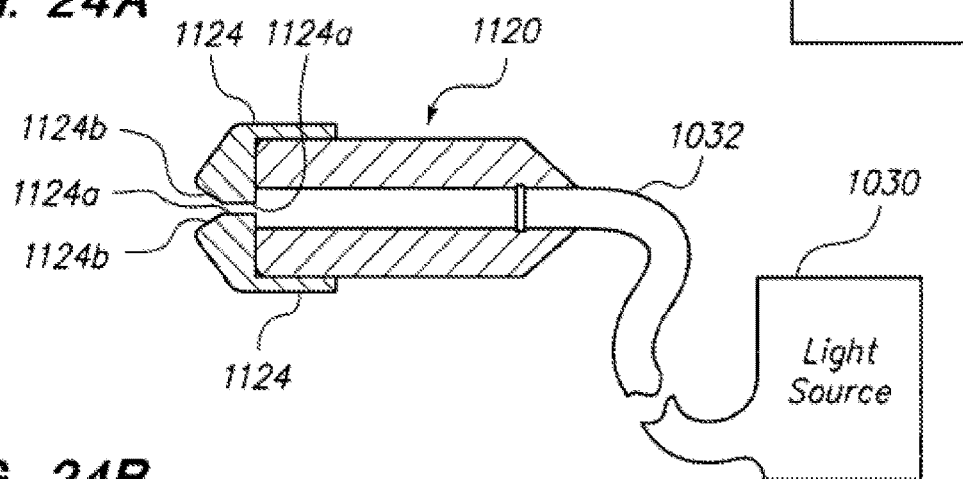
FIG. 24A illustrates an alternative quick release connector.
Figure 24B:
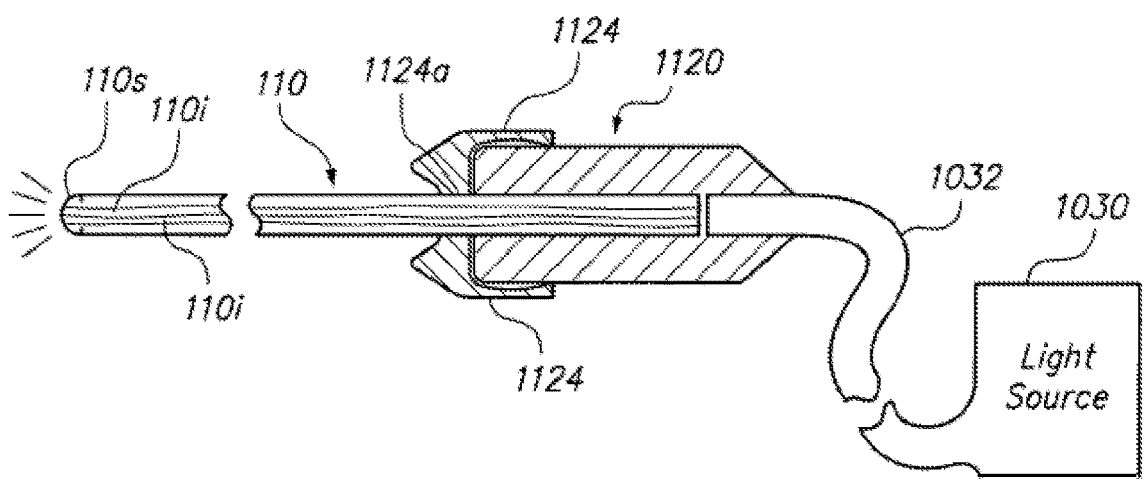
FIG. 24B illustrates the connector of FIG. 24A mounted over a proximal end portion of an illuminating guidewire.

FIGS. 24A-24B illustrate an alternative connector 1120 that includes a quick release locking mechanism 1124. In this example, two or more locking arms 1124 are provided circumferentially about the distal end of connector 1120. Arms 1124 are biased to the closed or locked configuration as shown in FIG. 24A. For example, arms 1124 may be made from resilient spring steel, nickel-titanium alloy or resilient plastic and formed to assume the configuration shown in 24A when mounted to connector 1120 and when in an unbiased state. Installation of device 110 into connector 1120 is simplified by the automatic grasping and temporary locking functions provided by quick release locking mechanism 1124. The proximal end of device 110 is simply inserted between the two or more arms 1124. Arms 1124 included ramped or cammed surfaces 1124b that guide the proximal end of device 110 into connector 1120, and, as device 110 is pushed against these surfaces 1124b, arms 1124 are deflected into the opened, biased configuration shown in FIG. 24B. The biasing/resiliency of arms 1124 imparts compressive forces to the shaft of device 110 via temporary locking surfaces 1124a, so that device 110 is gripped and held in position as shown in FIG. 24B. To remove device 110, the operator need simply pull on device 110, while holding connector 1120 relatively immobile, with a force sufficient to overcome the compressive and frictional forces imparted by surfaces 1124a. The resilient arms 1124 then return to the unbiased configuration shown in FIG. 24A. Optionally, surfaces 1124a may be coated with, or include a friction enhancing surface, such as rubber or other elastomer, and/or be roughened, such as by knurling or other surface roughening technique.

In the example shown in FIGS. 24A-24B, the light cable 1032 that is provided has an inside diameter that is about the same as the diameter of the proximal end of device 110 and thus, no tapering channel 1126 is required. However, for arrangements where the light cable 1032 is much larger, as is usually the case when using a conventional endoscope light source 1030, connector 1120 may be provided with a tapering light channel 1126 in the same manner as described above with regard to the embodiment of FIGS. 23A-23B.

Figure 25:
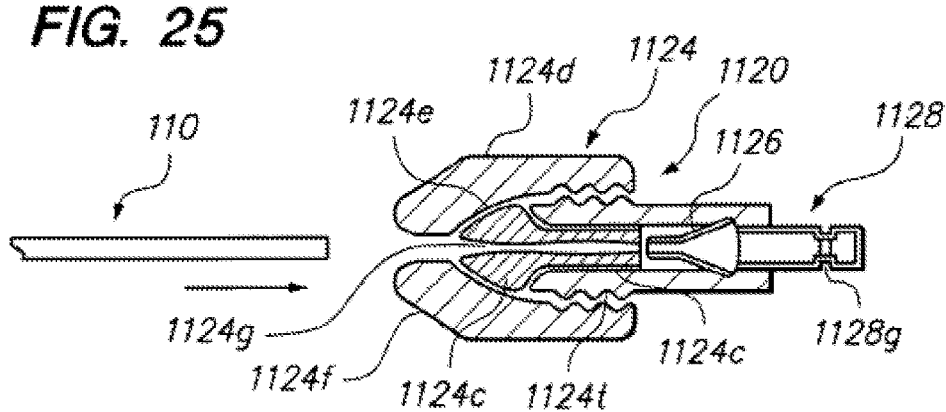
FIG. 25 illustrates another alternative quick release connector.

FIG. 25 illustrates a longitudinal sectional view of a connector 1120 that is quickly connectable and releasable from a guidewire device 110 and is also connectable to and releasable from standard light source cables that are typically found in operating rooms. Thus, this connector 1120 functions both as an adapter to connect to a conventional endoscope light source channel or cable, and as a quick release locking connector to connect to and release from a proximal end portion of guidewire 110.

The proximal end of connector 1120 is provided with a light post 1128 that is configured to mate with a connector on the distal end of a light cable extending from a conventional endoscope light source. For example, light post 1128 may be an ACMI light post (ACMI Corporation) or other standard connector typically used to connect endoscopes to operating room light sources. Because the cable extending from an operating room light source generally has a much larger inside diameter than the inside diameter or combined inside diameters of the illumination fibers of device 110, and larger than the diameter of the proximal end of guidewire 110, the proximal end portion of connector 1120 includes a light tapering or funnel-shaped pathway 1126 like that described above with regard to FIG. 23A.

The quick release locking mechanism 1124 in this example includes a collet 1124c that is configured to center the proximal end of device 110 with the distal end of tapering pathway 1126. A threaded cap 1124d is threaded over mating threads 1124t on the body of connector 1120, so that when cap 1124d is torqued in a direction to advance cap 1124d proximally with respect to the body of connector 1120, inner ramped or cammed surfaces 1124e of cap 1124d ride over outer ramped or cammed surfaces 1124f of collet 1124c, thereby functioning as a pin vise and clamping collet 1124c against the proximal end portion of device 110 to clamp and maintain device 110 in its current position relative to connector 1120. To insert device 110, cap 1124d is rotated in a reverse direction from that described above to open the distal opening of the inner channel 1124g of collet 1124c to a dimension larger than the outside diameter of the proximal end of device 110, so that device 110 can be easily slid through the channel 1124g until the proximal end of device 110 abuts the proximal end portion of collet 1124c, or approximates the same. The cap 1124d is then turned with respect to the body of connector 1120 to clamp device 110 into position, as described above. Removal of device 110 can be performed by turning cap 1124d in a reverse direction relative to connector body 1120, thereby loosening the grip of collet 1124c on device 110, after which device 110 can be easily slid out from connection with connector 1120. Components of connector 1120 may be made from metal, such as stainless steel or other biocompatible metals, or temperature-resistant thermosetting polymer, for example.

Figure 26:
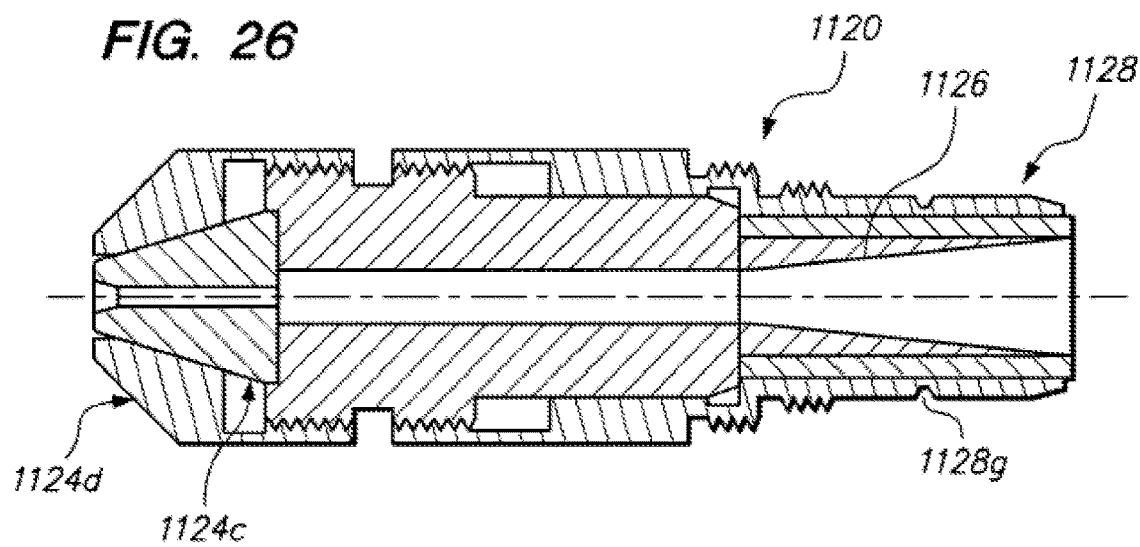
FIG. 26 illustrates another alternative quick release connector.

Light post 1128 is rotatable with respect to the light cable 1032 of the light source 1030 when connector 1120 is connected to the distal end connector of the light cable 1032. This allows device 110, when connected to connector 1120 in this arrangement, to be rotated during use without building up significant twisting or rotational counter forces within the light cable 1032. For example, in the light post 1128 shown, the female receptacle (not shown) of the light cable 1032 couples over light post 1128 and engages in groove 1128g, about which the female receptacle is then rotatable relative to light post 1128. FIG. 26 is a longitudinal sectional view of a connector 1120 that is similar to the connector 1120 described with regard to FIG. 25 above. One difference in the example of FIG. 26 is that the tapered light guide 1126 is provided in the light post 1128, as contrasted with being provided in the proximal end portion of the main body of connector 1120 in FIG. 25. However, in both cases, the function is the same.

Turning now to FIGS. 27A-27E, illustrations of partial coronal sectional views through a human head showing various steps of a method for treating an ostium that opens to a frontal sinus are shown. The methods described here, and all other methods disclosed herein may also comprise a step of cleaning or lavaging anatomy within the nose, paranasal sinus, nasopharynx or nearby structures including but not limited to irrigating and suctioning. The step of cleaning the target anatomy can be performed before and/or after a diagnostic or therapeutic procedure. The methods of the present invention may also include one or more preparatory steps for preparing the nose, paranasal sinus, nasopharynx or nearby structures for the procedure, such as spraying or lavaging with a vasoconstricting agent (e.g., 0.025-0.5% phenylephyrine or Oxymetazoline hydrochloride (Neosynephrine or Afrin) to cause shrinkage of the nasal tissues, an antibacterial agent (e.g., provodine iodine (Betadine), etc. to cleanse the tissues, etc.

Figure 27A:
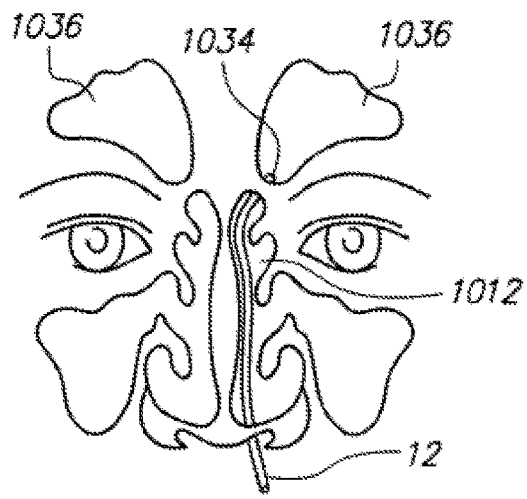
FIGS. 27A-27E are illustrations of partial coronal sectional views through a human head showing various steps of a method for treating an ostium that opens to a frontal sinus.

In FIG. 27A, a first introducing device in the form of a sinus guide 12 is introduced through a nostril and through a nasal cavity 1012 to a location close to an ostium 1034 of a frontal sinus 1036. Sinus guide 12 may be as described previously herein, or as described in the applications incorporated herein by reference. The advancement of sinus guide 12 can be visualized with a scope inserted into the nasal cavity 1012 and advanced as close to the ostium 1034 as possible without causing significant trauma to the tissues therein.

Figure 27B:
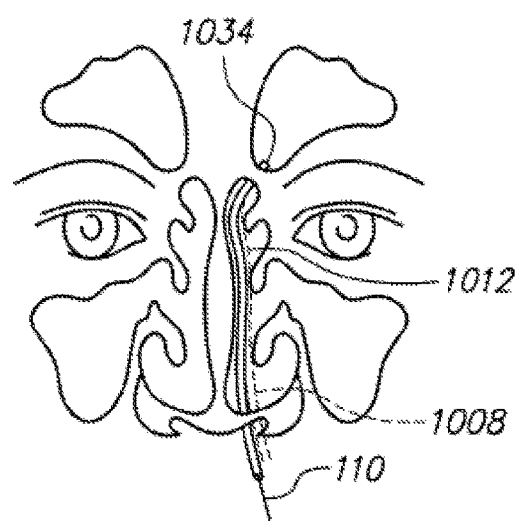

Once the surgeon is satisfied that the distal end of the sinus guide 12 is positioned close enough to the appropriate ostium 1034, illuminating guidewire 110, connected to a light source as described by any of the techniques mentioned above, is inserted through sinus guide 12 and advanced therethrough, see FIG. 27B. There may be some transillumination from the light emitted from the scope which can be used to confirm that the sinus guide 12 is positioned in the correct general area, which confirmation can be made even before the distal tip of guidewire 110 exits the distal end of sinus guide 12. However, much more specific transillumination effects are produced when the tip of guidewire 110 exits the distal end of guide 12 and especially when the light emitting portion of guidewire 110 touches or approximates an intended target surface, such as an inner wall of a sinus, for example. As the guidewire 110 is advanced, transillumination on the face of the patient can be observed as a glowing spot that moves as the distal end portion of device 110 moves, thereby making it possible to visibly track the location of the light emitting portion of device 110 without the need to use radiographic imaging, such as by fluoroscopy, for example.

Figure 27C:
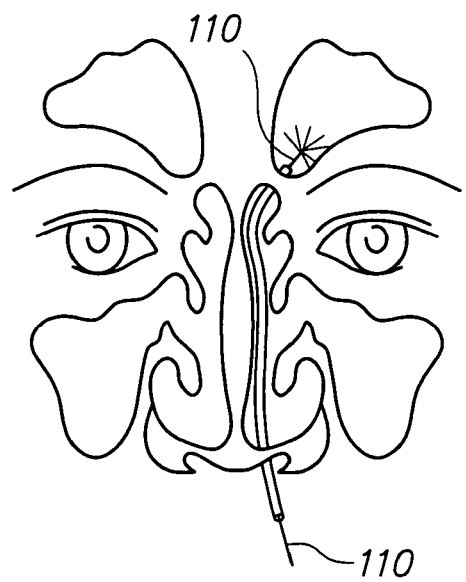
Figure 27D:
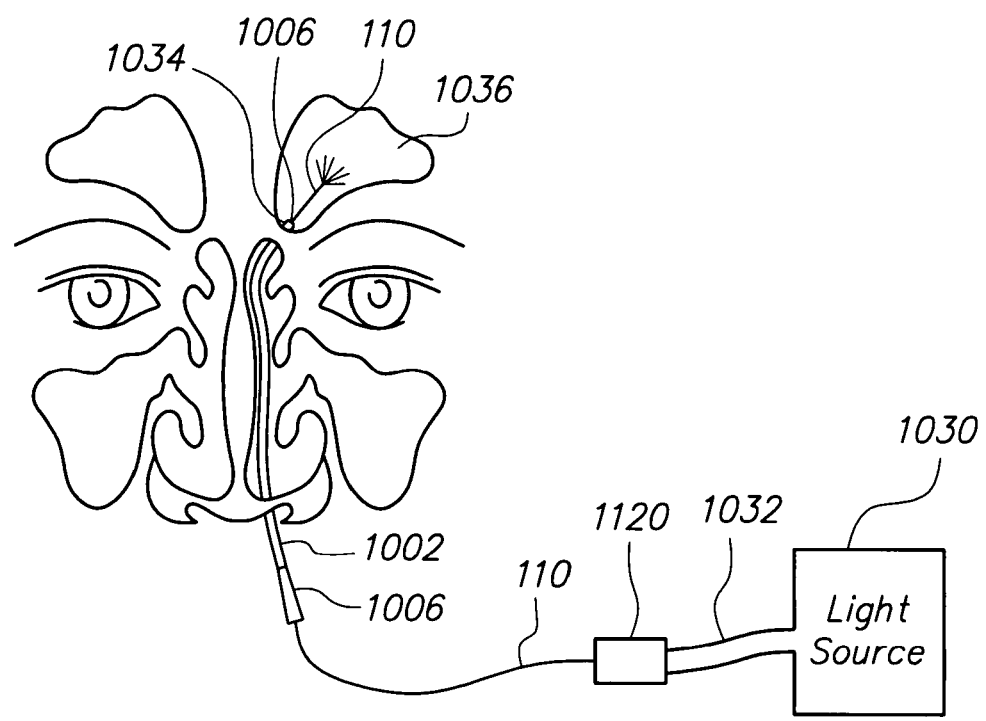
Figure 27E:
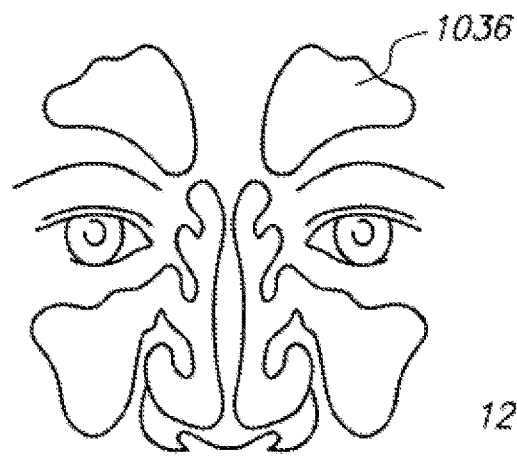

While there may be some diffuse transillumination on the forehead of the patient overlying the frontal sinus 1036 as the light emitting portion of device 110 approaches the ostium 1034, the glow on the forehead becomes brighter and smaller in dimension (more focused) as the light emitting portion passes through the ostium 1034 and enters the frontal sinus 1036, FIG. 27C. As device 110 is further advanced, the glowing spot becomes most defined and brightest as the light emitting portion approaches and contacts a wall of the frontal sinus 1036. Further, as noted, the movement of the transilluminated spot can be visibly followed to confirm that the guidewire 110 is indeed moving within the location of the frontal sinus, as can be confirmed by the surgeon's knowledge of the particular anatomy of the patient being treated. In this regard, a CAT scan or other image of the sinus anatomy can be performed prior to this procedure and studied by the surgeon, to apprise the surgeon of any distinctive or unusual patterns in the individual patient's sinus anatomy which might be useful in tracking and confirmation of where the guidewire is located, as indicated by the transillumination.

Once properly positioned, the proximal end of device 110 is disconnected from connector 1120, while leaving guidewire 110 in its current position. A working device 1006, for example a balloon catheter 100, is the introduced over guidewire 110 and advanced thereover so that the proximal end of device 110 extends proximally beyond a proximal end of device 1006, 100. Device 110 is then reconnected to connector 1120 so that light is again emitted from the light emission portion of the distal end portion of device 110. Thus it can be visually confirmed, without radiography, that the distal end portion of the guidewire 110 remains properly in the frontal sinus 1036 as the working device 1006, 100 is advanced toward ostium 1034 and the balloon of balloon catheter 100 is extended across the ostium, FIG. 27D. The proper positioning of the working end (distal end portion) of working device 1006, 100 can be visualized with the scope and/or fluoroscopy.

Once proper placement of the working device 1006, 100 has been confirmed, working device 1006, 100 is used to perform a diagnostic or therapeutic procedure. In this particular example, the procedure is dilatation of the frontal sinus ostium 1034 by expansion of the balloon of balloon catheter 100 thereagainst, to enlarge the opening of the ostium 1034. However, it will be appreciated that the present invention may also be used to dilate or modify any sinus ostium or other man-made or naturally occurring anatomical opening or passageway within the nose, paranasal sinuses, nasopharynx or adjacent areas. Further, other working tools 1006 may be inserted and used according to these same techniques. After the completion of the procedure, sinus guide 12, guidewire 110 and working device 1006, 100 are withdrawn and removed, completing the procedure, see FIG. 27E.

Figure 28:
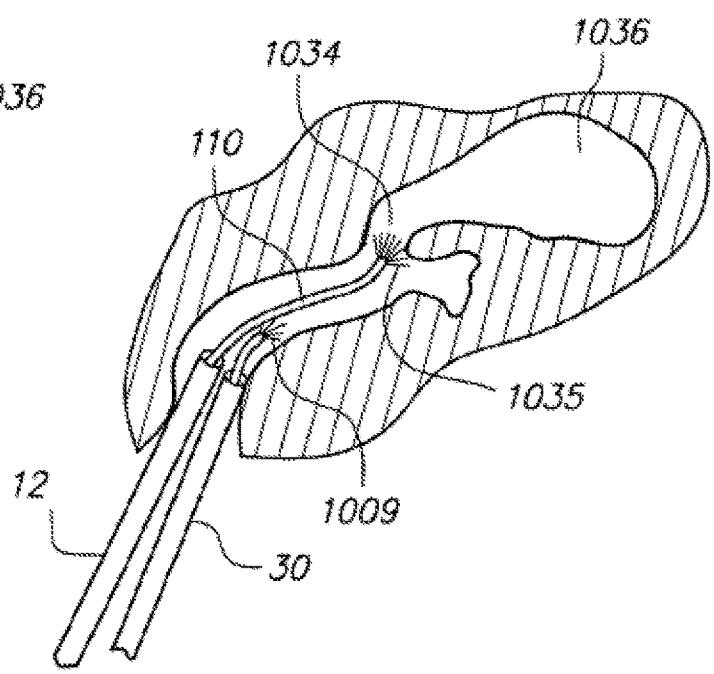
FIG. 28 illustrates a situation, like that described with regard to FIG. 13, where a scope has been inserted as far as possible without causing significant trauma to the patient. Additionally.

Illuminating guidewire device 110 can also be used to facilitate visualization and placement of the sinus guide 12 in the procedure described above with regard to FIGS. 27A-27E, or in another procedure in which a sinus guide, sinus guide or guide tube is placed in the sinus pathways. FIG. 28 illustrates a situation, like that described above with regard to FIG. 13, where scope 30 has been inserted as far as possible without causing significant trauma to the patient. The range of visibility in this case does not extend all the way to ostium 1034, as indicated schematically by the rays 1009 shown extending distally from scope 30. In this case, adequate visualization of sinus guide 12 by scope 30 is possible only up to the extent of the rays 1009 shown. Thus, if sinus guide 12 is flexible enough to be advanced more closely to ostium 1034, then adequate visualization of this movement would not be possible via scope 30. That is, if sinus guide 12 is physically capable of being extended further distally to place the distal end thereof at the approach to ostium 1034, scope 30 would not be capable of adequately visualizing this. However, by inserting illuminating guidewire 110 through sinus guide 12 as shown in FIG. 28, additional illumination can be provided distally of the illuminating range of scope 30. This additional illumination can be received by scope 30 to enable visualization up to the illumination portion of device 110 and potentially even extending to illumination range of device 110, as long as there is a straight pathway of the field of view. Thus, advancement of the sinus guide 12 can be visualized further distally by the scope 30 using this technique, and potentially all the way up to the ostium 1034.

Additionally, this technique can be used to visualize placement of the guidewire 110 up to and into the desired ostium 1034. Alternatively, this can be carried out without the sinus guide 12, wherein the guidewire 110 is inserted and the scope 30 can be used to visualize placement of guidewire 110 into the target ostium with the assistance of the light emitted by the scope 30 in addition to the light emitted by guidewire 110.

In any of these procedures where a scope 30 is used for visualization and an illuminating guidewire 110 is inserted, some transillumination of the target sinus may occur from the light emitted by the scope 30 alone. However, this transillumination will be diffuse and show a rather dim, large area of transillumination on the patient's skin. When the illumination guidewire 110 is inserted and advanced, as noted earlier, a smaller, brighter transillumination spot will be visible when the illuminating portion of the guidewire has entered the sinus. Additionally, even before entering the sinus, the light emitted from the guidewire 110 will produce a moving transillumination spot as guidewire 110 is advanced, which also helps distinguish the location of the distal portion of the guidewire 110, relative to any diffuse transillumination produced by the scope light.

If the guidewire 110 is advanced into an ostium other than the target ostium (e.g., ostium 1035 shown in FIG. 28), this may be possible to be viewed by scope 30, depending upon the line of sight. However, even if it is not, the transillumination resulting from entrance into a different sinus than the target sinus will be evident by the different location on the patient's face. Also, in the example shown, guidewire 110 would not be able to be advanced very far through ostium 135 before it was diverted and curled by the relatively small sinus space that ostium 135 leads into. Thus, by tracking the movement of the illumination spot produced by guidewire 110, the surgeon could confirm that guidewire 110 was misplaced as the guidewire would be diverted by a much smaller space then that characterized by the target frontal sinus 1036.

Thus, by using an illuminating guidewire device 110 in the methods as described above, the use of fluoroscopy or other X-ray visualization can be reduced as it is not required to confirm proper placement of the guidewire in some cases.

Similar procedures may be carried out in other sinuses. For example, a similar procedure to that described above with regard to FIGS. 27A-27E may be carried out to open or expand an opening of an ostium leading to a maxillary sinus. In this case, when illuminating guidewire device 110 passes through the ostium that opens to the target maxillary sinus and enters the maxillary sinus, a relatively bright, relatively small, defined transillumination spot can be observed to move across the cheek region of the patient. As guidewire 110 is advanced further distally along the maxillary sinus, the maxillary sinus typically tends to track in an inferior direction relative to the skull, and the bottom wall of the maxillary sinus is very close to the palate of the patient. Therefore as the illuminating portion of guidewire approaches and/or touches the bottom wall of the maxillary sinus, a transillumination spot can be observed on the roof of the patient's mouth by looking into the mouth of the patient. At the same time, the transillumination spot on the cheek that was caused by the guidewire will diminish, or not be visible at all at this time. This viewability on the roof of the mouth is further confirmation that the guidewire has entered the maxillary sinus. Movement of the transillumination spot on the roof of the mouth can also be observed as the guidewire 110 is advanced and/or retracted.

Figure 29:
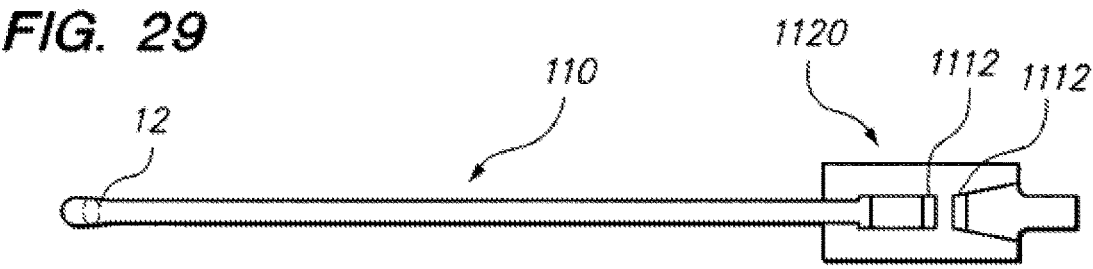
FIG. 29 illustrates non-limiting examples of where one or more filters may be placed in an illuminating guidewire device.

It is further noted that some wavelengths of light may be more effective in producing the transillumination effects described herein, for the purpose of locating the position of the guidewire. In this regard, particular wavelengths of visible light can be selected for this purpose. Alternatively, or in addition, infrared wavelengths may be particularly effective. In this regard, guidewires that employ illuminating fibers may be provided with a filter 1112 to define the color/wavelength of the light emitted by device 110. As schematically shown in FIG. 29, filter 1112 may be provided distally of the illumination fibers, such as at the distal tip of device 110, proximally of the illumination fibers, such as at the proximal end of device 110, or in the light pathway at a location within connector 1120, for example. Multiple filters may be placed at one or more of these locations. For devices 110 that employ an LED light emitting component, different color LEDs may be employed to emit different wavelengths of light. For devices 110 that employ laser fibers, different types of lasers may be used that emit different wavelengths of light.

Figure 30A:
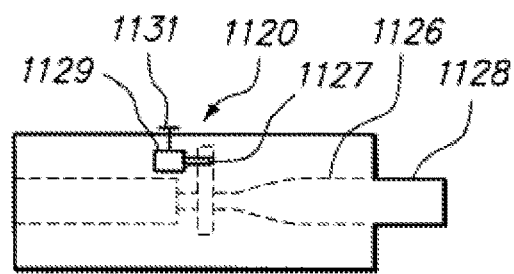
FIG. 30A schematically illustrates a connector having a rotating shutter rotatably mounted therein.
Figure 30B:
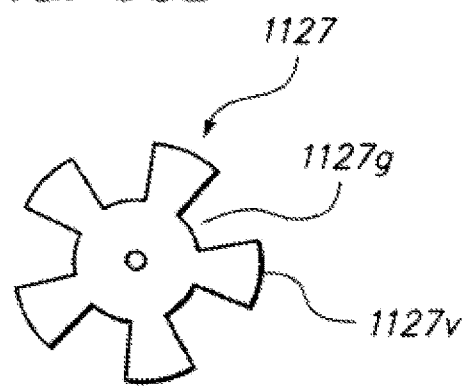
FIG. 30B is an illustration of a plan view of the shutter of FIG. 30A.

Another optional feature that guidewire 110 may be provided with is the ability to emit strobed, flashing or flickering light. The transillumination produced by a flashing light can be further distinguished from diffuse transillumination produced by other light sources, such as endoscopes, for example, since the transillumination produced by the guidewire 110 in this case will flicker or vary in intensity between bright and dim. To produce this type of light, either a light source having strobing capability could be connected to the device 110, or connector 1120 may be provided with this capability. When using a laser light source or an LED as the light emitter, as described in embodiments above, a blinking or strobing effect can be electronically generated according to techniques known in the electronics and lighting arts. FIG. 30A schematically illustrates a connector 1120 having a rotating shutter 1127 rotatably mounted therein so that the vanes 1127v and gaps 1127g between the vanes (see plane view in FIG. 30B) become successively aligned with the light pathway through the connector 1120 to alternate emission and blocking of light transmission out of the connector 1120 and ultimately through device 110 when a device 110 is connected thereto. Shutter 1127 can be powered by a motor 1129 that is either battery powered or connectable to an operating room power source, and motor can be operated by the user via actuator 1131, which can be configured to turn the motor on and off, and optionally can be configured to vary the speed of rotation. Alternatively, shutter can be configured so that vanes 1127v extend through a slot in connector 1120 whereby a user can manually rotate the shutter to cause the light emitted from device 110 to flicker.

Figure 31:
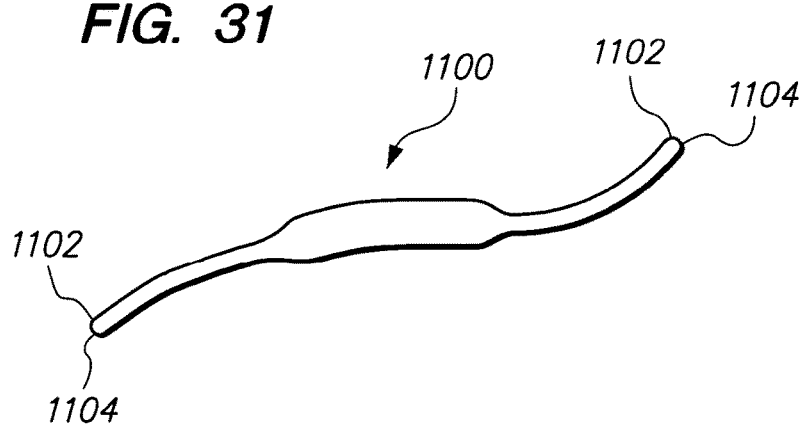
FIG. 31 shows a frontal ostium seeker instrument that can be used to access a sinus ostium.

Other instruments that are designed to be inserted into a sinus, or at least to be positioned at the ostium of a sinus can also be provided with illumination capability according to any or all of the features described above with regard to illumination guidewires. FIG. 31 shows a frontal ostium seeker 1100 instrument that can be used to access a sinus ostium. For example, seeker 1100 may be provided with a length of about 175 mm to about 250 mm (about 208 mm in the example shown) and a ball tip at one or both ends 1102 of the instrument. In FIG. 31, seeker 1100 is also provided with a light emitter 1104 at one or both ends of the device 1100 that can be used to locate an end of device 1100 as it is being advanced to seek an ostium, by the transillumination effects as discussed above. Light emitters 1104 may be provided by LED, light illumination fibers or laser illumination fibers, for example. One or both end portions of the instrument may include a light fiber bundle or electrical wires for connection to a light source or power source in a manner as described above.

Figure 32:
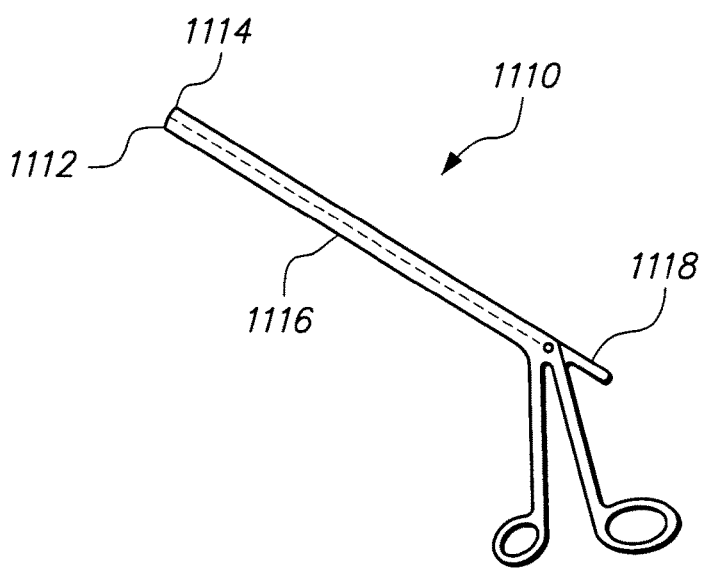
FIG. 32 shows a suction sinus instrument that is configured to evacuate blood and/or other fluids from a target surgical site, such as the frontal sinus.

FIG. 32 shows a suction sinus instrument 1110 that is configured to evacuate blood and/or other fluids from a target surgical site, such as the frontal sinus, sphenoid sinus or other sinus, to improve visibility of a surgical procedure. Instrument 1110 includes an elongated shaft 1116 with a distal end that opens to deliver suction via a suction lumen end 1112. Additionally, a light emitter 1114 is provided at the distal end of shaft 1116, which may be an LED or one or more illumination fibers configured to transmit light in a manner as described above. Shaft 1116 is configured and dimensioned to be inserted into the sinus passageways and sinuses. The proximal end portion of instrument 1110 may include a light fiber bundle 1118 or electrical wires for connection to a light source or power source in a manner as described above.

Figure 33:
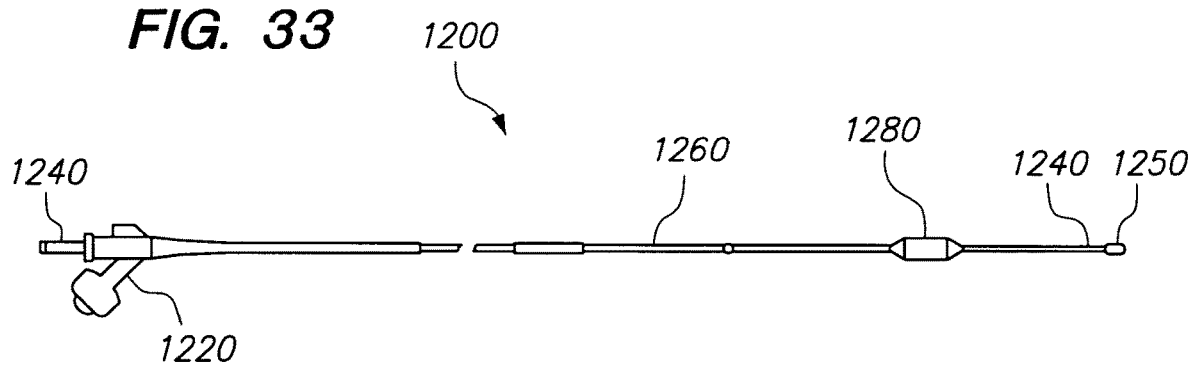
FIG. 33 shows an integrated wire dilatation catheter 120 that includes an elongate, flexible catheter shaft having a balloon mounted thereon.

FIG. 33 shows an integrated wire dilatation catheter 1200 that includes an elongate, flexible catheter shaft 1260 having a balloon 1280 mounted thereon. A proximal Luer hub 1220 is attached to the proximal end of the catheter shaft 1260. An inflation device (not shown) may be attached to the Luer hub 1220 and used to inflate and deflate the balloon 1280. A non-removable, integrated guide member 1240 extends out of and beyond the distal end of the catheter shaft 1260. Guide member 1240 can extend through the length of catheter shaft 1260 and extend proximally thereof as shown in FIG. 33. The proximal end portion may be configured with a polished proximal end containing illumination fibers, as described previously, or may have one or more electrical wires extending proximally thereof for connection with an electrical power source to deliver electrical power to an LED, for example. A light emitter 1250 may be provided at the distal tip of integrated guide member 1240, as shown in FIG. 33 and may be one or more LEDs or one or more illumination fibers, according to any of the different embodiments described above. Alternatively, light emitter 1250 may be provided proximally of the distal tip of guide member 1240, in a manner like that described with regard to FIG. 20, for example. Further alternatively, guide member may not extend through the entire length of catheter 1260 or may not extend proximally of balloon member 1280 at all. In these examples, light emitter may be an LED, wherein wires can be threaded through or alongside of catheter 1260 and into guide member 1240 to connect with the LED. Further alternatively, if light emitter 1250 comprises one or more illumination fibers, the illumination fibers may extend proximally of the proximal end of the guide member 1240, and proximally through catheter 1260 where they are not surrounded by an external sheath in a guidewire formation.

In one preferred embodiment for adult applications, balloon catheter 1200 has an overall length of approximately 43.5 cm and its shaft 1260 has an outer diameter of about 0.058 inches. Further details about integrated wire dilatation catheters that may be configured with a light emitter in a manner as described herein can be found in co-pending application Ser. No. 11/438,090 filed May 18, 2006, now U.S. Pat. No. 8,951,225, issued Feb. 10, 2015 and titled "Catheters with Non-Removable Guide Members Useable for Treatment of Sinusitis. Application Ser. No. 11/438,090, now U.S. Pat. No. 8,951,225 is hereby incorporated herein, in its entirety, by reference thereto.

Extra Long Endoscope

Figure 34:
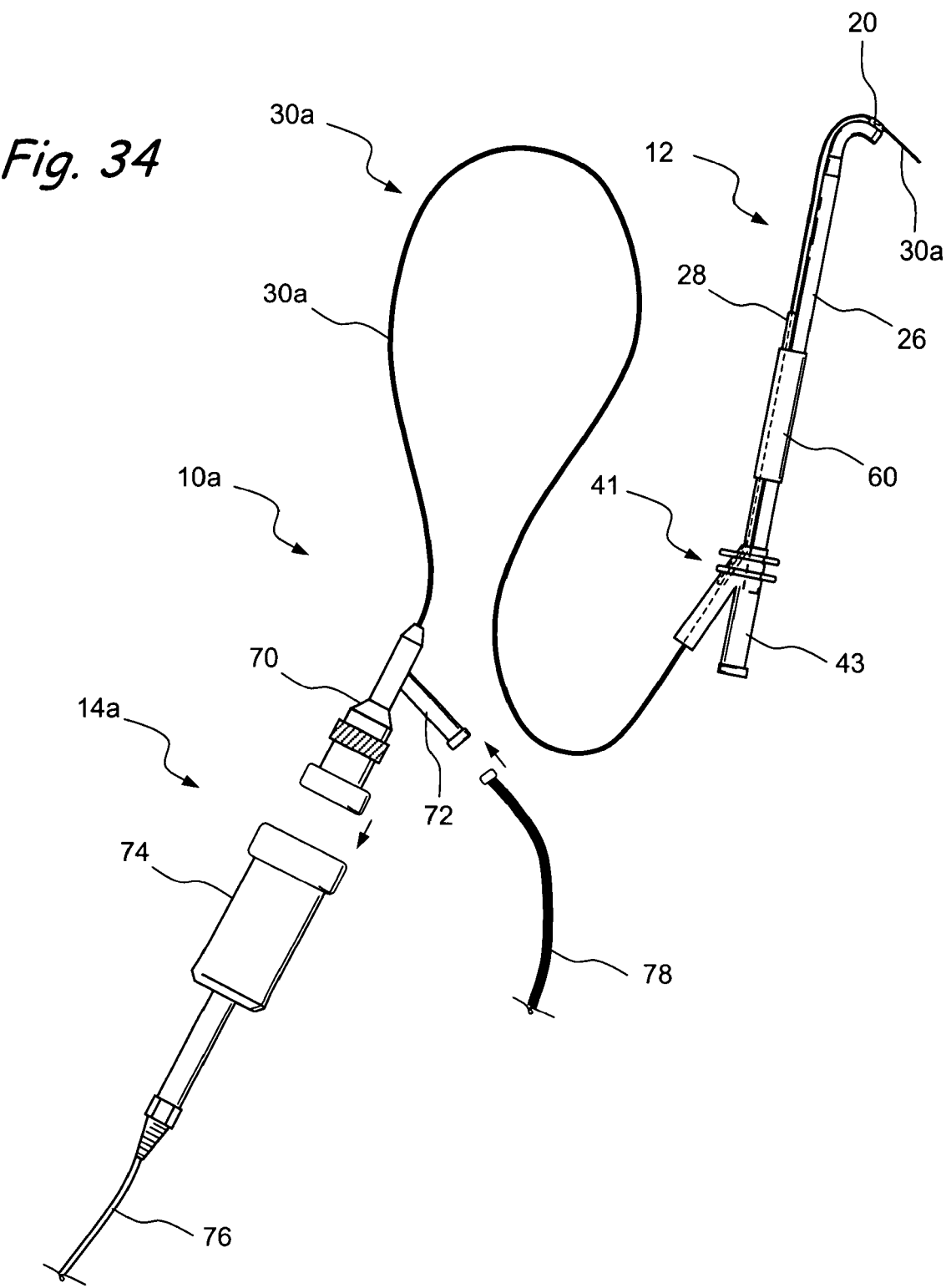
FIG. 34 is a perspective view of another guide catheter system of the present invention incorporating the guide catheter component of FIG. 4A in combination with a long flexible endoscope and camera assembly.
Figure 35:
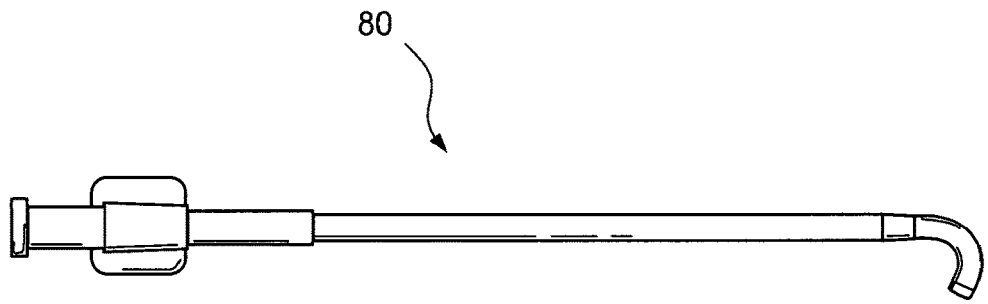
FIG. 35 is a side view of a transnasal guide catheter.

As seen in FIG. 2, when the system 10 shown in FIG. 1 is used, the camera/transmission/endoscope assembly 14 is attached to the proximal end of the sinus guide device 12 and must be held or supported a spaced distance above the subject's chest during performance of the procedure. FIG. 34 shows an alternative system 10*a* which incorporates a long flexible endoscope 30*a*, and a different camera/transmission/endoscope assembly 14*a*.

The long flexible endoscope 30*a* has an extended length, preferably at least about two feet long, such that a portion of the flexible endoscope 30 extends between the proximal end of the sinus guide 12 and the camera/transmission/endoscope assembly 14*a*, thereby allowing the camera/transmission/endoscope assembly 14*a* to rest upon the subject's chest or on a nearby structure (e.g., a tray, clip, clamp, on the adjacent surface of the operating table, etc.). This eliminates the need for the operator to hold or support the weight of the camera/transmission/endoscope assembly 14*a* in addition to that of the sinus guide 12. Rather, with the camera/transmission/endoscope assembly 14*a* resting upon the subject's chest or on a nearby structure, the operator need only hold or support the sinus guide 12, thereby enabling the operator to potentially handle or operate other secondary devices, such as a second endoscope that may be inserted separately from and in addition to the endoscope 30*a* that passes through the sinus guide 12. The long flexible endoscope 30*a* has utility in both therapeutic and diagnostic uses.

The modified camera/transmission/endoscope assembly 14*a* shown in FIG. 34 need not include a connector for rigidly attaching it to the proximal hub 41 of the sinus guide device 12. Rather, this camera/transmission/endoscope assembly 14*a* comprises an eyepiece 70 and a light post 72, preferably an ACMI light post with an integrated light taper, to which a light cable 78 may be attached. A length of the flexible endoscope 30*a* extends from this eyepiece to the proximal hub 41 of the sinus guide 12 and beyond through the guide. A camera 74 has a coupler on its distal end so as to clamp onto the proximal end of the eyepiece 70. An image cable 76 extends from the camera 74 to a monitor where the image is displayed. The flexible endoscope 30*a* has a coherent bundle of extremely small and highly packed fiber optic fibers with light fibers around the image fibers. For example, the flexible endoscope 30*a* can be a fiber scope having about 6,000 thin image fibers in a bundle, preferably at least about 10,000 thin image fibers for better resolution of the image. The light fibers are preferably illumination fibers with a diameter between about 0.008 and 0.020 inches and a minimum lux of about 10,000. The diameter of the flexible endoscope 30*a* ranges from about 0.25 mm to about 1 mm and is preferably about 0.3 mm in diameter, and has a flexible outer sheathing of braided polyimide. The field of view is preferably about 70 degrees. The field of view could also be "straight ahead" (i.e., zero degrees) or at other angles (e.g., 30, 45 or 60 degrees) as is available in commercial endoscopes.

Guide Systems with Removable Endoscope/Guidewire Sheaths

FIGS. 35-38D show another transnasally insertable guide system useable to position a guidewire at a desired location within the ear, nose, throat or cranium of a human or animal subject. This guide system comprises a straight or curved transnasal sinus guide 80 and a sheath 90 that is insertable through the sinus guide 80. The sheath 90 has an endoscope lumen 85 through which a flexible endoscope 30 may be inserted and a guidewire lumen 87 through which a guidewire 110 may be inserted. An endoscope 30 inserted through the endoscope lumen 85 may be advanced substantially parallel to the guidewire 110 inserted through the guidewire lumen 87 so as to view, guide or verify the positioning of the guidewire 110. As noted earlier, guidewire 110 can also be used to extend the viewing range of endoscope 30 when the guidewire used is an illuminating guidewire 110 and the illuminating portion of the guidewire 110 is extend distally beyond the viewing portion of endoscope 30.

Examples of transnasal sinus guides 80 useable in this system include those described in U.S. patent application Ser. No. 11/193,020, published as U.S. Pub. No. 2006/0063973 on Mar. 23, 2006, now abandoned and those currently available commercially as Relieva™ Sinus Guide Catheters from Acclarent, Inc., Menlo Park, Calif.

Figure 36:
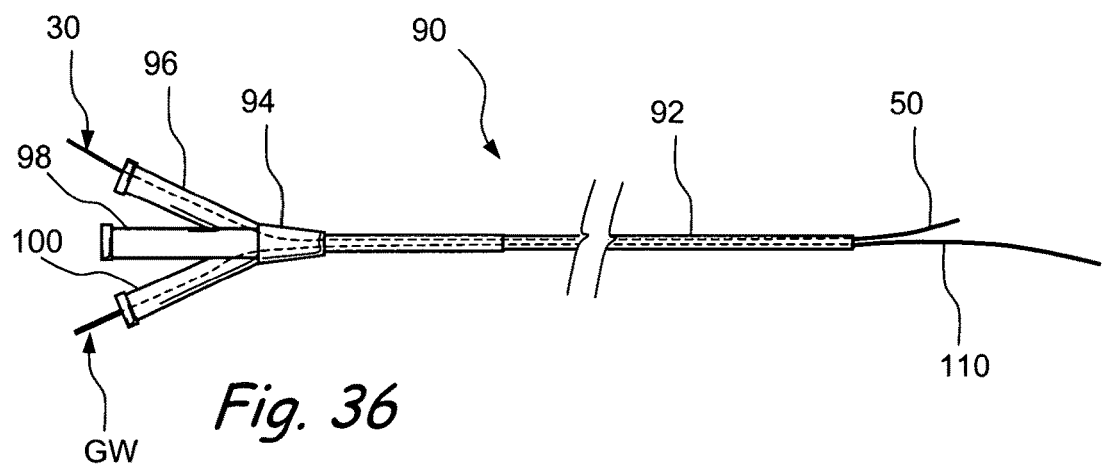
FIG. 36 is a side view of a sheath that is insertable through the guide catheter of FIG. 35 to facilitate endoscopically guided advancement of a guidewire through the guide catheter of FIG. 35.

The details of the sheath 90 are shown in FIG. 36. The sheath 90 comprises an elongate flexible shaft 92 through which the endoscope lumen 85 and guidewire lumen 87 extend. A proximal hub 94 having three arms 96, 98, 100 is mounted on the proximal end of the flexible shaft. Arm 96 leads into the endoscope lumen 85 and arm 100 leads into the guidewire lumen 87.

Figure 15:
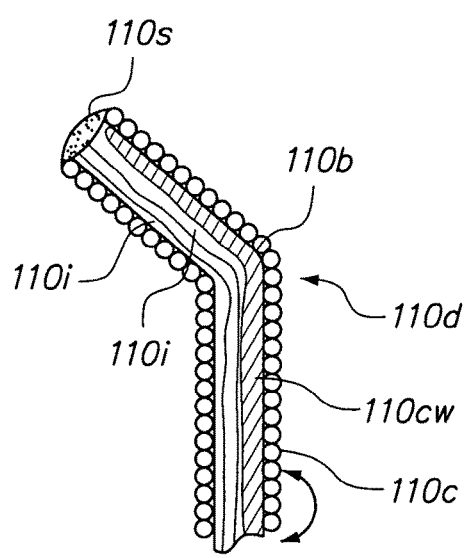
FIG. 15 shows a distal end portion of a guidewire having a bent shape.
Figure 37:
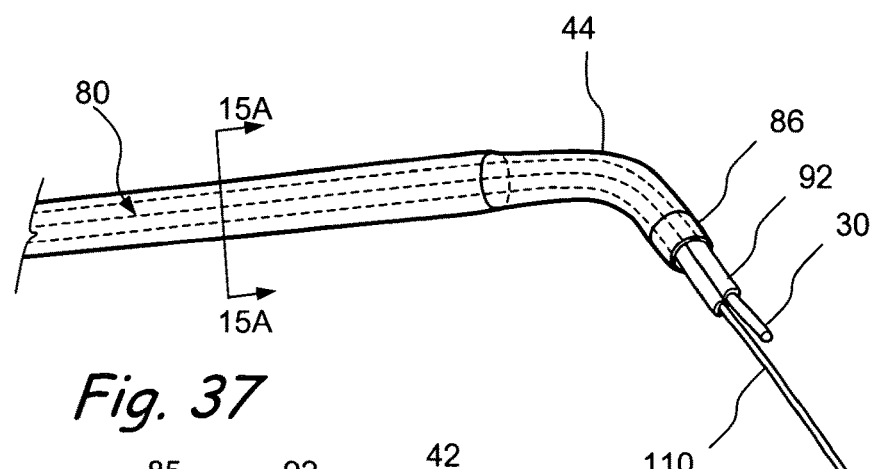
FIG. 37 is an enlarged view of a distal portion of the guide catheter of FIG. 35 having the sheath of FIG. 36, an endoscope and a guidewire operatively inserted therethrough.
Figure 37:
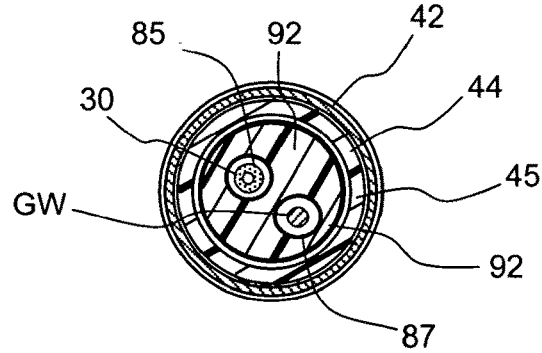
Figure 38:
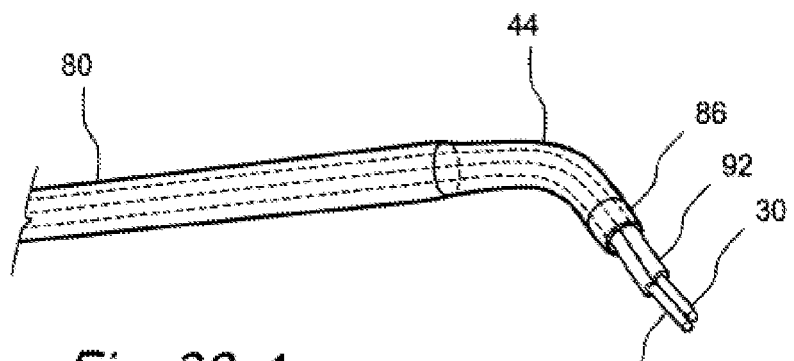
FIGS. 38A-38D show steps in a method for using the guide catheter of FIG. 35 in combination with the sheath device of FIG. 36 to facilitate endoscopically guided placement of a guidewire.
Figure 38:
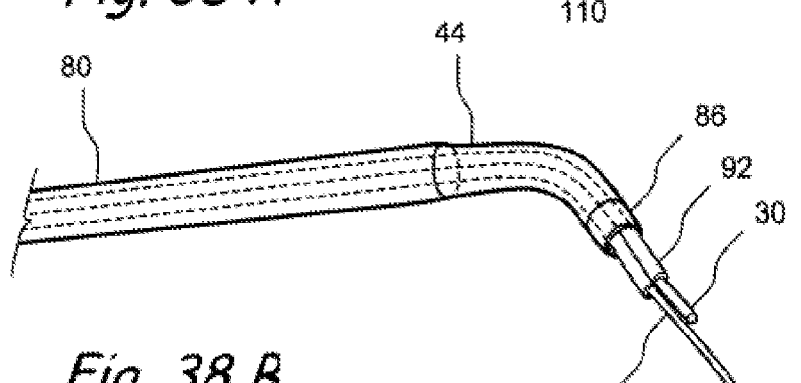
Figure 38:
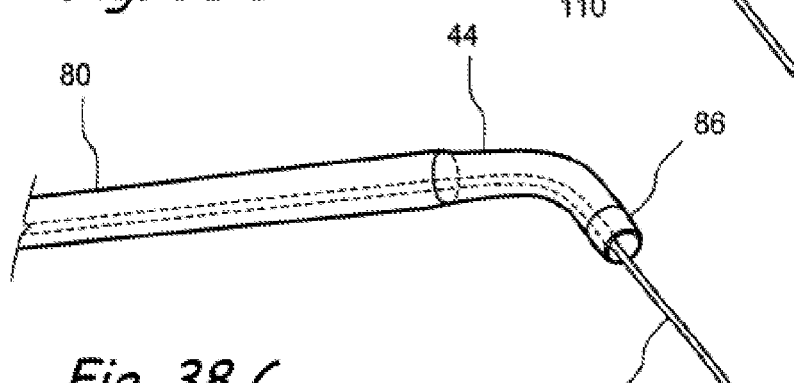
Figure 38:
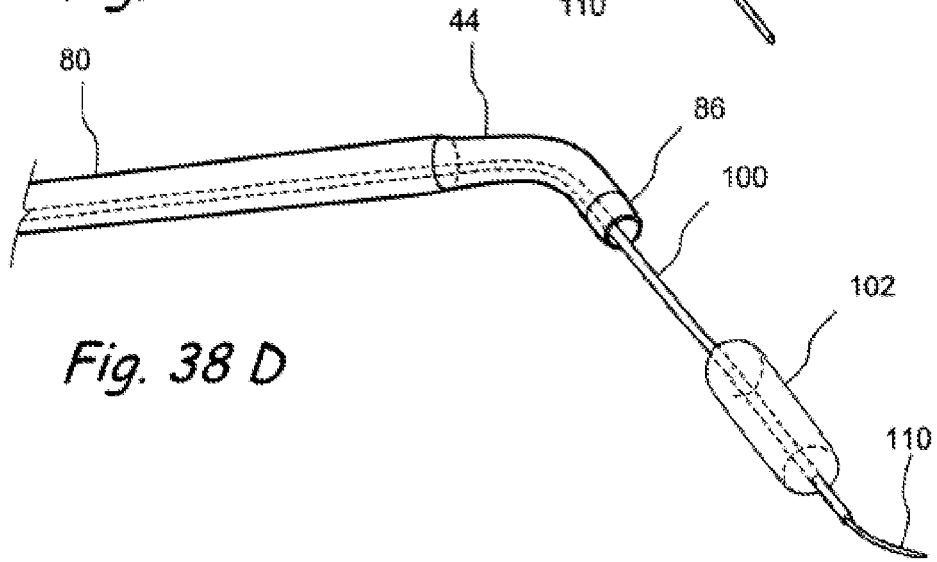

FIGS. 37 and 37A show the sheath 90 inserted through one type of sinus guide 80 with an endoscope 30 and guidewire 110 inserted through the respective lumens 85, 87 of the sheath. The sinus guide comprises a tube 44 having a lumen 45, such as a polymer tube made of biocompatible polymer. Optionally, a liner (not shown in FIG. 15A) may be disposed within the lumen 45 of the tube 44. Such liner may be formed of lubricious or smooth material such as polytetrafluoroethylene (PTFE). Also, optionally, a proximal portion of the tube 44 may be surrounded by an outer tube member 42 formed of material such as stainless steel hypotube. In the embodiment shown, a curved distal portion of tube 44 extends out of and beyond the distal end of outer tube 42. Additionally, a radiographically visible marker 86 may optionally be formed on or attached to the distal end of the sinus guide 80. The flexible shaft 92 of the sheath 90 is advanceable through lumen 45 of tube 44. As seen in FIG. 15, a distal portion of the sheath shaft 92 may extend out of and beyond the distal end of the sinus guide 80. Also, as seen in FIG. 37, distal portions of the endoscope 30 and guidewire 110 may advance out of and beyond the distal end of shaft 92.

FIGS. 38A-38D show an example of steps in a method for using the guide catheter 80 and sheath 90 shown in FIGS. 35-37A to perform a procedure wherein a balloon catheter is used to dilate an anatomical structure such as the ostium of a paranasal sinus.

Initially, as seen in FIG. 38A, the sinus guide 80 is inserted transnasally and advanced to a position where the distal end of the sinus guide is substantially aligned with but a spaced distance away from the anatomical structure to be dilated (see an example of such spacing in FIGS. 10A and 10B). Thereafter, the shaft 92 of sheath 90 is advanced through the lumen 45 of the sinus guide such that a distal portion of the sheath is flush with or protrudes out of the distal end of the sinus guide 80. The guidewire 110 is then advanced out of the end of sheath 90 while the endoscope 30 is used to view, guide and/or verify the position of the guidewire. In some instances, it may be desirable to advance the endoscope 30 along with the guidewire 110 so that the distal end of the scope remains an optimal distance behind the distal end of the guidewire, as seen in FIG. 38B. Such positioning of the endoscope 30 may allow the operator to observe the distal end of the guidewire 110 as it is advanced into or through the anatomical structure to be dilated.

After the guidewire 110 has been advanced into or through the anatomical structure to be dilated, the sheath 90 and endoscope 30 are withdrawn and removed, leaving the sinus guide 80 and guidewire 110 in place, as seen in FIG. 38C.

Thereafter, as shown in FIG. 38D, a balloon catheter 100 is advanced over the guidewire 110 and through the sinus guide 80 to a position where its balloon 102 is positioned within the ostium or other anatomical structure to be dilated. The balloon 102 is then inflated, thereby performing the desired dilation.

Figure 39:
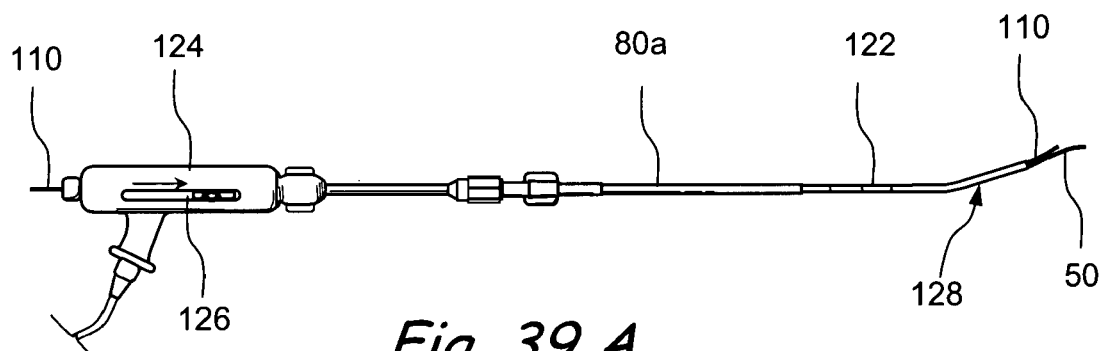
FIG. 39A is a perspective view of a deflectable (e.g., steerable) sheath device of the present invention in combination with a transnasally insertable guide catheter, a guidewire and an endoscope.
FIGS. 39B and 39C show steps in a method for using the deflectable sheath device of FIG. 39A to facilitate placement of a guidewire.
FIG. 39D shows the guidewire and guide catheter after removal of the steerable sheath and endoscope.
Figure 39:
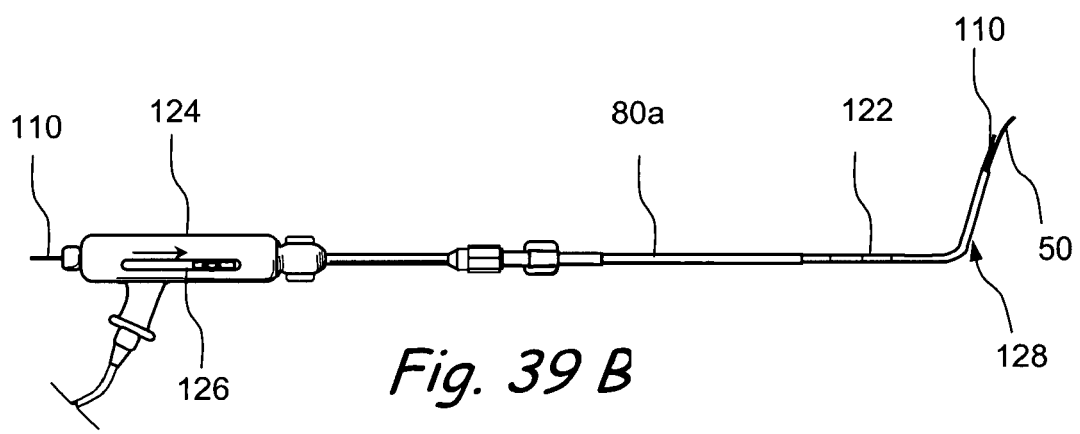
Figure 39:
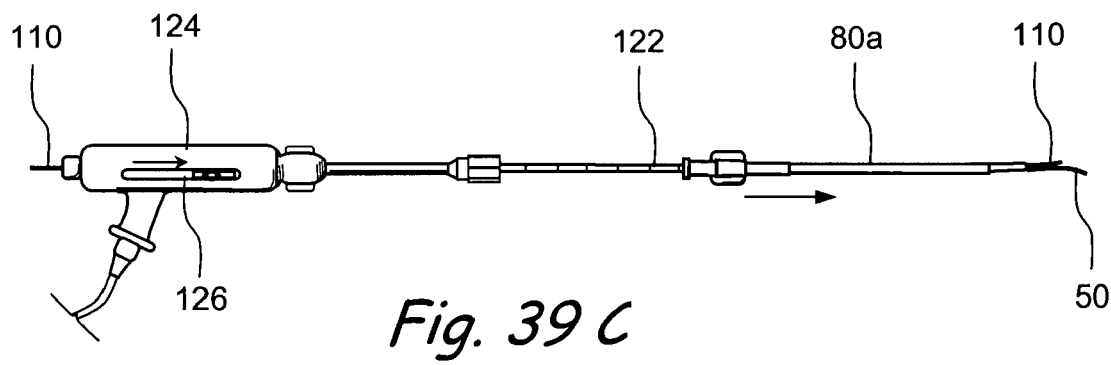
Figure 39:
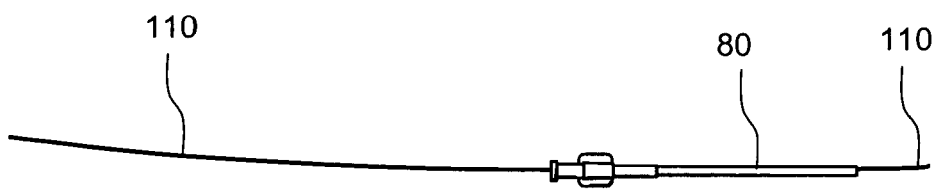
Figure 40:
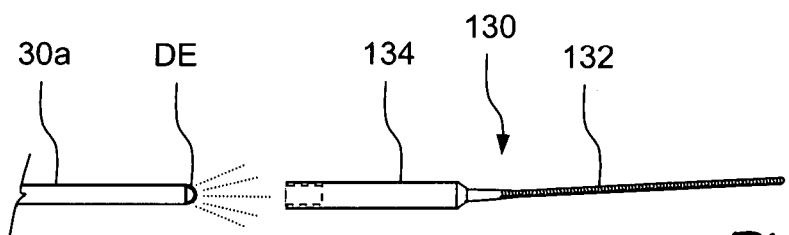
FIG. 40A is a partial exploded view of a guide system having an elongate guide tip, a translucent body and an endoscope that is engageable with the translucent guide body.
FIG. 40B shows the guide system of FIG. 40A in an assembled, operative state.
FIG. 40C is a schematic diagram of an endoscope monitor showing a view received by the endoscope component of the system shown in FIGS. 40A and 40B.
FIG. 40D is a partial perspective view of a guide system having an elongate guide member attached to and extending from the distal end of a catheter that has a side opening out of which an endoscope advances to view an area adjacent to the guide member.
FIG. 40E is a schematic diagram of an endoscope monitor showing a view received by the endoscope component of the system shown in FIG. 40D.
Figure 40:
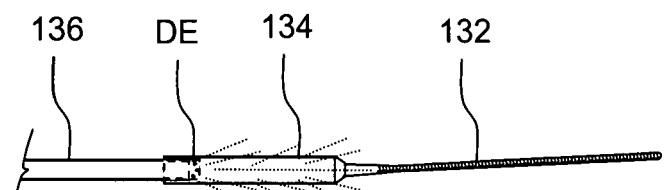
Figure 40:
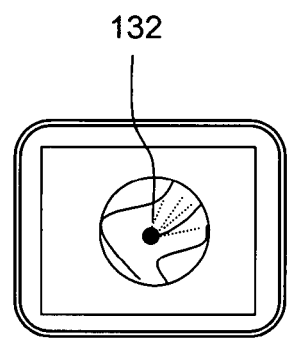
Figure 40:
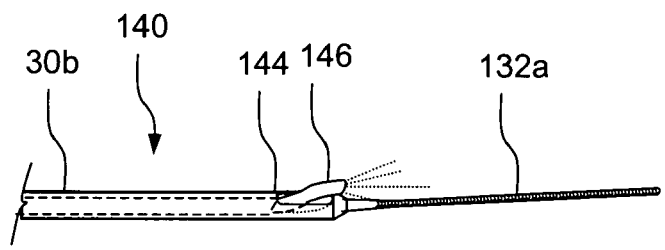
Figure 40:
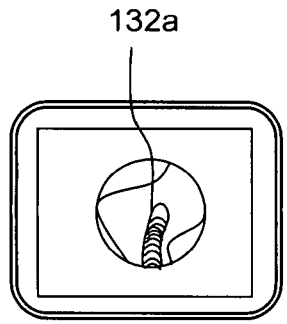
Figure 41:
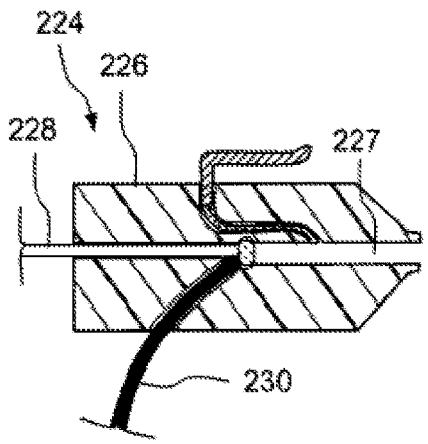
FIG. 41A is a sectional view of a proximal connector device of the present invention positioned adjacent to the device of FIG. 40A.
FIG. 41B is a sectional view of a proximal connector device of the present invention positioned adjacent to the device of FIG. 40D.
Figure 41:
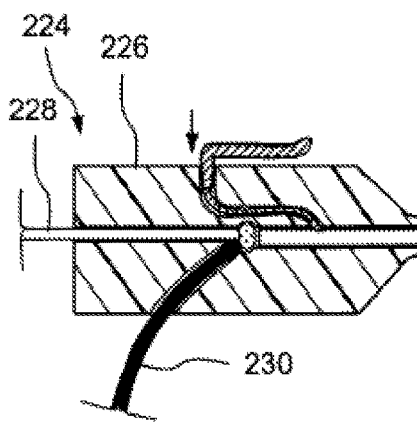
Figure 41:
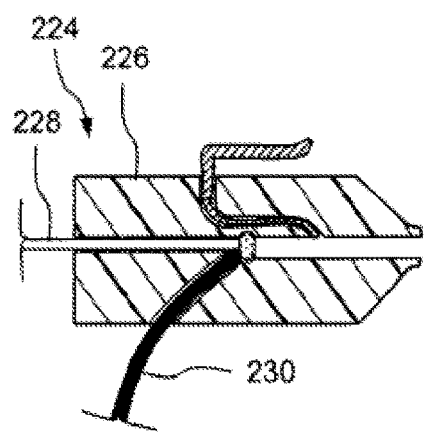
Figure 41:
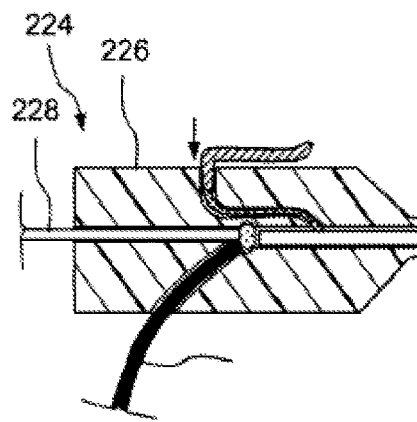

In the example of FIGS. 38A-38C, a flexible sheath 90 is advanced through a straight or curved sinus guide 80. However, in some applications, it may be desirable to steer the sheath 90 within the body, thereby allowing the sheath 90 to be navigated through tortuous anatomical regions and/or around anatomical structures. In this regard, FIGS. 39A through 39D show another system which utilizes a straight sinus guide 80a in conjunction with a steerable sheath 122 that has endoscope and guidewire lumens extending therethrough. A handpiece 124 on the proximal end of the sheath 122 has an actuator 126 that moves a pull wire or otherwise causes a distal portion 128 of the sheath 122 to deflect or bend. The distal portion 128 of this sheath 122 may be slightly deflected as seen in FIG. 39A, severely deflected as seen in FIG. 39B, not deflected (straight) as seen in FIG. 39C, or any variations therebetween.

In operation, the sinus guide 80a is inserted into or through a nostril and the sheath 122 is inserted through the sinus guide and is advanced to a desired location. During such advancement of the sheath 122, the endoscope 30 may be used to view the area immediately ahead of the sheath 122 and the operator may use actuator 126 to steer or deflect the sheath 122 as needed to navigate the sheath 122 to the desired location. After the sheath 122 has been navigated to a desired position, the guidewire 110 may be advanced, under endoscopic guidance, as described above with respect to the example of FIGS. 38A-38D. After the guidewire 110 has been advanced to the desired location, the steerable sheath 122 and endoscope 30 are withdrawn and removed, leaving the sinus guide 80a and guidewire 110 in place, as seen in FIG. 39D. Thereafter, a working device (e.g., a balloon catheter or other diagnostic or therapeutic apparatus) may be advanced over the 110 and used to perform a therapeutic or diagnostic function.

Guide Systems Having Small Diameter Endoscopes Attached to Guidewire Tips

FIGS. 40A through 41B' are directed to guide systems wherein a guidewire tip is attached to an endoscope and used to view, guide or verify the position of the guidewire tip. After the guidewire tip has been advanced to an intended location, a working device (e.g., another catheter, balloon catheter, etc.) may be advanced over the endoscope and over the guidewire tip. To allow devices to be advanced over the endoscope, it is necessary to remove any bulky or large diameter hubs or attachments from the proximal end of the endoscope. Thus, as shown on the FIG. 41 series, this invention includes removable proximal hubs for endoscopes of this type.

Referring specifically to FIGS. 40A-40C, there is provided a guide system 130 comprising a flexible endoscope 30a, a translucent endoscope-receiving body 134 and an elongate guide tip 132, such as a flexible guidewire tip. The distal end of the endoscope 30a is inserted into or otherwise coupled or attached to the proximal end of the translucent body 134 such that light will be cast from the endoscope 30a, through the translucent body 134 and images will be received by the endoscope 30a through the translucent body 134. In this manner, the endoscope 30a is useable to view an area adjacent to the elongate guide tip 132 thereby facilitating advancement of the elongate guide tip to a desired location within the body of a human or animal subject. In some embodiments, the endoscope 30a may provide a 360 degree view around the periphery of the elongate guide tip 132 as shown in the diagram of FIG. 40C.

After the elongate guide tip 132 has been advanced to a desired location (e.g., into or through the ostium of a paranasal sinus) as working device (e.g., a catheter such as a balloon catheter or other diagnostic or therapeutic device) is advanceable over the endoscope 30a, over the translucent body member 134 and over the elongate guide tip 132. This may require detachment of any large diameter or bulky hub or other component from the proximal end of the endoscope. The detachability configuration described in regard to FIGS. 41A and 41A' applies to other scope embodiments herein and helps to keep the cost of the disposable elements to a minimum. FIGS. 41A and 41A' show a detachable hub 224 that may be attached to and detached from the proximal end of the endoscope 30A. This hub 224 comprises a body 226 having a scope-receiving channel 227 in its distal end, a light input cable 230 and an image output cable 228. As seen in FIG. 41A', the proximal end of the endoscope 30a is inserted into scope-receiving channel 227, thereby causing a light fiber contact on the proximal end of the endoscope 30a to optically couple to a corresponding contact at the proximal end of scope-receiving channel 227 so that light from light cable 230 will be transmitted in the distal direction through the light fibers of the endoscope 30a. Also, this will cause an image contact formed on the endoscope 30b to be optically coupled to a corresponding contact on the inner wall of the scope-receiving channel 227 such that images from the scope's image fibers will be transmitted through image cable 28 to a camera/monitor, eyepiece or other image viewing apparatus known in the art of endoscopy. After the elongate guide tip 132 has been placed in the desired position, the proximal end of the endoscope 30a may be pulled out of scope-receiving channel 227 and the hub 224 may be removed, thereby allowing the working device to advance over and be guided by the body of the endoscope 136, translucent member 134 and elongate guide tip 132.

Referring specifically to FIGS. 40D-40E, there is provided another guide system 140 comprising an endoscope 30b attached to an elongate guide tip 132a, such as a flexible guidewire tip. In this example, the endoscope 30b comprises an outer tube having a side opening 144 and a flexible endoscope tip 146 that is advanceable out of and retractable back into the side opening 144. When advanced out of the side opening 144, the endoscope tip 146 is useable to view an area adjacent to the elongate guide tip 132a, thereby facilitating advancement of the elongate guide tip 132a to a desired location. When the endoscope tip is advanced out of the side opening 144, it may provide a view along one side of the guide tip 132a, as seen in the diagram of FIG. 40E.

After the elongate guide tip 132a has been advanced to the desired location, the endoscope tip 146 is retracted back into the endoscope's outer tube through side opening 144 and a working device (e.g., a catheter such as a balloon catheter or other diagnostic or therapeutic device) is advanceable over the endoscope 30b and over the elongate guide tip 132a. To facilitate this, the above-described detachable hub 224 may be used in conjunction with this endoscope 30b, as seen in FIGS. 41B and 41B'.

Self Cleaning Endoscope Feature

Figure 42:
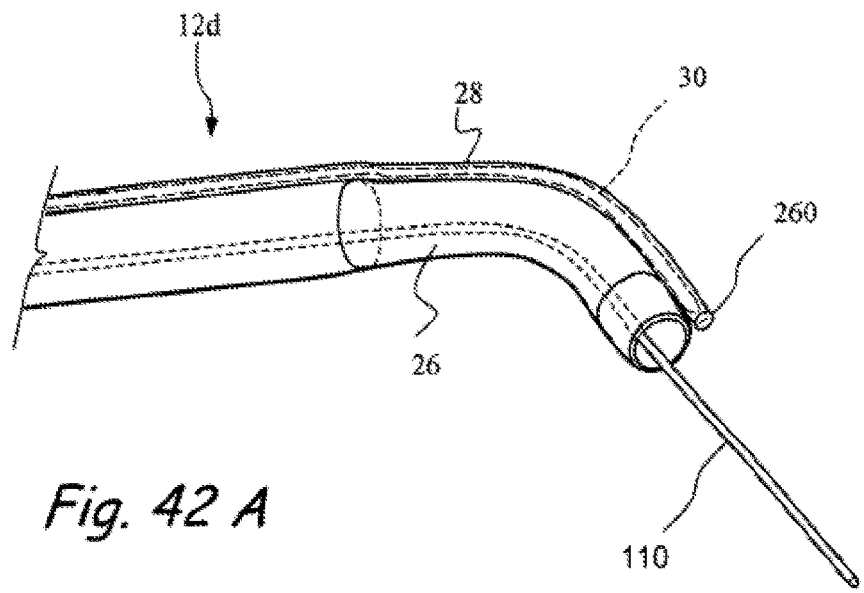
FIGS. 42A-42C are partial perspective views of the distal ends of curved guide catheters of the present invention having an endoscope with a distal end for cleaning a flexible endoscope translatable in the channel.
Figure 42:
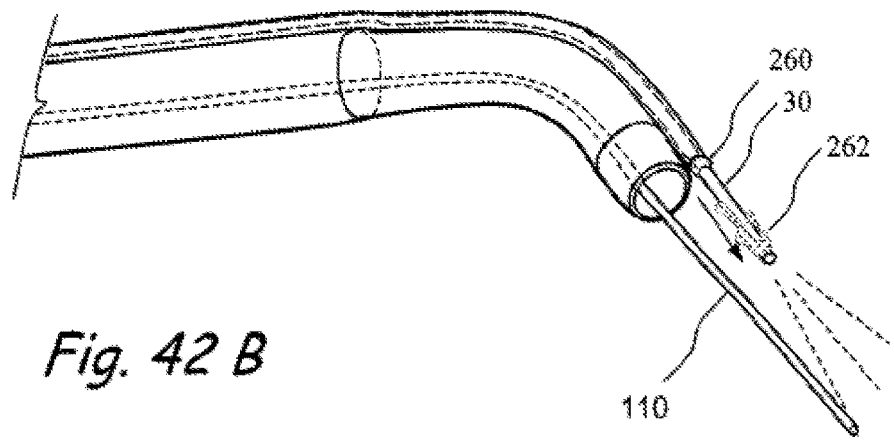
Figure 42:
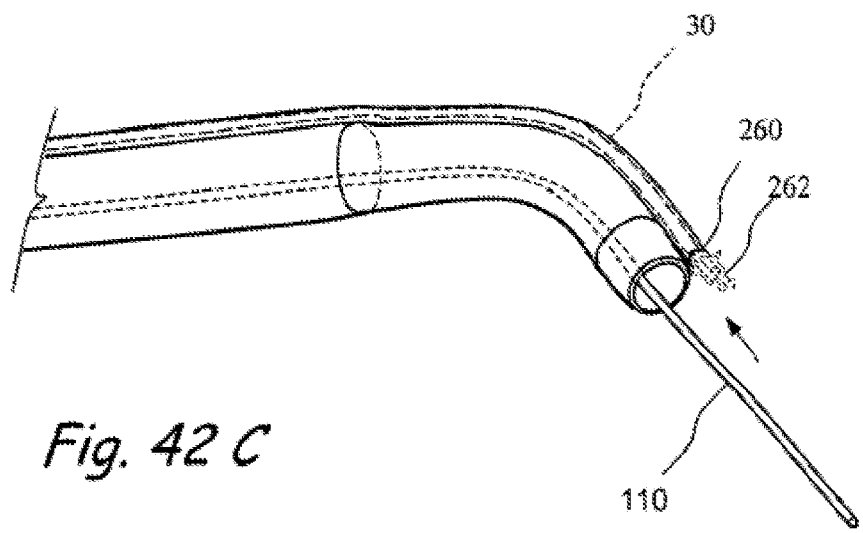

Any of the sinus guides 12, 12a, 12b, 12c, 80 of this invention may incorporate apparatus, such as a drip line, mist, suction or feature on the sinus guide, for cleaning debris from the endoscope without requiring the device to be removed from the subject's body. In this regard, FIGS. 42A-20C show one example of an endoscope sinus guide 12d having a scope cleaning member 260 at the distal end of its endoscope channel 28. In this example, the scope cleaning member 260 comprises an elastomeric diaphragm disposed transversely over the distal end of the endoscope channel 28 and having a self-closing slit through which the endoscope 30 passes. It will be appreciated, however, that such scope cleaning member 260 need not necessarily be a slit elastomeric diaphragm, but may comprise various other types of members that wipe or frictionally clear the distal end of the endoscope 30 as the endoscope is advanced or retracted.

In the example shown, the endoscope is advanced through the slit and out of the endoscope channel 28, where it is used to observe the advancement of a guidewire 110 from the adjacent sinus guide body 26. During such procedure, a quantity of debris 262 (e.g., blood, mucous, etc.) accumulates on the distal end of the endoscope, thus interfering with obtainment of a suitable quality image from the endoscope 30. To remedy this, the endoscope is briefly retracted back through the scope cleaning member 260 such that the slit rides over the outer surface of the endoscope 30 and closes over the distal tip of the endoscope 30 as it is retracted. This removes the debris 262 from the endoscope 30, as shown in FIG. 42C. Thereafter, the endoscope 30 may be re-advanced through scope cleaning member 260 and may once again be used to obtain an endoscope image of the guidewire 110 and/or other areas around the distal end of the sinus guide device 12d.

It is to be appreciated that the invention has been described hereabove with reference to certain examples or embodiments of the invention but that various additions, deletions, alterations and modifications may be made to these examples and embodiments and or equivalents may be substituted without departing from the intended spirit and scope of the invention. For example, any element or attribute of one embodiment or example may be incorporated into or used with another embodiment or example, unless to do so would render the embodiment or example unsuitable for its intended use. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A method of using a dilation system to treat an anatomical passageway in a head of a patient, wherein the dilation system comprises a body and an endoscopic guide, wherein the endoscopic guide is securely attached to the body;

the method comprising:
(a) inserting an endoscope through the endoscopic guide such that the endoscope is selectively fixedly secured relative to the body;
(b) inserting an instrument through the body such that the instrument is slidably secured relative to the body;
(c) inserting a distal end of the body into the head of the patient;
(d) maneuvering the distal end of the body toward the anatomical passageway by visualizing the anatomical passageway through the endoscope; and
(e) treating the anatomical passageway with the instrument, wherein the instrument comprises an expandable dilator, wherein treating the anatomical passageway comprises expanding the expandable dilator to thereby dilate the anatomical passageway, wherein visualizing the anatomical passageway through the endoscope is performed from a location external to the expandable dilator,
wherein the endoscopic guide comprises a proximal guide and a distal guide such that the proximal guide is separated from the distal guide, wherein inserting the endoscope through the endoscopic guide comprises inserting the endoscope through the proximal guide and the distal guide.

2. The method of claim 1, further comprising selecting the body from a plurality of bodies based on a particular type of anatomical passageway in the head of the patient to be treated.

3. The method of claim 1, further comprising attaching a camera, cable, light, or endoscope assembly to a proximal end of the body.

4. The method of claim 1, further comprising forming a slack portion between the proximal and distal guides when maneuvering the endoscope from the proximal guide into the distal guide.

5. The method of claim 4, further comprising actuating a moveable sheath along the body from a retracted position to an extended position to thereby compress the slack portion against the body.

6. The method of claim 1, wherein the proximal guide is attached to the body at a proximal end and the distal guide is attached to the body at the distal end, wherein the proximal end extends along a first axis and the distal end extends along a second axis that is transverse to the first axis such that the distal guide is transversely oriented relative to the proximal guide.

7. The method of claim 6, wherein inserting the endoscope through the endoscopic guide comprises inserting the endoscope through the proximal guide along the first axis, maneuvering the endoscope from the first axis to the second axis, and inserting the endoscope through the distal guide along the second axis.

8. The method of claim 1, further comprising inserting the body through a fixture device such that the distal end of the body and the endoscopic guide are removably coupled to the fixture device.

9. The method of claim 8, further comprising inserting the endoscope through the fixture device after exiting a proximal guide of the endoscopic guide.

10. The method of claim 9, further comprising advancing the endoscope through the fixture device until entering a distal guide of the endoscopic guide.

11. The method of claim 10, further comprising detaching the body from the fixture device such that the distal end of the body and the endoscopic guide are decoupled from the fixture device prior to inserting the distal end of the body into the head of the patient.

12. The method of claim 1, further comprising inserting the endoscope into a linking device after the endoscope exits the endoscopic guide to thereby position the endoscope about the distal end of the body.

13. The method of claim 1, further comprising locking the endoscope relative to the body such that a longitudinal position of the endoscope within the endoscopic guide becomes fixed.

14. A method of treating an anatomical passageway in a head of a patient, the method comprising:
(a) inserting a guide catheter through a fixture device such that a distal end of the guide catheter and a guide channel secured to the guide catheter are removably coupled to the fixture device;
(b) inserting an endoscope through the guide channel, thereby positioning a distal end of the endoscope near the distal end of the guide catheter, and thereby forming a combination of the endoscope and the guide catheter;
(c) grasping the combination of the endoscope and the guide catheter and thereby moving the combination of the endoscope and the guide catheter to position the distal end of the endoscope and the distal end of the guide catheter in the head of the patient;
(d) identifying a targeted anatomical passageway in the head of the patient;
(e) using the endoscope to visually observe the targeted anatomical passageway in the head of the patient while grasping the combination of the endoscope and the guide catheter;
(f) advancing a dilator along the guide catheter to thereby position the dilator in the targeted anatomical passageway; and
(g) expanding the dilator to thereby dilate the anatomical passageway, wherein using the endoscope to visually observe the targeted anatomical passageway is performed with the distal end of the endoscope positioned external to the dilator.

15. The method of claim 14, wherein the endoscope is flexible, the method further comprising forming a bend in the endoscope.

16. The method of claim 14, wherein the anatomical passageway includes an ostium leading to a sinus, wherein expanding the dilator causes the ostium to expand.

17. The method of claim 14, wherein the guide channel comprises a proximal guide channel and a distal guide channel such that the proximal guide channel is separated from the distal guide channel, wherein inserting the endoscope through the guide channel comprises inserting the endoscope through the proximal guide channel and the distal guide channel.

18. A method of using a dilation system to treat an anatomical passageway in a head of a patient, wherein the dilation system comprises a body and an endoscopic guide, wherein the body includes a proximal body portion extending along a first axis and a distal body portion extending along a second axis that is transverse to the first axis, wherein the endoscopic guide includes a proximal guide portion adjacent the proximal body portion and a distal guide portion adjacent the distal body portion, wherein the proximal guide portion is separated from the distal guide portion;
the method comprising:
(a) advancing an endoscope through the proximal guide portion in a first direction parallel to the first axis;

(b) advancing the endoscope through the distal guide portion in a second direction parallel to the second axis;
(c) inserting an instrument including an expandable dilator through the body;
(d) inserting the distal body portion into the head of the patient;
(e) maneuvering the distal body portion toward the anatomical passageway by visualizing the anatomical passageway through the endoscope from a location external to the expandable dilator; and
(f) treating the anatomical passageway with the instrument, wherein treating the anatomical passageway comprises expanding the expandable dilator to thereby dilate the anatomical passageway.

19. The method of claim 18, further comprising forming a bend in the endoscope between advancing the endoscope through the proximal guide portion in the first direction and advancing the endoscope through the distal guide portion in the second direction.

\* \* \* \* \*